US009562025B2

(12) United States Patent
Shih et al.

(10) Patent No.: US 9,562,025 B2
(45) Date of Patent: *Feb. 7, 2017

(54) COMPOUNDS WITH (1E, 6E)-1,7-BIS-(3,4-DIMETHOXYPHENYL)-4-4-DISTRIBUTED-HEPTA-1,6-DIENE-3,5-DIONE STRUCTURAL SCAFFOLD, THEIR BIOLOGICAL ACTIVITY, AND USES THEREOF

(71) Applicant: Allianz Pharmascience Ltd., Taipei (TW)

(72) Inventors: Charles Shih, Solana Beach, CA (US); Qian Shi, Chapel Hill, NC (US); Hui-Kang Wang, San Diego, CA (US)

(73) Assignee: Allianz Pharmascience Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/044,685

(22) Filed: Feb. 16, 2016

(65) Prior Publication Data

US 2016/0264539 A1    Sep. 15, 2016

Related U.S. Application Data

(60) Continuation of application No. 14/622,883, filed on Feb. 15, 2015, now Pat. No. 9,259,402, which is a continuation of application No. 13/920,199, filed on Jun. 18, 2013, now Pat. No. 9,000,222, which is a continuation-in-part of application No. 13/525,941, filed on Jun. 18, 2012, now Pat. No. 8,710,272, which is a continuation-in-part of application No. 12/800,251, filed on May 11, 2010, now Pat. No. 8,202,905, which is a division of application No. 12/008,124, filed on Jan. 8, 2008, now Pat. No. 8,236,852, said application No. 13/525,941 is a continuation-in-part of application No. 12/008,124, filed on Jan. 8, 2008, now Pat. No. 8,236,852.

(60) Provisional application No. 60/879,458, filed on Jan. 8, 2007.

(51) Int. Cl.
C07C 49/255 (2006.01)
C07C 69/618 (2006.01)
C07D 295/192 (2006.01)
A61K 31/00 (2006.01)
C07D 295/16 (2006.01)
C07C 309/65 (2006.01)
C07D 277/46 (2006.01)
C07C 235/78 (2006.01)
A61K 31/12 (2006.01)
A61K 31/165 (2006.01)
A61K 31/426 (2006.01)
A61K 31/5375 (2006.01)
A61K 31/255 (2006.01)
C07C 59/90 (2006.01)
C07C 69/738 (2006.01)
C07C 235/74 (2006.01)
C07D 277/44 (2006.01)

(52) U.S. Cl.
CPC ............ *C07D 295/16* (2013.01); *A61K 31/12* (2013.01); *A61K 31/165* (2013.01); *A61K 31/255* (2013.01); *A61K 31/426* (2013.01); *A61K 31/5375* (2013.01); *C07C 49/255* (2013.01); *C07C 59/90* (2013.01); *C07C 69/618* (2013.01); *C07C 69/738* (2013.01); *C07C 235/74* (2013.01); *C07C 235/78* (2013.01); *C07C 309/65* (2013.01); *C07D 277/44* (2013.01); *C07D 277/46* (2013.01); *C07D 295/192* (2013.01); *C07C 2101/02* (2013.01); *C07C 2101/04* (2013.01); *C07C 2101/08* (2013.01); *C07C 2101/14* (2013.01); *Y10S 514/884* (2013.01)

(58) Field of Classification Search
CPC .... C07C 49/255; C07C 69/618; C07C 235/78; C07C 309/65; C07D 295/192; A61K 31/12; A61K 31/165; A61K 31/255; A61K 31/426
USPC ...... 568/329; 564/169; 514/237.5, 371, 517, 514/621, 683
See application file for complete search history.

(56) References Cited

U.S. PATENT DOCUMENTS

| | | |
|---|---|---|
| 4,806,683 A | 2/1989 | Miyata et al. |
| 5,334,481 A | 8/1994 | Merrem |
| 5,496,556 A | 3/1996 | Johnson |
| 5,609,858 A | 3/1997 | Buck |
| 5,637,310 A | 6/1997 | Johnson |
| 5,733,886 A | 3/1998 | Baroody et al. |
| 5,883,124 A | 3/1999 | Samid |

(Continued)

FOREIGN PATENT DOCUMENTS

| | | |
|---|---|---|
| DE | 2728 242 | 1/1979 |
| EP | 0114003 | 7/1984 |

(Continued)

OTHER PUBLICATIONS

Lin et al. Antitumor agents 247. New 4-ethoxycarbonylethyl curcumin analogs as potential antiandrogenic agents. Bioorganic & Medicinal Chemistry, vol. 14, 2006, 2527-2534.*

(Continued)

*Primary Examiner* — Sikarl Witherspoon

(74) *Attorney, Agent, or Firm* — Cesari and McKenna LLP

(57) ABSTRACT

The present invention relates to compounds having at least one (substituted phenyl)-propenal moiety. The compounds are useful in treating a subject suffering from an androgen receptor-associated medical condition, e.g., inflammation, acne, alopecia, hirsutism, wound, Spinal and Bulbar Muscular Atrophy (SBMA, Kennedy's Disease), unwanted immune response, immune disorder, or cancer.

15 Claims, 19 Drawing Sheets

(56) References Cited

U.S. PATENT DOCUMENTS

| | | | |
|---|---|---|---|
| 5,958,645 | A | 9/1999 | Hirose et al. |
| 6,218,369 | B1 | 4/2001 | Bombardelli et al. |
| 6,790,979 | B2 | 9/2004 | Lee et al. |
| 7,355,081 | B2 | 4/2008 | Lee et al. |
| 8,202,905 | B2 | 6/2012 | Shih et al. |
| 2003/0198990 | A1 | 10/2003 | Chang et al. |
| 2006/0024385 | A1 | 2/2006 | Pedersen |
| 2006/0040875 | A1 | 2/2006 | Oliver |
| 2006/0199768 | A1 | 9/2006 | Singleton |
| 2006/0258752 | A1 | 11/2006 | Vander Jagt et al. |
| 2006/0275516 | A1 | 12/2006 | Ram et al. |
| 2007/0204412 | A1 | 9/2007 | Arkles |
| 2008/0103213 | A1 | 5/2008 | Kurzrock et al. |

FOREIGN PATENT DOCUMENTS

| | | |
|---|---|---|
| JP | 2000-258904 | 9/2000 |
| WO | WO 97/16403 | 5/1997 |
| WO | WO 03/011280 | 2/2003 |
| WO | WO-03/088927 A2 | 10/2003 |
| WO | WO 2005/072462 | 8/2005 |
| WO | WO 2006/029040 | 9/2005 |
| WO | WO-2006/044379 A2 | 4/2006 |
| WO | WO 2007/076162 | 7/2007 |
| WO | WO-2008/085984 A1 | 7/2008 |
| WO | WO-2009/017815 A1 | 2/2009 |

OTHER PUBLICATIONS

Abdullah, et al., "Spinobulbar muscular atrophy: polyglutamine-expanded androgen receptor is proteolytically resistant in vitro and processed abnormally in transfected cells", Human Mol. Genetics, 7(3):379-384, 1998.

Aggarwal, et al., "Curcumin (Diferuloylmethane) Down-Regulates Expression of Cell Proliferation and Antiapoptotic and Metastatic Gene Products through Suppression of IκBα Kinase and Akt Activation", Mol Pharmacol Jan. 2006 69:195-206.

Ashcroft, et al., "Androgen receptor-mediated inhibition of cutaneous wound healing", J. Clin. Investigation, 110(5):615-624, 2002.

Bailey, et al., "Molecular chaperones enhance the degradation of expanded polyglutamine repeat androgen receptor in a cellular model of spinal and bulbar muscular atrophy", Human Mol. Genetics, 11(5):515-523, 2002.

Barkhaus, http://www.emedicine.com/neuro/topic421.htm (last visited Nov. 29, 2005).

Chen, et al., "Molecular determinants of resistance to antiandrogen therapy", Nature Medicine, 10(1):33-39, 2004.

Chung, et al., "Effects of docosahexaenoic acid and eicosapentaenoic acid on androgen-mediated cell growth and gene expression in LNCaP prostate cancer cells", Carcinogenesis, 22(8): 1201-1206, 2001.

Foley, et al., "5 Alpha-reductase inhibitors: what's new?", Current Opinion in Urology, 13:31-37, 2003.

Harper, et al., http://www.emedicine.com/derm/topic2.htm (last visited Nov. 29, 2005).

Heinlein, et al., "Androgen Receptor in Prostate Cancer", Endocrine Reviews, 25(2):276-308, 2004.

Lee, et al., "Endocrine Mechanisms of Disease Expression and Degradation of Androgen Receptor: Mechanisms and Clinical Implications", Journal of Clinical Endocrinology & Metabolism, 88:4043-4045, 2003.

Leibowitz, et al., "Treatment of Localized Prostate Cancer with Intermittent Triple Androgen Blockade: Preliminary Results in 110 Consecutive Patients", The Oncologist, 6:177-182 (2001).

Lin, et al., "Antitumor Agents. 250. Design and Synthesis of New Curucumin Analogues as Potential Anti-Prostate Cancer Agents", Journal of Medicinal Chemistry, 49(13), 3963-3972, 2006.

Lin, et al., "Phosphorylation-dependent ubiquitylation and degradation of androgen receptor by Akt require Mdm2 E3 ligase", The EMBO Journal, 21(15):4037-4048, 2002.

Ma, et al., "Androgen receptor is a new potential therapeutic target for the treatment of hepatocellular carcinoma", Gastroenterology, 135(3):947-955, 2008.

Miyamoto, et al., "Promotion of bladder cancer development and progression by androgen receptor signals", J. Natl. Cancer Inst., 99:558-568, 2007.

Mostad, et al., "Structural Studies of Curcuminoids IV. Crystal Structure of 1,7-Diphenyl-4-butyl-1,6-heptadien-3,5-dione (DPBHDD)", Acta Chemica Scandinavia B 38, 479-484, 1984.

Nam, et al., "Syntheses of Certain 3-Aryl-2-propenoates and Evaluation of their Cytotoxicity", Bioorganic & Medicinal Chemistry Letters 11(2001) 1179-1176.

Neckers, et al., "Heat Shock Protein 90 Inhibition by 17-Allylamino-17-demethoxygeldanamycin: A Novel Therapeutic Approach for Treating Hormone-refractory Prostate Cancer", Clinical Cancer Research, 8:962-966, 2002.

Niu, et al., "Differential androgen receptor signals in different cells explain why androgen-deprivation therapy of prostate cancer fails", Oncogener, 1-12, 2010.

Ohtsu, et al., "Antitumor agents 222. Synthesis and anti-androgen activity of new diarylheptanoids", Bioorganic & Medicinal Chemistry, 11(23), 5083-5090, 2003.

Ohtsu, et al., "Antitumor agents. 217. Curcumin analogues as novel androgen receptor antagonists with potential as anti-prostate cancer agents", J. Med. Chem., 45:5037-5042, 2002.

Okitsu, et al., "Involvement of interleukin-6 and Androgen Receptor Signaling in Pancreatic Cancer", Genes and Cancer I(8).859-867, 2010.

Pedersen, et al., "Synthesis of Naturally Occurring Curcuminoids and Related Compounds", Liebigs Ann. Chem 1557-1569, 1985.

Shih, et al., "A Class II Antigen-Specific T Cell Clone can Suppress Graft-Versus-Host Reactivity in Murine Allogenic Bone Marrow Chimeras", Transplant Proceedings, XIX(1):2664-2667, 1987.

Shih, et al., "Downregulation of L3T4+ Cytotoxic T Lymphocytes by Interleukin-2", Science, 238:344-347, 1987.

Shih, et al., "The acquisition and maintenance of cytolytic activity by CD4 Murine T-Lymphocyte clones", Cellular Immunology, 130, 160-175, 1990.

Singh, et al., "Suppression of advanced human prostate tumor growth in athymic mice by silibinin feeding is associated with reduced cell proliferation, increased apoptosis, and inhibition of angiogenesis", Cancer Epidemiology Biomarkers & Prevention, 12:933-939, 2003.

Solit, et al., "17-Allylamino-17-demethoxygeldanamycin Induced the Degradation of Androgen Receptor and HER-2/neu and Inhibits the Growth of Prostate Cancer Xenografts", Clinical Cancer Research, 8:986-993, 2002.

Supardjan, et al., "Structure and cytotoxicity activity relationship of curcumin derivatives on myeloma cells", Majalah Farmasi Indonesia, 16(2), 100-104, 2005.

Van Baar, et al., "Electron ionization mass spectrometry of curcumin analogs: an olefin metathesis reaction in the fragmentation of radical cations", Journal of Mass Spectrometry, 33(4), 319-327, 1998.

Wang, et al., "Androgens and ovarian cancers", Eur. J. Gynaec. Oncol, XXV(2):157-163, 2004.

Xing, et al., "Quercetin inhibits the expression and function of the androgen receptor in LNCaP prostate cancer cells", Carcinogenesis, 22(3):409-414, 2001.

Yang, et al., "ASC-J9 ameliorates spinal and bulbar muscular atrophy phenotype via degradation of androgen receptor", Nature Medicine, 13(3):348-353, 2007.

Ye, et al., "Effects of topical antiandrogen and 5-alpha-reductase inhibitors on sebaceous glands in male fuzzy rats", Skin Pharmacology, 10:288-297, 1997.

Yeh, et al., "Abnormal Mammary Gland Development and Growth Retardation in Female Mice and MCF7 Breast Cancer Cells Lacking Androgen Receptor", J. Exp. Med., 198(12):1899-1908, 2003.

Zhu, et al., "Silymarin inhibits function of the androgen receptor by reducing nuclear localization of the receptor in the human prostate cancer cell line LNCaP", Carcinogenesis, 22:1399-1403, 2001.

(56) References Cited

OTHER PUBLICATIONS

Kashima et al "The Ring Cleavage of 3,5-Disubstituted Isoxazolium Salts with Alkoxides" Heterocycles: An International Journal for Reviews and Communications in Heterocyclic Chemistry vol. 7, pp. 241-246, 1977.

* cited by examiner

5-Hydroxy-7-(4-hydroxy-3-methoxy-phenyl)-4-
[3-(4-hydroxy-3-methoxy-phenyl)-acryloyl]-hepta-
4,6-dienoic acid ethyl ester
(ASC-J15)

1,7-Bis-(3,4-dimethoxy-phenyl)-5-hydroxy-
hepta-1,4,6-trien-3-one (dimethyl curcumin)
(ASC-J9)

Summary of Select ASC compounds, structures and molecular weights.

| Compound ID | Structure | Formula Molecular weight |
|---|---|---|
| ASC-Q9 | 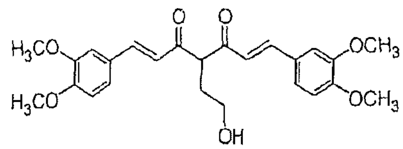 | $C_{25}H_{28}O_7$ 440.49 |
| ASC-Q12 | 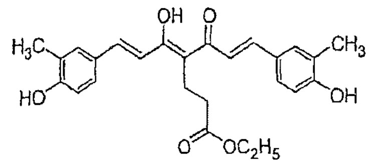 | $C_{26}H_{28}O_6$ 436.50 |
| ASC-Q30 | 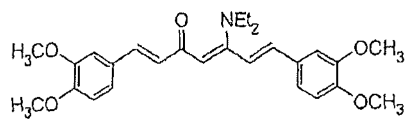 | $C_{27}H_{33}NO_5$ 451.55 |
| ASC-Q35 | 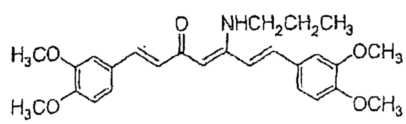 | $C_{26}H_{31}NO_5$ 437.53 |
| ASC-Q44 | 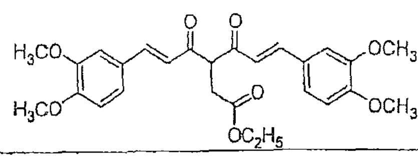 | $C_{27}H_{30}O_8$ 482.52 |
| ASC-Q49 | 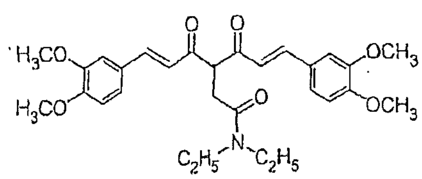 | $C_{29}H_{35}NO_7$ 509.59 |
| ASC-Q50 | 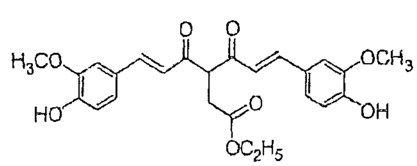 | $C_{25}H_{26}O_8$ 454.47 |

FIG. 2A

| | | |
|---|---|---|
| ASC-Q70 | 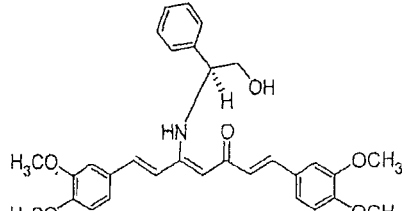 | C₃₁H₃₃NO₆<br>515.60 |
| ASC-Q77 | 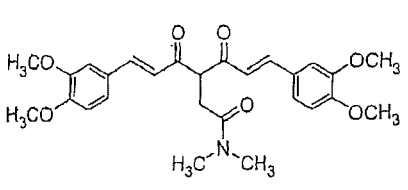 | C₂₇H₃₁NO₇<br>481.54 |
| ASC-Q98 | 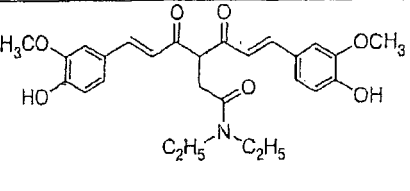 | C₂₇H₃₁NO₇<br>481.54 |
| ASC-Q99 | 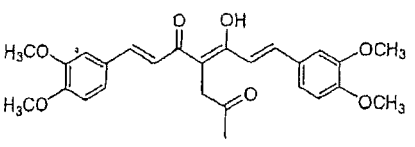 | C₂₆H₂₈O₇<br>452.50 |
| ASC-Q100 | 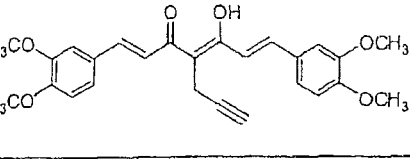 | C₂₆H₂₆O₆<br>434.48 |
| ASC-Q101 | 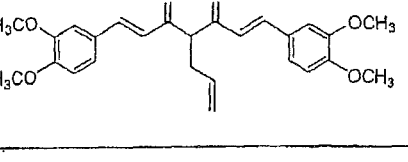 | C₂₆H₂₈O₆<br>436.50 |
| ASC-Q102 | 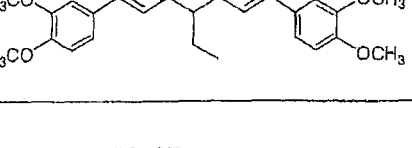 | C₂₅H₂₈O₆<br>424.49 |
FIG. 2B

| Compound | Structure | Formula / MW |
|---|---|---|
| ASC-Q103 | 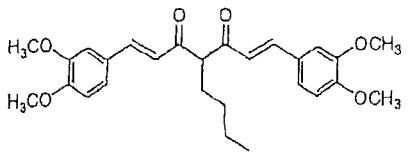 | C₂₇H₃₂O₆<br>452.54 |
| ASC-Q104 | 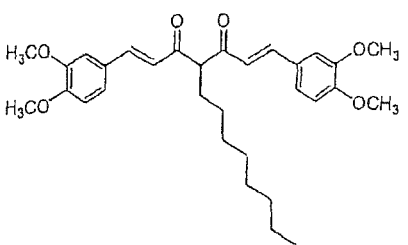 | C₃₁H₄₀O₆<br>508.65 |
| ASC-Q106 | 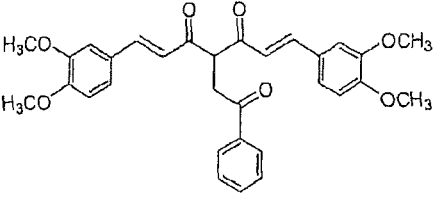 | C₃₁H₃₀O₇<br>514.57 |
| ASC-Q108 | 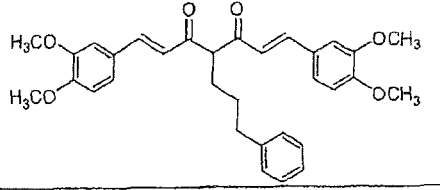 | C₃₂H₃₄O₆<br>514.61 |
| ASC-Q110 | 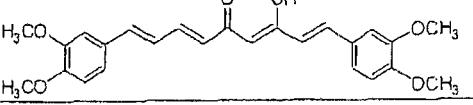 | C₂₅H₂₆O₆<br>422.47 |
| ASC-Q111 | 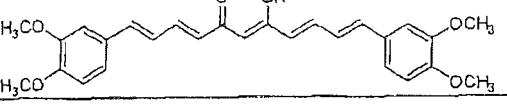 | C₂₇H₂₈O₆<br>448.51 |
| ASC-Q113 | 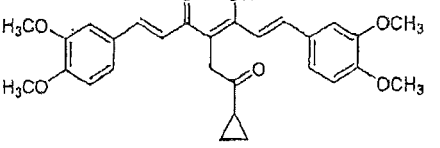 | C₂₈H₃₀O₇<br>478.53 |
FIG. 2C

| Compound | Structure | Formula / MW |
|---|---|---|
| ASC-Q114 | 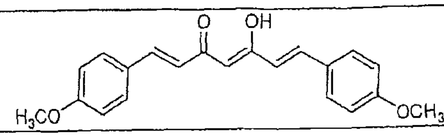 | $C_{21}H_{20}O_4$<br>336.38 |
| ASC-Q115 | 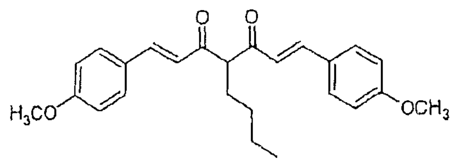 | $C_{25}H_{28}O_4$<br>392.49 |
| ASC-Q116 | 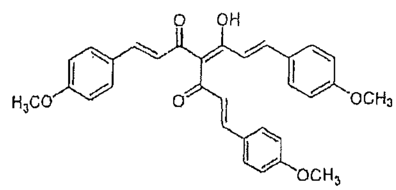 | $C_{31}H_{28}O_6$<br>496.55 |
| ASC-JM1 | 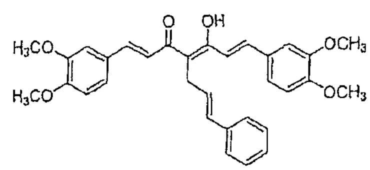 | $C_{32}H_{32}O_6$<br>512.59 |
| ASC-JM2 | 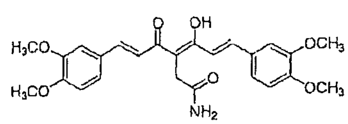 | $C_{25}H_{27}NO_7$<br>453.48 |
| ASC-JM4 | 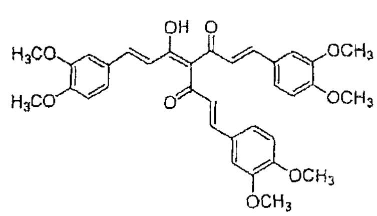 | $C_{34}H_{34}O_9$<br>586.63 |
| ASC-JM5 | 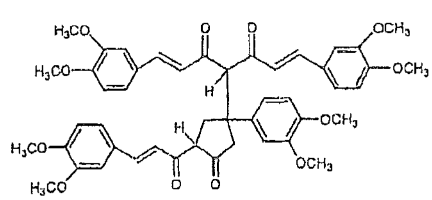 | $C_{47}H_{48}O_{12}$<br>804.87 |

FIG. 2D

| | | |
|---|---|---|
| ASC-JM6 | (structure) | C26H26O8 466.48 |
| ASC-JM7 | (structure) | C32H32O8 544.59 |
| ASC-JM10 | (structure) | C24H24O7 424.44 |
| ASC-JM11 | (structure) | C26H29NO6 451.51 |
| ASC-JM12 | (structure) | C27H30O6 450.52 |
| ASC-JM13 | (structure) | C30H36O6 492.60 |
| ASC-JM14 | (structure) | C26H27F3O6 492.48 |
| ASC-JM16 | (structure) | C26H28O6 436.50 |
| ASC-JM17 | (structure) | C28H32O6 464.55 |

FIG. 2E

| | | |
|---|---|---|
| ASC-JM18 | 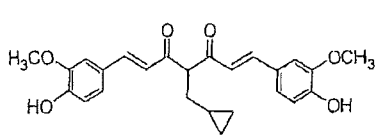 | $C_{25}H_{26}O_6$<br>422.47 |
| ASC-JM19 | 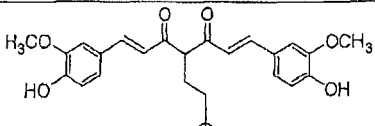 | $C_{24}H_{23}F_3O_6$<br>464.43 |
| ASC-JM20 | 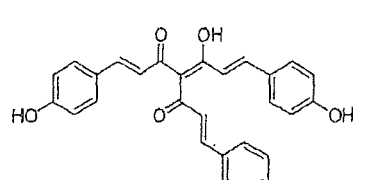 | $C_{28}H_{22}O_6$<br>454.47 |
FIG. 2F

FIG. 3.

| Treatment (concentration) | No. of moiety | 0.1 µM | 0.5 µM | 1.0 µM | 2.5 µM | 5.0 µM | 40.0 µM |
|---|---|---|---|---|---|---|---|
| Monomer-5 | 1 | | | | | 0 | 37 |
| ASC-J9 | 2 | | | | 0 | 43 | |
| ASC-JM4 | 3 | 0 | 68 | 90 | | | |
| ASC-JM5 | 4 | | 28 | 54 | 87 | 86 | |
| ASC-JM7 | 3 | 0 | 0 | 81 | | | |

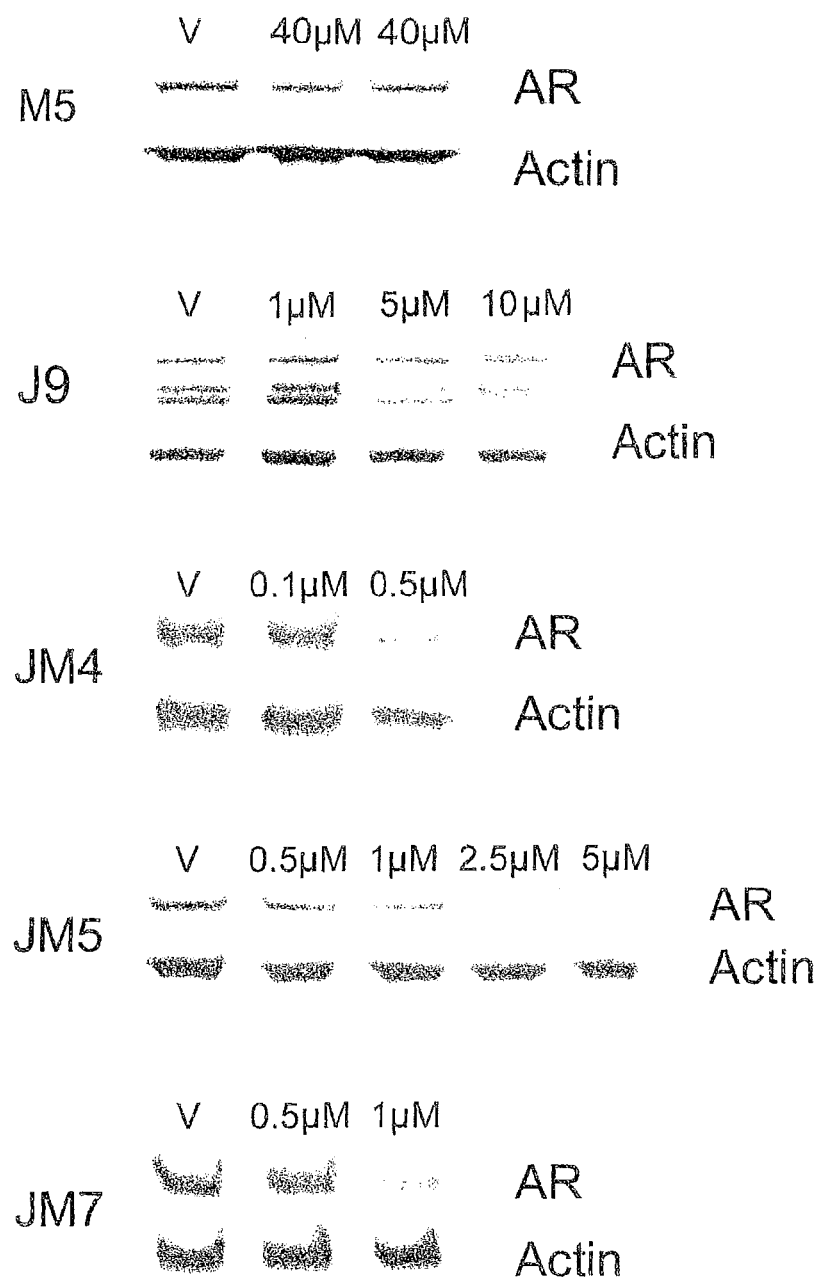
FIG. 4. Representative ASC compounds reduce AR protein expression.

FIG. 5. Representative ASC compounds inhibit prostate cancer cells (LNCaP and CWR22Rv1) growth *in vitro*.

| Compound | Inhibition of AR/DHT mediated cell growth | |
|---|---|---|
| | LNCaP | CWR22rv1 |
| ASC-Q8 | +++ | |
| ASC-Q9 | +++ | |
| ASC-Q12 | ++ | |
| ASC-Q30 | +++ | |
| ASC-Q35 | ++ | |
| ASC-Q44 | ++ | |
| ASC-Q49 | ++ | |
| ASC-Q50 | ++ | |
| ASC-Q70 | + | |
| ASC-JM1 | ++ | |
| ASC-JM4 | ++++ | |
| ASC-JM5 | ++++ | |
| ASC-JM6 | ++ | |
| Monomer-1 | | + |
| Monomer-5 | | ++ |

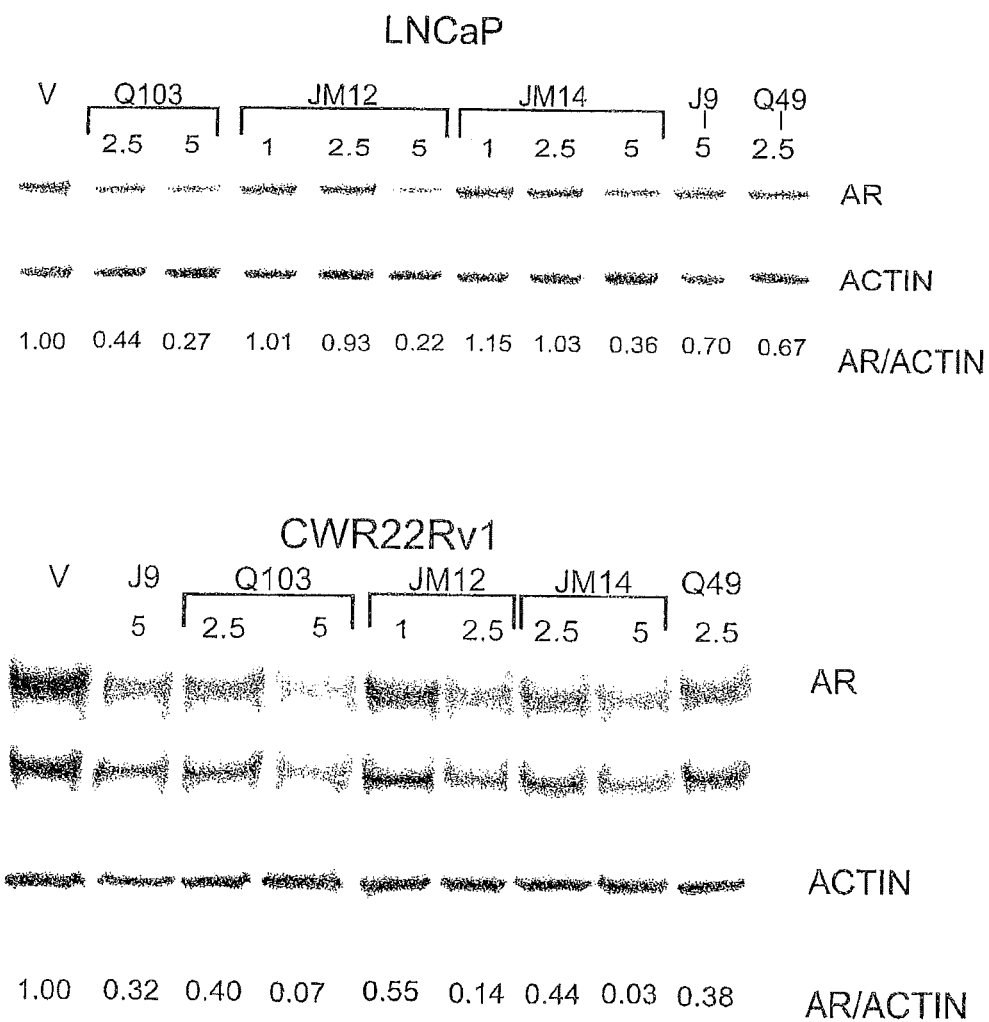
FIG. 6. ASC-Q49, ASC-Q103, ASC-JM12, and ASC-JM4 compounds reduce AR protein expression in LNCaP and CWR22Rv1 cancer cells.

FIG. 7. ASC-J9 and ASC-JM5 enhance AR protein degradation in the presence of cycloheximide in LNCaP cells.
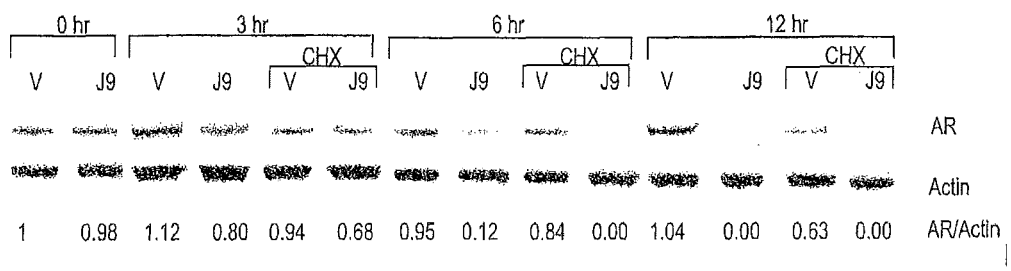
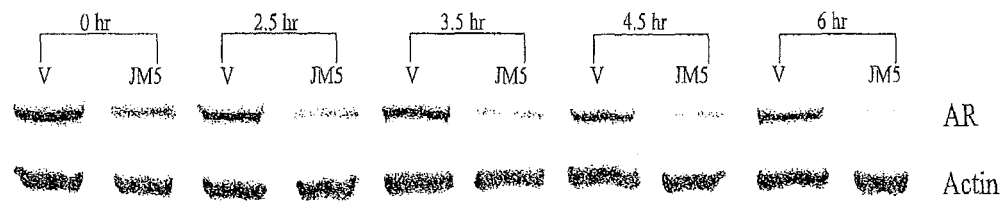

FIG. 8. Representative ASC compounds reduce AR protein expression (% reduction) in LNCaP and CWR22Rv1 cells.

Tested in LNCaP cells

| Treatment | 1 µM | 2.5 µM | 5 µM | 7.5 µM | 20 µM | 40 µM | Potency |
|---|---|---|---|---|---|---|---|
| ASC-Q101 |  | 4 | 47 |  |  |  | ++ |
| ASC-Q102 | 0 | 15 | cell death |  |  |  | +++ |
| ASC-Q103 | 0 | 48 | 73 |  |  |  | ++++ |
| ASC-Q104 |  |  | 27 | 56 |  |  | ++ |
| ASC-Q106 |  | 0 | 6 | 52 |  |  | + |
| ASC-Q108 |  | 0 | 14 | 49 |  |  | + |
| ASC-Q110 | 0 | 0* | 58 | cell death |  |  | ++ |
| ASC-Q111 |  |  | 50 | 62 |  |  | ++ |
| ASC-Q113 | 0 | 11 | cell death |  |  |  | +++ |
| ASC-Q116 |  | 0 | 30 | 68 |  |  | ++ |
| ASC-JM12 | 5 | 22 | 81 |  |  |  | ++++ |
| ASC-JM13 |  | 0 | 43 | 76 |  |  | ++ |
| ASC-JM14 | 0 | 21 | 74 |  |  |  | ++++ |

Tested in CWR22Rv1 cells

| Treatment | 1 µM | 2.5 µM | 5 µM | 7.5 µM | 20 µM | 40 µM | Potency |
|---|---|---|---|---|---|---|---|
| ASC-Q101 |  | 0 | 53 |  |  |  | ++ |
| ASC-Q103 | 8 | 49 | 93 |  |  |  | ++++ |
| ASC-Q113 | 0 | 28 | cell death |  |  |  | +++ |
| ASC-Q116 |  | 77 | cell death |  |  |  | ++++ |
| ASC-JM12 | 36 | 71 |  |  |  |  | ++++ |
| ASC-JM13 |  | 15 | 40 | 87 |  |  | ++ |
| ASC-JM14 | 0 | 43 | 95 |  |  |  | ++++ |

FIG. 9. Tautomers of ASC-JM17 and ASC-Q49
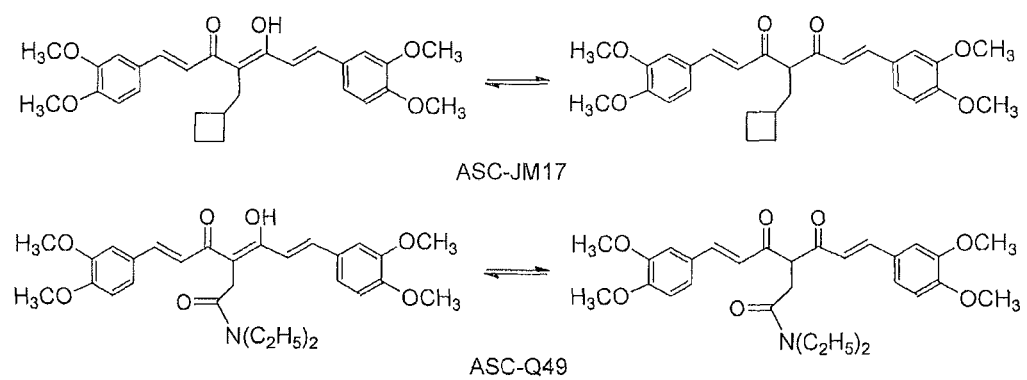
ASC-JM17
ASC-Q49

FIG. 10A.

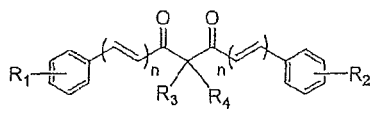

| Compound ID | R₁ | R₂ | R₃ | R₄ | n | formula |
|---|---|---|---|---|---|---|
| 1 | 3'4'-OCH₃ | 3'4'-OCH₃ | CH₂-▷ | CH₃ | 1 | $C_{28}H_{32}O_6$ 464.55 |
| 2 | 3'4'-OCH₃ | 3'4'-OCH₃ | CH₂-□ | CH₃ | 1 | $C_{29}H_{34}O_6$ 478.5767 |
| 3 | 3'4'-OCH₃ | 3'4'-OCH₃ | CH₂-⬠ | H | 1 | $C_{29}H_{34}O_6$ 478.58 |
| 4 | 3'4'-OCH₃ | 3'4'-OCH₃ | CH₂-⬠ | CH₃ | 1 | $C_{30}H_{36}O_6$ 492.60 |
| 5 | 3'4'-OCH₃ | 3'4'-OCH₃ | CH₂-⬡ | CH₃ | 1 | $C_{31}H_{38}O_6$ 506.63 |
| 6 | 3'4'-OCH₃ | 3'4'-OCH₃ | CH₂-C(O)-N(C₂H₅)₂ | CH₃ | 1 | $C_{30}H_{37}NO_7$ 523.62 |
| 7 | 3'4'-OCH₃ | 3'4'-OCH₃ | CH₂-C(O)-N(CH₃)₂ | CH₃ | 1 | $C_{28}H_{33}NO_7$ 495.56 |
| 8 | 3'4'-OCH₃ | 3'4'-OCH₃ | (CH₂)₃CH₃ | CH₃ | 1 | $C_{28}H_{34}O_6$ 466.57 |
| 9 | 3'4'-OCH₃ | 3'4'-OCH₃ | CH₂-C(O)-morpholine | H | 1 | $C_{29}H_{33}NO_8$ 523.57 |
| 10 | 3'4'-OCH₃ | 3'4'-OCH₃ | CH₂-C(O)-NH-thiazole | H | 1 | $C_{28}H_{28}N_2O_7S$ 536.60 |
| 11 | 3'4'-CH₃ | 3'4'-CH₃ | CH₂-C(O)-morpholine | CH₃ | 1 | $C_{30}H_{35}NO_8$ 537.60 |
| 12 | 3'4'-OCH₃ | 3'4'-OCH₃ | CH₂-C(O)-NH-thiazole | CH₃ | 1 | $C_{29}H_{30}N_2O_7S$ 550.62 |
| 13 | 3'4'-OCH₃ | 3'4'-OCH₃ | CH₂-▷ | F | 1 | $C_{27}H_{29}FO_6$ 468.51 |
| 14 | 3'4'-OOCH₃ | 3'4'-OCH₃ | CH₂-□ | F | 1 | $C_{28}H_{31}FO_6$ 482.54 |
| 15 | 3'4'-OCH₃ | 3'4'-OCH₃ | CH₂-⬠ | F | 1 | $C_{29}H_{33}FO_6$ 496.57 |

| 16 | 3'4'-OCH₃ | 3'4'-OCH₃ | CH₂-cyclohexyl | F | 1 | $C_{30}H_{35}FO_6$ 510.59 |
|---|---|---|---|---|---|---|
| 17 | 3'4'-OCH₃ | 3'4'-OCH₃ | CH₂-C(O)-N(C₂H₅)₂ | F | 1 | $C_{29}H_{34}FNO_7$ 527.58 |
| 18 | 3'4'-OCH₃ | 3'4'-OCH₃ | CH₂-C(O)-N(CH₃)₂ | F | 1 | $C_{27}H_{30}FNO_7$ 499.53 |
| 19 | 3'4'-OCH₃ | 3'4'-OCH₃ | (CH₂)₃CH₃ | F | 1 | $C_{27}H_{31}FO_6$ 470.53 |
| 20 | 3'4'-OCH₃ | 3'4'-OCH₃ | CH₂-C(O)-N(C₂H₅)₂ | Cl | 1 | $C_{29}H_{34}ClNO_7$ 544.04 |
| 21 | 3'4'-OCH₃ | 3'4'-OCH₃ | CH₂-C(O)-N(CH₃)₂ | Cl | 1 | $C_{27}H_{30}ClNO_7$ 515.98 |
| 22 | 3'4'-OCH₃ | 3'4'-OCH₃ | CH₂CH₂COOC₂H₅ | CH₃ | 1 | $C_{29}H_{34}O_8$ 510.58 |
| 23 | 3'4'-OCH₃ | 3'4'-OCH₃ | CH₂CH₂COOC₂H₅ | F | 1 | $C_{28}H_{31}FO_8$ 514.54 |
| 24 | 3'4'-OCH₃ | 3'4'-OCH₃ | CH₂CH₂COOH | CH₃ | 1 | $C_{27}H_{30}O_8$ 482.52 |
| 25 | 3'4'-OCH₃ | 3'4'-OCH₃ | CH₂CH₂COOH | F | 1 | $C_{26}H_{27}FO_8$ 486.49 |
| 26 | 3'OCH₃,4'OH | 3'OCH₃,4'OH | CH₂CH₂COOC₂H₅ | CH₃ | 1 | $C_{27}H_{30}O_8$ 482.52 |
| 27 | 3'OCH₃,4'OH | 3'OCH₃,4'OH | CH₂CH₂COOC₂H₅ | F | 1 | $C_{26}H_{27}FO_8$ 486.49 |
| 28 | 3'-OCH₃ | 3'-OCH₃ | CH₂-cyclopropyl | CH₃ | | $C_{27}H_{30}O_4$ 418.52 |
| 29 | 3'-OH | 3'-OH | CH₂-cyclopropyl | CH₃ | 1 | $C_{25}H_{26}O_4$ 390.47 |
| 30 | 3'-OCH₃ | 3'-OSO₂C₂H₅ | CH₂-cyclopropyl | CH₃ | 1 | $C_{28}H_{32}O_6S$ 496.62 |
| 31 | 3'-OSO₂C₂H₅ | 3'-OSO₂C₂H₅ | CH₂-cyclopropyl | CH₃ | 1 | $C_{29}H_{34}O_8S_2$ 574.71 |
| 32 | 3'4'-OCH₃ | 3'4'-OCH₃ | CH₂-C(O)-N(C₂H₅)₂ | CH₃ | 2 | $C_{34}H_{41}NO_7$ 575.69 |
| 33 | 3'4'-OCH₃ | 3'4'-OCH₃ | CH₂-cyclopropyl | F | 2 | $C_{32}H_{35}FO_6$ 534.62 |

FIG. 10B

COMPOUNDS WITH (1E, 6E)-1,7-BIS-(3,4-DIMETHOXYPHENYL)-4-4-DISTRIBUTED-HEPTA-1,6-DIENE-3,5-DIONE STRUCTURAL SCAFFOLD, THEIR BIOLOGICAL ACTIVITY, AND USES THEREOF

CROSS-REFERENCE TO RELATED APPLICATIONS

The present application is a Continuation of U.S. application Ser. No. 14/622,883, filed on Feb. 15, 2015, which is a Continuation of U.S. application Ser. No. 13/920,199, filed on Jun. 18, 2013, which is a Continuation-in-Part of U.S. application Ser. No. 13/525,941, filed Jun. 18, 2012, which is a Continuation-in-Part of U.S. application Ser. No. 12/800,251, filed May 11, 2010, which is a Divisional of U.S. application Ser. No. 12/008,124, filed Jan. 8, 2008, which claims benefit of priority to U.S. Application No. 60/879,458 filed on Jan. 8, 2007, each of which is incorporated by reference herein in its entirety.

The present application is also a Continuation of U.S. application Ser. No. 14/622,883, filed on Feb. 15, 2015, which is Continuation of U.S. application Ser. No. 13/920, 199, filed on Jun. 18, 2013, which is also a Continuation-in-Part of U.S. application Ser. No. 13/525,941, filed Jun. 18, 2012, which is a Continuation-in-Part of U.S. application Ser. No. 12/008,124, filed Jan. 8, 2008, which claims benefit of priority to U.S. Application No. 60/879,458 filed on Jan. 8, 2007, each of which is incorporated by reference herein in its entirety.

BACKGROUND

Technical Field

The present invention relates to compounds with biological activity and pharmaceutical and cosmetic formulations thereof, their derivatives and methods of use, more specifically the present invention includes compounds with at least one (substituted phenyl)-propenal moiety and their biological activity and use thereof. The present invention also relates to compounds with (1E, 6E)-1,7-bis-(3,4-dimethoxyphenyl)-4,4-disubstituted-hepta-1,6-diene-3,5-dione structural scaffold and their biological activity and uses thereof.

Background Information

It is well known that certain natural products may possess therapeutic effects, which has led to their use in the treatment and prevention of human diseases across many cultures (e.g., Chinese herbal medicines and many other folk medicines). The effectiveness of such treatments has lead the pharmaceutical industry to seek and isolate active compounds from these natural products and develop the active ingredients as therapeutic or prophylactic drugs for the treatment and prevention of a variety of diseases or medical conditions. Thus many commonly used pharmaceuticals have been developed or have arisen from natural products. Among these include, aspirin (acetylsalicylic acid), which was isolated from bark of the willow tree; ephedrine and pseudoephedrine, which were isolated from a Chinese herb Ma Huang; and penicillin, which was isolated from fungus (*Pennicillium chrysogenum*). However, compounds isolated from natural products are known to play certain physiological function(s) in its native host; whereas their therapeutic effects against human diseases are not readily apparent. Historically, such therapeutic treatments were derived merely by accumulated experiences or "trial and error" in humans. Moreover, because such compounds were not initially created for use in humans, the compounds in their native form are frequently not in the most optimal form, both in structure as well as efficacy, to treat human diseases. However, today's modern chemistry technology, including analytical and synthetic chemistries, together with the advances in medicinal biology have made it possible for one to dissect a chemical structure and localize a "phatinacophore" (a core structure that is essential for the therapeutic activity) within a compound such as one isolated from a natural product; furthermore, these new techniques allow one to synthesize new compounds, based on the structure of a pharmacophore, that possess optimal or even better therapeutic efficacy.

In this invention we have demonstrated that a compound with a single (4-hydroxy-3-methoxy-phenyl)-propenal moiety possesses an activity that could reduce the expression of androgen receptor (AR) protein by enhancing its degradation. This discovery resulted in part from our extensive study of compound ASC-J9 (1,7-Bis-(3,4-dimethoxy-phenyl)-5-hydroxy-hepta-1,4,6-trien-3-one), a dimethylated form of a natural compound curcumin (existing as a major pigment in a turmeric plant). Compound curcumin and many of its analogs have been reported to possess numerous biological activities in vitro, such as, anti-oxidant, anti-inflammatory, anti-tumor, and antiangiogenesis activities; but neither curcumin nor its analogues have been developed into a therapeutic drug to treat human diseases. This indicates curcumin in its native form is probably not an optimal molecule for development into a therapeutic drug.

Previously we have discovered compounds ASC-J9 and ASC-J15 (5-Hydroxy-7-(4-hydroxy-3-methoxy-phenyl)-4-[3-(4-hydroxy-3-methoxy-phenyl)-acryloyl]-hepta-4,6-dienoic acid ethyl ester) (FIG. 1), both possess potent prostate cancer inhibitory and anti-androgenic activity. These two compounds, in our hand, also exhibited more potent anti-prostate cancer activity than a current therapeutic drug hydroxyl flutamide (HF), a class of "non-steroid anti-androgen" drug that is widely used to treat human prostate cancer.

After extensive further study of the structure and bioactivity of ASC-J9 and ASC-J15, we were surprised to find that the (substituted phenyl)-propenal moieties shared by these two compounds are actually the core structure(s) that attribute to the potent anti-androgen/AR activity of these compounds but not the entire curcumin-like structure. Based in part on this finding we have generated, by chemically synthesis, numerous new compounds, including compounds that possess one, two, three or four (substituted phenyl)-propenal moieties to further support the concept that a (substituted phenyl)-propenal moiety is the pharmacophore of these compounds. Results from our study are able to show that the increase in number of these moieties within a compound structure may alter or may increase the anti-androgen/AR activity of the compound. We also demonstrate herein that anti-androgenic activity is present within compounds having a single (substituted phenyl)-propenal moiety. New derivatives, based on our new compounds with at least one (substituted phenyl)-propenal moiety, were also synthesized by the present inventors to elucidate not only the pharmacophore structure but also to evaluate the anti-androgenic and anti-cancer activities. The new compounds, provided herein by the inventors further show significant improvements and optimization of bioactivity, bioavailability, water solubility and other criteria essential for the development of therapeutic drug.

SUMMARY

The present invention provides biologically active compounds having at least one (substituted phenyl)-propenal moiety. Thus it is an object of the present invention to provide compounds having at least one (substituted phenyl)-propenal moiety for use as a treatment for a medical condition, such as a human medical condition.

In one aspect of the present invention a compound having at least one (substituted phenyl)-propenal moiety is provided, the compound having the formula according to formula I:

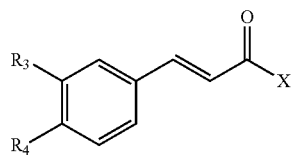

(I)

wherein 1) $R_3$ and $R_4$ are each independently selected from the group consisting of alkoxy, hydroxy, and hydrogen; and 2) X is selected from the group consisting of hydroxy, alkoxy, ethyl propionate, ethyl methyl carbonate, and carbonyl alkyl. In some embodiments the compound has formula selected from the group consisting of monomers 1, 3, 5, 6 and 7. These monomers are provided below:

Monomers:

Monomer-1

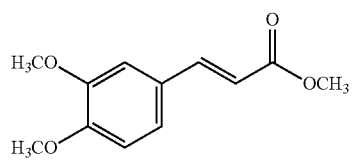

Monomer-3

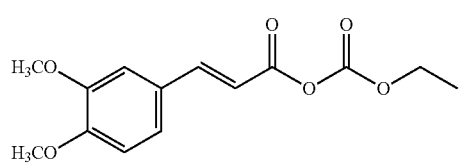

Monomer-5

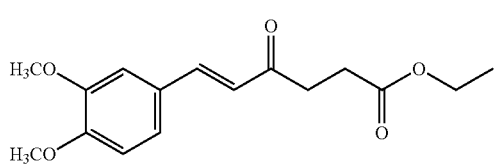

Monomer-6

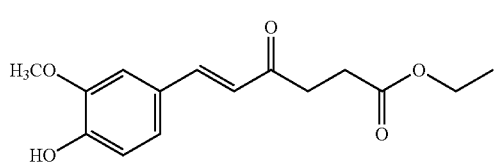

Monomer-7

In another aspect of the present invention a compound is provided including a (substituted phenyl)-propenal moiety having the formula according to (IIa) or (IIb):

IIa

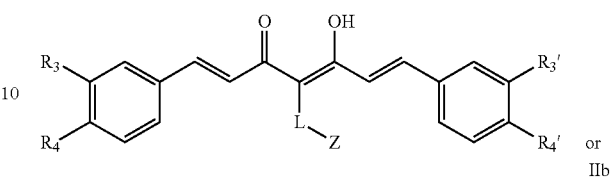

or

IIb

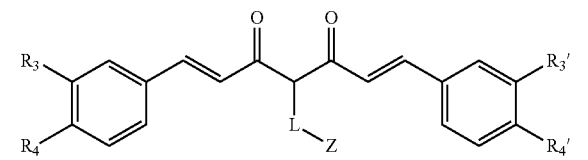

wherein: 1) $R_3$, $R_4$, $R_3'$, and $R_4'$ are independently selected from the group consisting of —H, —OH, and —OCH$_3$; 2) L is a C0-C8 alkylene or L is an unsaturated alkenylene or alkynl when Z is nothing; 3) Z is selected from the group consisting of —H, —OH, an aromatic ring, a cycloalkyl, —COR$_1$, —CO$_2$R$_1$, —CONR$_1$R$_2$, —NR$_1$R$_2$, —CX$_3$, wherein $R_1$ and $R_2$ are independently selected from the group consisting of —H, —CH$_3$, and —C$_2$H$_5$; and 4) X is a halogen atom selected from the group consisting of —F, —Cl, and —Br. The formula IIa and IIb are the equilibrate tautomers as a common phenomenon of diketone (see, for example, FIG. 9). In some embodiments the compound is selected from the group consisting of II-1, II-2, II-3, II-4 and II-5. The formulas provided as:

II-1

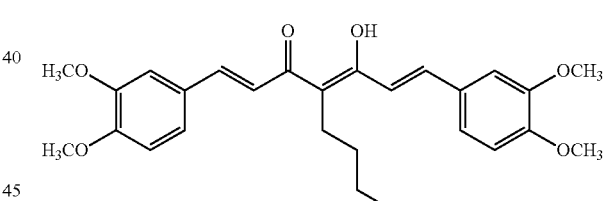

II-2

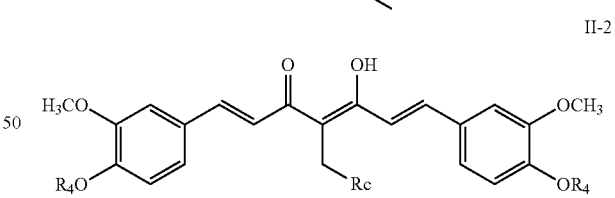

$R_4$ = H, CH$_3$,

Rc = 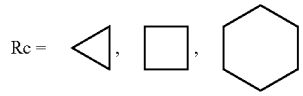

II-3

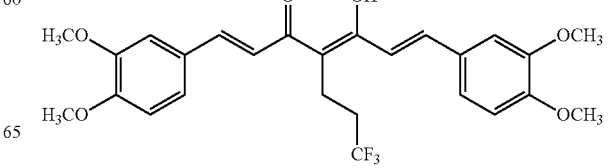
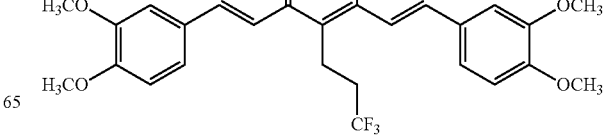

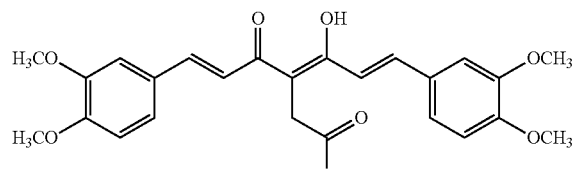

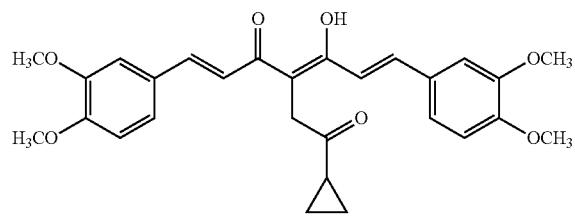

In another aspect of the present invention, a compound is provided according to formula IIc:

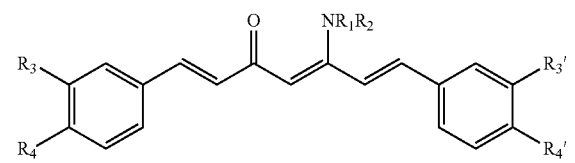

wherein 1) $R_3$, $R_4$, $R_3'$, and $R_4'$ are independently selected from the group consisting of —H, —OH, and —OCH$_3$; and 2) $R_1$, and $R_2$ are independently selected from the group consisting of —H, —CH$_3$, —C$_2$H$_5$, a substituted aryl and a substituted benzyl group.

In another aspect of the present invention, a compound is provided according to formula III:

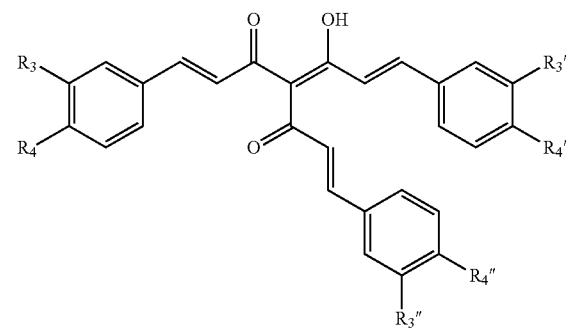

wherein $R_3$, $R_4$, $R_3'$, $R_4'$, $R_3''$, and $R_4''$ are each independently selected from the group consisting of alkoxy, hydroxy, and hydrogen. In some embodiments, the compound includes the formula III-1 or III-2, which is provided as:

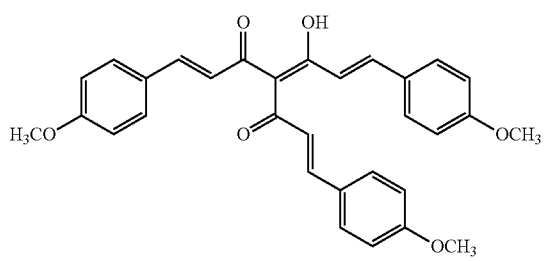

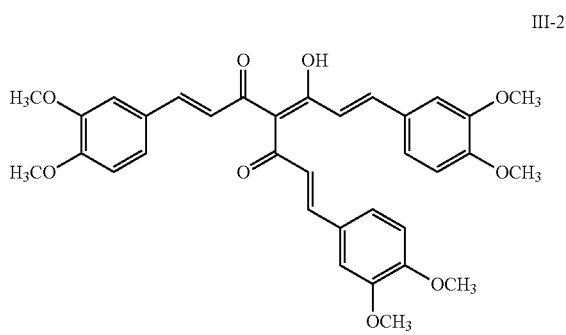

In another aspect of the present invention, a compound is provided according to the formula IV:

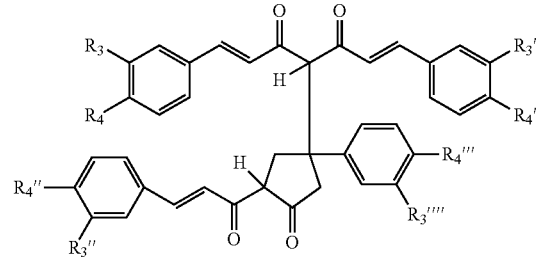

wherein $R_3$, $R_4$, $R_3'$, $R_4'$, $R_3''$, $R_4''$, $R_3'''$, and $R_4'''$ are each independently selected from the group consisting of alkoxy, hydroxy, and hydrogen. In some embodiments the compound includes the formula IV-1:

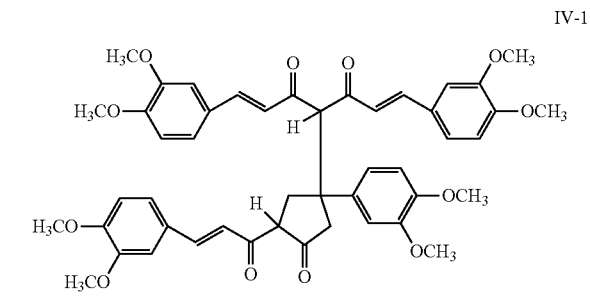 [SMILES: COc1ccc(/C=C/C(=O)C2CC(c3ccc(OC)c(OC)c3)(C(C(=O)/C=C/c3ccc(OC)c(OC)c3)C(=O)/C=C/c3ccc(OC)c(OC)c3)CC2=O)cc1OC]

In another aspect of the present invention a compound is provided according to formula V:

V

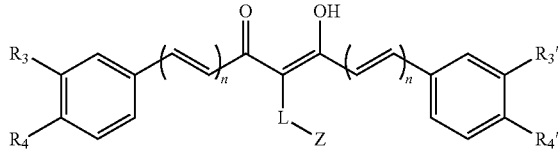

wherein 1) each "n" is independently 1, 2, or 3; 2) $R_3$, $R_4$, $R_3'$, and $R_4'$ are independently selected from the group consisting of —H, —OH, and —OCH$_3$; 3) L-Z side chain can be no-exist, but if L-Z side chain exists, L is a C0-C8 alkylene, or an unsaturated alkenylene or alkynl when Z is nothing; 4) Z is selected from the group consisting of —H, —OH, an aromatic ring, a cycloalkyl, —CO$_2$R$_1$, —CONR$_1$R$_2$, —NR$_1$R$_2$, —CX$_3$; 5) R$_1$ and R$_2$ are independently selected from the group consisting of —H, —CH$_3$, and —C$_2$H$_5$; and 6) X is a halogen atom selected from the group consisting of —F, —Cl, and —Br. In some embodiments the compound is provided according to formula V-1 or V-2:

V-1

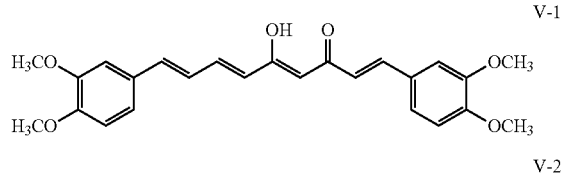

V-2

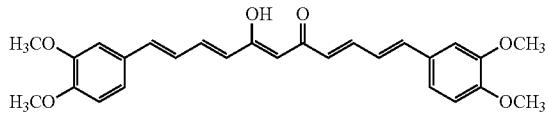

The present invention also provides biologically active compounds having a structure scaffold of 4,4-disubstituted 1,7-bis-(3,4-dimethoxyphenyl)-hepta-1,6-diene-3,5-dione. Thus, it is an object of the present invention to provide compounds having two proper substations at C4 position of 1,7-bis-(3,4-dimethoxyphenyl)-hepta-1,6-diene-3,5-dione structure for use as a treatment for a medical conditions, such as but not limited to, human medical conditions.

In one aspect of the present invention a compound having a 4,4-disubstituted 1,7-bis-(3,4-dimethoxyphenyl)-hepta-1,6-diene-3,5-dione structural scaffold is provided, the compound having the formula according to formula VI, or a compound having a structural scaffold 6,6-disubstituted 1,11-bis(substituted phenyl)-undeca-1,3,8,10-tetraene-5,7-dione as the formula according to formula VII:

VI

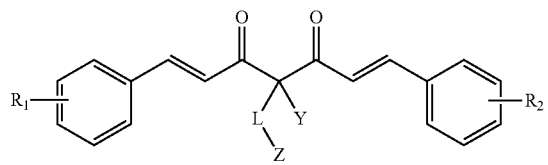

VII

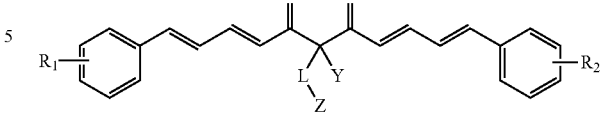

Wherein $R_1$ and $R_2$ are mono- or di-substituted groups, such as a methoxy group (—OCH$_3$), a hydroxyl group (—OH), or an alkyl sulfonyl group, such as —OSO$_2$C$_2$H$_5$; $R_1$ and $R_2$ could be the same or different;

L is a carbonyl, alkylene, alkenylene, or alkynl when Z is not present;

Z is —H, —OH, a substituted styrenyl, an aromatic ring, a cycloalkyl, —COR$_3$, —CONR$_3$R$_4$, or —CX$_3$, wherein R$_3$ and R$_4$ are each —H, —CH$_3$, or —C$_n$H$_{2n+1}$)=2-4), or a heterocyclic, or a heteroaryl moiety, or R$_3$ and R$_4$ together to form a heterocyclic ring, such as a morphorine; or Z is COOR, wherein R is —H, —CH$_3$, —C$_n$H$_{2n+1}$, (n=2-4), or a cycloalkyl, when Y is not H;

X is —F, —Cl, or —Br;

Y is H when L is an alkylene, such as —CH$_2$, and Z is —CONR$_3$R$_4$, R$_3$ and R$_4$ are each —H and a hetercyclic or a heteroaryl, or a cycloalkyl, such as a cyclopentanyl; or Y is a short alkyl (C1-3), such as a methyl (—CH$_3$), or —F, Cl, Br.

In another aspect of the present invention, the compound is selected from the group consisting of C4-R$_3$R$_4$. The formulas provided as:

VIII

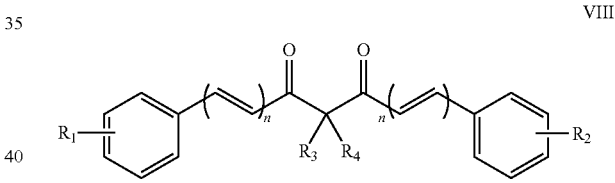

The R$_1$, R$_2$, R$_3$, or R$_4$ represent a series of function groups as listed in the FIG. 10.

In another aspect of the present invention a pharmaceutical formulation or cosmetic formulation is disclosed including a compound including at least one (substituted phenyl)-propenal moiety as provided in the present application and having a desired biological activity. The pharmaceutical formulation or cosmetic formulation may provide a compound of the present invention and a pharmaceutically acceptable carrier or a cosmetically acceptable carrier. In various nonlimiting embodiments, the compound may include monomer 1, 3, 5, 6 or 7 alone or in combination. In further embodiments, the compound includes the formula according to formulas I, II, III, IV, V, or a combination thereof. Thus the compound may include at least one, two, three, four, five or more (substituted phenyl)-propenal moieties.

In another aspect of the present invention a pharmaceutical formulation or cosmetic formulation is disclosed including a compound with a structure of 4,4-disubstituted 1,7-bis-(substituted phenyl)-hepta-1,6-diene-3,5-dione or 6,6-disubstituted 1,11-bis(substituted phenyl)-undeca-1,3,8, 10-tetraene-5,7-dione as provided in the present application and having a desired biological activity. The pharmaceutical formulation or cosmetic formulation can provide a compound of the present invention and a pharmaceutically acceptable carrier or a cosmetically acceptable carrier. In various non-limiting examples, the compound includes the formula according to formula VI or formula VII or formula VIII, or a combination thereof.

In another aspect of the present invention a method of treating a medical condition is disclosed including administering a compound including at least one (substituted phenyl)-propenal moiety having a desired or suspected of having a desired biological activity to an individual in need thereof. The compound may be any disclosed herein alone or in combination. The compounds of the present invention may be used to treat, prevent or ameliorate symptoms from androgen associated disorders. Non-limiting examples of medical conditions that may be treated with the disclosed compounds are androgen associated inflammation including a wound (the compounds assist with wound healing), acne, rheumatoid arthritis, psoriasis, rosacea, and alopecia; Kennedy's disease (spinal and bulbar muscular atrophy, or SBMA), polyglutamine-mediated motor neuron degeneration; cancers such as prostate cancer, bladder cancer, breast cancer, ovarian cancer, hepatocellular (liver) cancer, and pancreatic cancer; and other medical conditions described herein. Treatment of such medical conditions includes administering to an individual suffering from a medical condition describe herein, a therapeutically effective amount of any of the disclosed compounds, their derivatives, or pharmaceutical compositions thereof.

In another aspect of the present invention, a method of treating a medical condition is disclosed including administering a compound including 4,4-disubstituted 1,7-bis-(3, 4-substituted phenyl)-hepta-1,6-diene-3,5-dione or 6,6-disubstituted 1,11-bis(substituted phenyl)-undeca-1,3,8,10-tetraene-5,7-dione structural scaffold having a desired biological activity to an individual in need thereof. The compound may be any disclosed herein alone or in combination. The compounds of the present invention may be used to treat, prevent or ameliorate symptoms from androgen and androgen receptor (AR) associated disorders. Non-limiting examples of medical conditions that can be treated with the disclosed compounds are androgen associated inflammation including a wound (the compounds assist with wound healing), acne, rheumatoid arthritis, psoriasis, rosacea, and alopecia; Kennedy's Disease, (spinal and bulbar muscular atrophy, or SBMA), polyglutamine-mediated motor neuron degeneration; cancers such as prostate cancer, bladder cancer, breast cancer, ovarian cancer, hepatocellular (liver) cancer, and pancreatic cancer; and other medical conditions described herein. Treatment of such medical conditions includes administering to an individual suffering from a medical condition, including but not limited to describe herein, a therapeutically effective amount of any of the disclosed compounds, their derivatives, or pharmaceutical compositions thereof.

BRIEF DESCRIPTION OF THE DRAWINGS

FIG. 2A, FIG. 2B, FIG. 2C, FIG. 2D, FIG. 2E and FIG. 2F. depict a table including a nonlimiting listing of newly synthesized compounds encompassed by the present invention including at least one (substituted phenyl)-propenal moiety, with their structures, chemical formulas and molecular weights.

FIG. 3 depicts a table of Western Blot densitometric data showing compounds having different number of (4-hydroxy-3-methoxy-phenyl)-propenal moieties are capable of reducing Androgen Receptor (AR) expression in human prostate cancer CWR22Rv1 cells.

FIG. 4 depicts Western Blot images showing newly provided compounds with at least one (4-hydroxy-3-methoxy-phenyl)-propenal moiety are capable of reducing Androgen Receptor (AR) protein expression in human prostate cancer CWR22Rv1 cells.

FIG. 5 depicts a table showing some selected ASC compounds and monomers are capable of inhibiting proliferation of human prostate cancer cells (LNCaP and CWR22Rv1) stimulated by DHT in vitro.

FIG. 6 depicts Western Blot data showing four compounds ASC-Q49, ASC-Q103, ASC-JM12, and ASC-JM4, at various concentrations, are capable of reducing endogenous AR expression in LNCaP and CWR22Rv1 human prostate cancer cells.

FIG. 7 depicts Western Blot data showing compounds ASC-J9 and ASC-JM5 enhances AR protein degradation in the presence of a protein synthesis inhibitor, cycloheximide (CHX), tested in LNCaP cells.

FIG. 8 depicts two tables (8a and 8b) that summarize the potency of representative ASC compounds in reducing endogenous AR protein expression (using Western Blot analysis) at various concentrations, when tested in LNCaP and CWR22Rv1 human prostate cancer cells.

FIG. 9 depicts a structural representation of compounds ASC-JM17 and ASC-Q49 as an equilibrium of enol-ketone and diketone tautomers which have anti-androgenic and anti-AR activities.

FIG. 10A and FIG. 10B depict a table including a nonlimiting listing of compounds encompassed by the present invention including 4,4-disubstituted 1,7-bis-(substituted phenyl)-hepta-1,6-diene-3,5-dione and 6,6-disubstituted 1,11-bis(substituted phenyl)-undeca-1,3,8,10-tetraene-5,7-dione scaffold, with their structures, chemical formulas, and molecular weights.

DETAILED DESCRIPTION

A. Definitions

Figure 1:
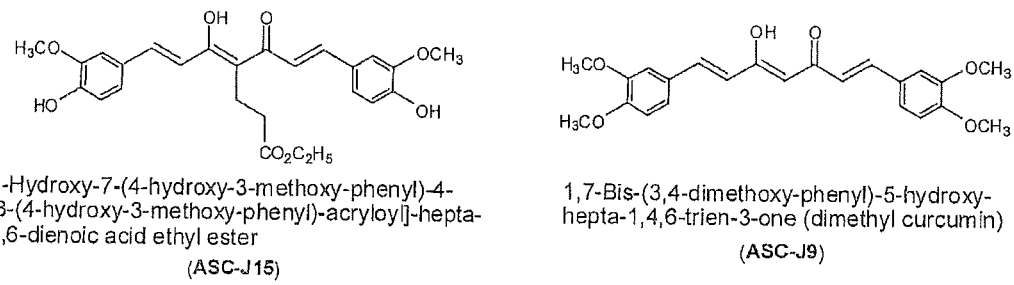
FIG. 1 depicts a structural representation of compounds ASC-J9 (1,7-Bis-(3,4-dimethoxy-phenyl)-5-hydroxy-hepta-1,4,6-trien-3-one) and ASC-J15 (5-Hydroxy-7-(4-hydroxy-3-methoxy-phenyl)-4-[3-(4-hydroxy-3-methoxy-phenyl)-acryloyl]-hepta-4,6-dienoic acid ethyl ester), which were previously shown to have anti-androgenic activities.

Unless defined otherwise, all technical and scientific terms used herein have the same meaning as is commonly understood by one of ordinary skill in the art to which this invention belongs. All patents, applications, published applications and other publications referred to are incorporated by reference in their entirety, including disclosed structures, formulas, methods of use, methods of treatment, and methods of production. In the event that there is a plurality of definitions for a term herein, those in this section prevail unless stated otherwise.

The term "(substituted phenyl)-propenal moiety" as used herein refers to a composition including a phenyl group having attached thereto a propenal moiety (when m equals 1) and an alkoxy or hydroxy moiety, or an alkyl or substituted alkyl moiety. The substitutions may be positioned meta or para or ortho with respect to the propenal moiety as used herein and refers to a general formula

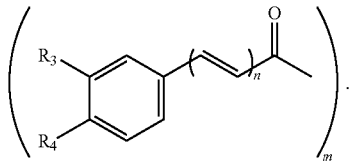

Where n may be any number of 1, 2, 3 or 4; and m may be any number of 1, 2, 3, 4, or more.

The term "alkyl" as used herein refers to a straight or branched hydrocarbon chain radical consisting solely of carbon and hydrogen atoms, containing no unsaturation, having from one to ten carbon atoms, and which is attached to the rest of the molecule by a single bond, e.g. methyl, ethyl, n-propyl, 1-methylethyl (iso-propyl), n-butyl, n-pentyl, 1,1-dimethylethyl (t-butyl), and the like.

The term "alkenyl" as used herein refers to a straight or branched hydrocarbon chain radical consisting solely of carbon and hydrogen atoms, containing at least one double bond, having from two to ten carbon atoms, and which is attached to the rest of the molecule by a single bond or a double bond, e.g. ethenyl, prop-1-enyl, pent-1-enyl, penta-1,4-dienyl, and the like.

The term "alkenylene" as used herein refers to a straight or branched hydrocarbon chain which contains a carbon-to-carbon double bond and is represented by the formula $C_nH_{2n-2}$, wherein hydrogen may be replaced by an additional carbon-to-carbon double bond or a monovalent substituent, e.g. ethenylene, prop-1-enylene and the like.

The term "alkoxy" as used herein refers to the radical having the formula —OR wherein R is an alkyl, haloalkyl or cycloalkyl. An "optionally substituted alkoxy" refers to the radical having the formula —OR wherein R is an optionally substituted alkyl as described herein.

The term "alkynl" as used herein refers to a straight or branched hydrocarbon chain radical consisting solely of carbon and hydrogen atoms, containing at least one triple bond, having from two to ten carbon atoms, and which is attached to the rest of the molecule by a single bond or a triple bond, e.g. ethynyl, prop-1-ynyl, but-1-ynyl, pent-1-ynyl, pent-3-ynyl and the like.

The term "aryl" as used herein refers to a radical of carbocyclic ring system wherein at least one of the rings is aromatic. The aryl may be fully aromatic or may contain an aromatic ring in combination with a non-aromatic ring. A "biaryl system" is a compound that includes at least two aryl groups.

The term "cycloalkyl" as used herein refers to a stable monovalent monocyclic or bicyclic hydrocarbon radical consisting solely of carbon and hydrogen atoms, having from three to ten carbon atoms, and which is saturated and attached to the rest of the molecule by a single bond, e.g. cyclopropyl, cyclobutyl, cyclopentyl, cyclohexyl, and the like.

The term "di-ketone bridge", or "ketone-enol bridge" as used herein refers to a straight or branched hydrocarbon chain including two ketones or an enol positioned in close proximity to a ketone respectively. The "di-ketone bridge" or "ketone-enol bridge" is positioned between at least two aryl moieties.

The term "hydroxyalkyl" as used herein refers to a straight or branched hydroxy substituted hydrocarbon chain radical having from one to ten carbon atoms, e.g. —CH$_2$OH, —(CH$_2$)$_2$OH and the like.

The term "androgen" as used herein refers to androgen hormones such as testosterone and dihydrotestosterone (DHT). DHT is the converted product of testosterone by the 5-alpha-reductase enzyme. Androgen stimulates or controls the development and maintenance of masculine characteristics and other physiological functions in vertebrates by binding to androgen receptors, which in turn binds to the androgen/AR-controlled genes (DNA) and activates or modulates the gene.

The term "androgen receptor" as used herein or "AR" refers to the intracellular receptor that specifically binds androgens, including testosterone and DHT. AR includes all mammalian isoforms, splice variants and polymorphisms of the androgen receptor.

The term "estrogen receptor" or "ER" or "ER family" as used herein refers to the intracellular receptor specific for estradiol (the main endogenous estrogen). When bound to a hormone, it acts as a transcription factor (it regulates the reading of DNA and production of proteins). ER includes ERα and ERβ. ER includes all mammalian isoforms, splice variants, and polymorphisms of the nuclear receptor.

The term "glucocorticoid receptor" or "GR" as used herein refers to the intracellular receptor that has a high affinity to cortisol and other glucocorticoids. GR includes all mammalian isoforms, splice variants, and polymorphisms of the nuclear receptor.

The term "progesterone receptor" or "PR" as used herein refers to the intracellular steroid receptor that specifically binds progesterone. PR includes all mammalian isoforms, splice variants and polymorphisms of the nuclear receptor.

The term "peroxisome proliferator activated receptor" or "PPAR" as used herein refers to all isotypes of PPAR, including PPARα, PPARβ and PPARγ. PPAR increases transcription of target genes by binding to a specific nucleotide sequence in the gene's promoter. When bound to its fatty acid ligand, PPARα forms a heterodimeric complex with the retinoid X receptor (RXR) to regulate transcription. PPARγ is activated by prostaglandins and leukotrienes and regulates the gene expression of proteins involved in the storage of fatty acids. PARβ is weakly activated by fatty acids, prostaglandins, and leukotrienes. Its physiological ligand has not been identified.

The term "retinoic acid receptor" or "RAR" as used herein refers to the intracellular receptor known to bind many retinoid forms. "RAR" includes all family members, which include RARα, RARβ and RARγ. "RAR" includes all mammalian isoforms, splice variants and polymorphisms of the nuclear receptor.

The term "retinoid x receptor" or "RXR" as used herein refers to the intracellular receptor that specifically binds 9-cis-Retinoic acid. "RXR" includes all mammalian isoforms, splice variants and polymorphisms of the nuclear receptor.

The term "steroid receptor" or "steroid nuclear receptor" as used herein refers to intracellular receptors that bind to and regulate the transcription of DNA under the regulation of steroid hormones. Receptors for the different hormones have strong structural and functional similarities which point to an evolution from a common ancestral gene and therefore are considered a gene superfamily. Representative receptors which belong to this gene superfamily include the DNA binding and regulatory proteins controlled by the steroid hormones estradiol (ER), glucocorticoid (GR), androgen (AR), progesterone (PR), mineralocorticoid (MR), the non-steroid hormones triiodothyronine (T3R) and dihydroxyvitamin D3 (VDR), and two classes of retinoid (all-trans retinoic acid and 9-cis retinoic acid) receptors (RARs and RXRs respectively). More than 32 genes encoding at least 75 proteins with different DNA specificity, regulation, or hormone affinity have been identified as part of this gene superfamily. New members of this superfamily are being reported frequently and are herein intended to be incorporated by reference in their entirety as published in peer reviewed scientific literature or as provided in sequence databases such as GenBank, whether DNA, RNA or polypeptide sequence, and SWISSPROT. Using new biotechnology, molecular biologists and biochemists have identified protein receptors for which the ligands have not yet been identified, thus giving birth to a class of "orphan receptors". "Steroid receptor" includes all mammalian splice variants and isoforms of the steroid receptors.

The term "extended release" as used herein refers to dosage form that provides for the delayed, slowed over a period of time, continuous, discontinuous, or sustained release of a compound or composition.

The term "pharmaceutically acceptable" as used herein refers to approved or approvable by a regulatory agency of the Federal or a state government for use in animals, and more particularly in humans. The term "pharmaceutically acceptable carrier" refers to an approved or approvable diluent, adjuvant, excipient or carrier with which a compound is administered.

The term "prodrug" as used herein refers to a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. In some but not all instances, the prodrug includes a cleavable ester, which upon cleavage, releases the active form.

The term "therapeutically effective amount" refers to the amount of a compound that, when administered to a patient for treating a disease or disorder, is sufficient to affect such treatment for the disease or disorder. The "therapeutically effective amount" will vary depending on the compound, the disease or disorder and its severity and the age and weight of the patient to be treated. The "therapeutically effective amount" may include a series of administrations that eventually causes a desired effect whether or not the initial administration is effective.

The term "derivative" as used herein refers to variations on a core structure or pharmacophore that yields a desired effect. Derivatives may include substitutions along the phenyl ring, the propenal region of the molecule or along a side chain. Thus derivatives encompassed herein include compounds formed from or include at least one disclosed compound, such as those identified in formulas I, II, III, IV, or V. It may be desirable to form derivatives of the particular compounds to modulate solubility, efficacy, aggregation and the like.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. 1972 11:942-944).

B. Compounds and Compositions Including (Substituted Phenyl)-Propenal Moieties The inventors of the present invention have found that compounds described herein, including those with at least one (substituted phenyl)-propenal moiety show promise for the treatment or prevention of medical conditions. Moreover compounds disclosed herein are believed to possess activities, such as reducing the proliferation of cells that are believed to have or suspected of having a cancerous profile. Additionally, compounds disclosed herein demonstrate the ability to selectively modulate populations of steroid receptors. Thus it is an object of the present invention to provide compounds having biological activities useful in the treatment or prevention of disease in mammals, such as humans.

The present invention discloses and encompasses a variety of compounds and their derivatives having utility in the areas of medical treatment, such as in the treatment or prevention of medical conditions. Thus compositions disclosed herein may be provided or administered as compounds themselves or may be adapted with a suitable carrier to effect the desired treatment. When providing the compounds disclosed herein as a pharmaceutical, the compounds may be provided in combination with a pharmaceutically acceptable carrier. When providing the compounds disclosed herein as a cosmetic, the compounds may be provided in combination with a cosmetically acceptable carrier. Pharmaceutically acceptable carriers and cosmetically acceptable carriers may be the same, may be derived from one another and the like as known in the pharmaceutical and cosmetic industries, or may be different such as but not limited to variations depending on desired route of administration. Compounds may be tested for solubility, activity and dipole moment before or after the preparation as a pharmaceutical or cosmetic and may be tested alone or in combination with other compounds disclosed herein for synergistic effects. Thus the present invention includes one or more compound and derivatives thereof, including those with hydrophilic or hydrophobic additions, substitutions or subtractions.

In one aspect of the present invention a compound having at least one (substituted phenyl)-propenal moiety is provided. In some embodiments, compounds having a (substituted phenyl)-propenal moiety have biological activity including anti-androgen/anti-AR biological activity. In one specific embodiment of the present invention the (substituted phenyl)-propenal moiety has the formula according to formula I:

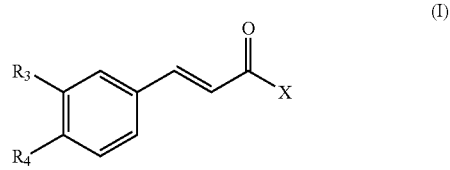

(I)

wherein 1) $R_3$ and $R_4$ are each independently selected from the group consisting of alkoxy, hydroxy, and hydrogen; and 2) X is selected from the group consisting of hydroxy, alkoxy, ethyl propionate, ethyl methyl carbonate, and carbonyl alkyl. As can be viewed in the Figures, compounds having at least one (substituted phenyl)-propenal moiety are capable of decreasing the presence of the androgen receptor or inducing degradation of the androgen receptor. Moreover compounds having at least one (substituted phenyl)-propenal moiety were shown to reduce cancer cell growth or proliferation of cancer cells. Such inhibition occurred in the presence of a compound capable of cancer cell stimulation. In various nonlimiting embodiments described herein the compound includes a (substituted phenyl)-propenal compound or a pharmaceutically acceptable salt thereof, selected from monomer 1, 3, 5, 6 or 7, alone or in combination, the monomers being provided below:

Monomers:

Monomer-1
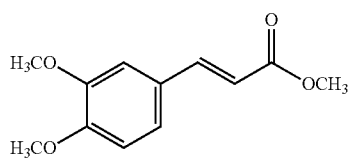

Monomer-3
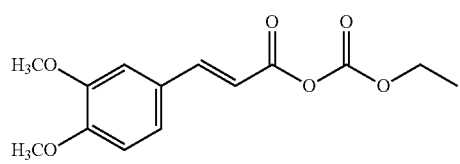

Monomer-5
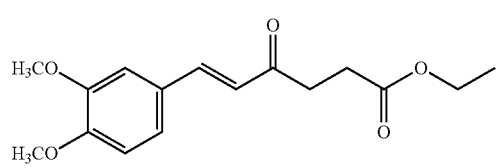

Monomer-6
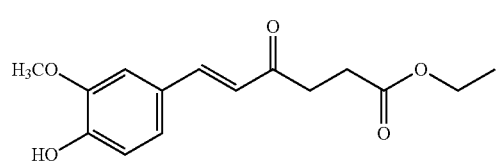

Monomer-7
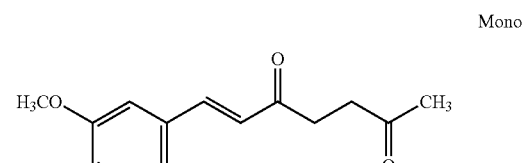

In various embodiments, derivatives of the above referenced monomers having biological activity are also provided. The derivatives may have substitutions at one or more positions to increase one or more characteristic such as activity, solubility and the like. Such derivatives may modulate the dipole moment of a compound and may result in a composition that is more or less hydrophobic or hydrophilic.

In another aspect of the present invention a compound is provided including a (substituted phenyl)-propenal moiety having the formula according to (IIa) or (IIb):

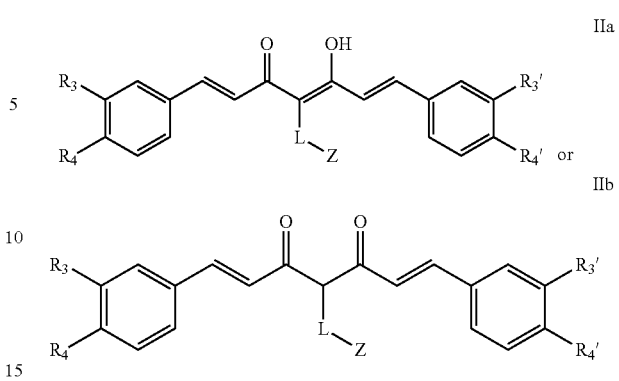

wherein: 1) $R_3$, $R_4$, $R_3'$ and $R_4'$ are independently selected from the group consisting of —H, —OH, and —OCH$_3$; 2) L is a C0-C8 alkylene or L is an unsaturated alkenylene or alkynl when Z is nothing; 3) Z is selected from the group consisting of —H, —OH, an aromatic ring, a cycloalkyl, —COR$_1$, —CO$_2$R$_1$, —CONR$_1$R$_2$, —NR$_1$R$_2$, —CX$_3$, wherein $R_1$ and $R_2$ are independently selected from the group consisting of —H, —CH$_3$, and —C$_2$H$_5$; 4) X is halogen atom selected from the group consisting of —F, —Cl, and —Br; and further wherein the formula IL and IIb are the equilibrate tautomers as a common phenomenon of diketone. In some embodiments the compound is selected from the group consisting of II-1, II-2, II-3, II-4 and II-5. The formulas provided as:

II-1
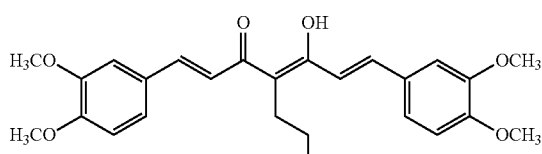

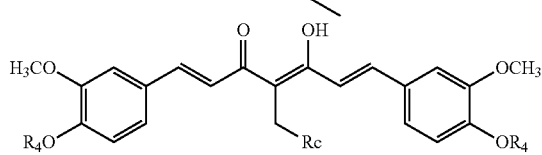

II-2: $R_4$ = H, CH$_3$,

Rc = 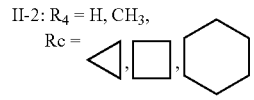

II-3
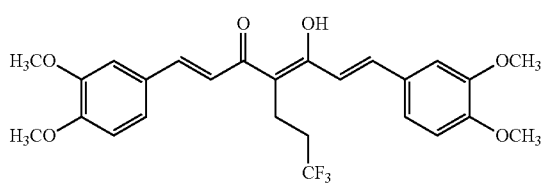

II-4
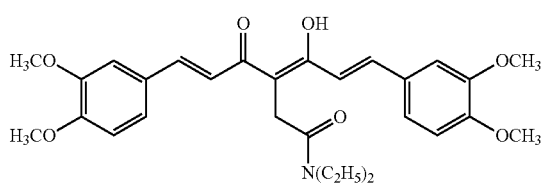

-continued

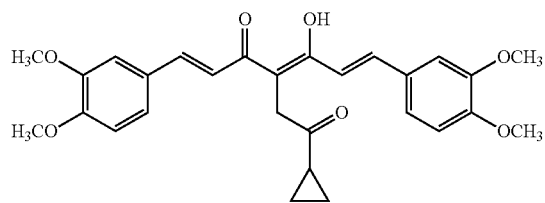
II-5

In another aspect of the present invention, a compound is provided according to formula IIc:

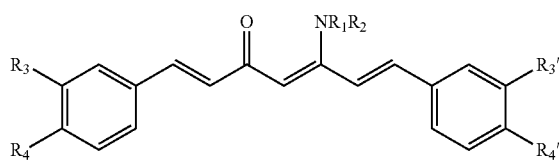
IIc wherein 1) $R_3$, $R_4$, $R_3'$, and $R_4'$ are independently selected from the group consisting of —H, —OH, and —OCH$_3$; and 2) $R_1$, and $R_2$ are independently selected from the group consisting of —H, —CH$_3$, —C$_2$H$_5$, a substituted aryl and a substituted benzyl group.

In another aspect of the present invention, a compound is provided according to formula III:

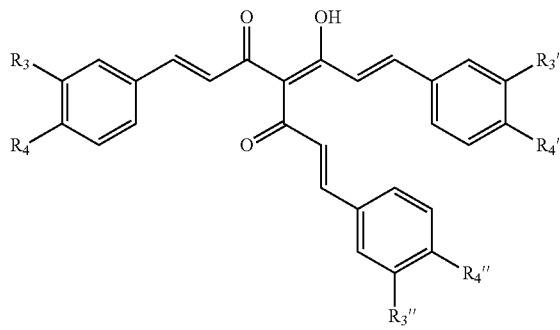
III wherein $R_3$, $R_4$, $R_3'$, $R_4'$, $R_3''$, and $R_4''$ are each independently selected from the group consisting of alkoxy, hydroxy, and hydrogen. Nonlimiting examples include those with the formula III-1 or III-2:

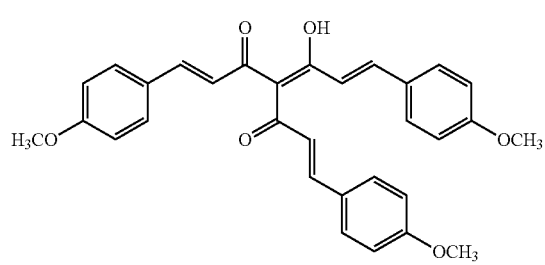
III-1

-continued

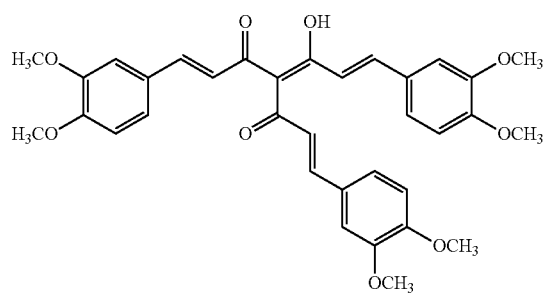
III-2

In another aspect of the present invention, a compound is provided according to the formula IV:

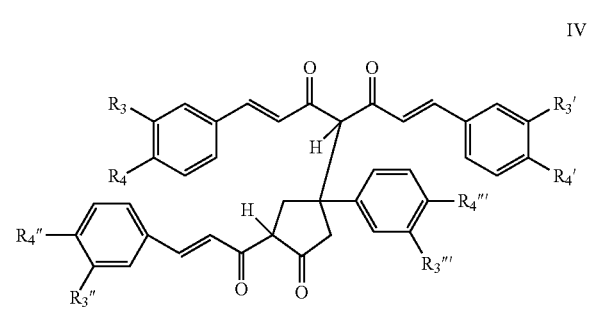
IV wherein $R_3$, $R_4$, $R_3'$, $R_4'$, $R_3''$, $R_4''$, $R_3'''$, and $R_4'''$ are each independently selected from the group consisting of alkoxy, hydroxy, and hydrogen. In one embodiment the compound has the formula IV-1:

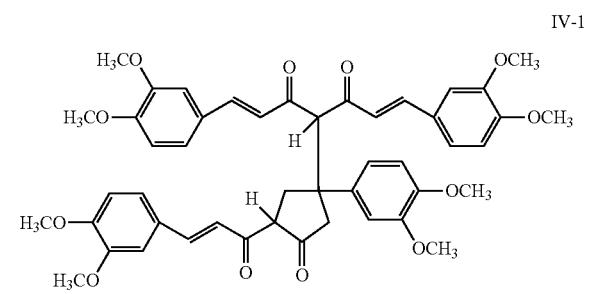 [SMILES: COc1ccc(/C=C/C(=O)C2CC(c3ccc(OC)c(OC)c3)(C(C(=O)/C=C/c3ccc(OC)c(OC)c3)C(=O)/C=C/c3ccc(OC)c(OC)c3)CC2=O)cc1OC]
IV-1

In another aspect of the present invention a compound is provided according to formula V:

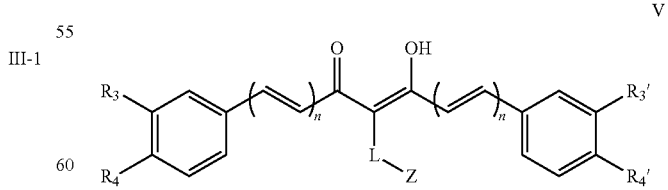
V wherein 1) each "n" is independently 1, 2, or 3; 2) $R_3$, $R_4$, $R_3'$, and $R_4'$ are independently selected from the group consisting of —H, —OH, and —OCH$_3$; 3) L-Z side chain can be no-exist, but if L-Z side chain exists, L is a C0-C8 alkylene, or an unsaturated alkenylene or alkynl when Z is nothing; 4) Z is selected from the group consisting of —H, —OH, an aromatic ring, a cycloalkyl, —CO₂R₁, —CONR₁R₂, —NR₁R₂, —CX₃; 5) R₁ and R₂ are independently selected from the group consisting of —H, —CH₃, and —C₂H₅; and 6) X is a halogen atom selected from the group consisting of —F, —Cl, and —Br. In some embodiments the compounds have the formula according to V-1 or V-2. The following are representatives of the compounds with formula V-1 and V-2:

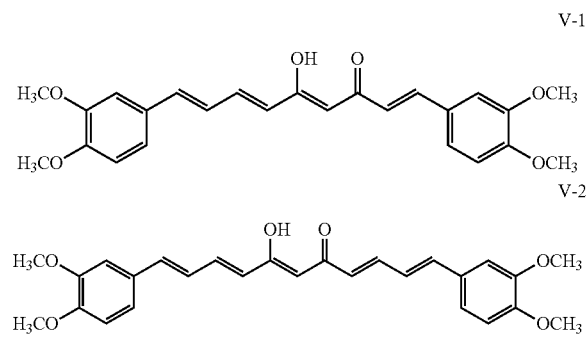

Synthesis of the disclosed compounds may be performed using standard practices known in the organic synthesis arts using known solvents. Synthesized compounds may be tested for desired activity such as degradation of a steroid receptor, such as the androgen receptor, the ability to prevent or inhibit proliferation of cancer cell lines, the reduction of tumor size in grafted animal studies and the like. Compounds identified as hits or leads may be further adapted using the synthesis methods and techniques disclosed m herein. Thus, variations on the provided synthetic methods will be readily apparent to those skilled in the art and are deemed to be within the scope of the present invention.

Example 1 demonstrates a variety of synthesis schemes for the provided monomers as well as derivatives thereof, which are also encompassed herein. In some embodiments derivatives are provided as a combination of monomers or portions thereof to form a biphenyl, triphenyl, or quadrophenyl ring system or more.

In many embodiments, a biphenyl ring system was utilized for testing and comparison to other proposed treatments; however compounds having a single (substituted phenyl)-propenal moiety, were also found to have activity such as the ability to prevent proliferation of cancer cell lines stimulated with DHT and the ability to degrade the androgen receptor. Some of the compounds of the present invention were prepared through a condensation of substituted benzaldehydes and 2,4-pentanedione or 3-substituted 2,4-pentanedions by the method known in the literature. Pedersen et al., Liebigs Ann Chem., 1557-1569 (1985). The desired substituents on the biphenyl ring and on the C4 of the conjugation bridge were synthesized either before or after the condensation. The length of conjugating bridge between the two phenyl moieties could be varied from 5 carbons to 11 carbons through synthetic strategies. Properly adding and removing protecting groups allow ultimate synthesis of disclosed compounds.

Several analogues and derivatives of compounds having a (substituted phenyl)-propenal moiety have been newly synthesized and evaluated for the anti-androgenic activity. The structure information of some but not all of the disclosed compounds is summarized in FIG. 2.

After extensive study of the structure and biological activity of 4-monosubstituted-1,7-bis-(3,4-dimethoxyphenyl)-5-hydroxy-hepta-1,4,6-trien-3-one, it was surprising to find that the 4-substitution(s) at 1,7-bis-(substituted-phenyl)-5-hydroxy-hepta-1,4,6-trien-3-one structures are the more important moiety that are related to the potent anti-androgen/AR activity of these compounds. Another important structural feature of this type of compounds is the enol-ketone bridge between the two phenyl groups, existing in equilibrium with its diketone form, which results in the unique molecular intrinsic fluorescence, i.e., the high density of the compound's color. This molecular property affects, in certain degree, pharmaceutical formulation, such as solubility and stability in solvents. In order to reduce the intrinsic fluorescent density, and to improve solubility and stability but not to sacrifice the biological activity, medicinal chemistry and organic synthesis strategies were used by introducing a second function group, such as a fluoro or methyl group, at C4 position, in addition to the prior mono substitution, to break the extensive molecular conjugation and stabilize the molecule to a distinct diketon form. By using such strategy, a series of 4,4-disubstituted 1,7-bis-(substituted phenyl)-hepta-1,6-diene-3,5-dione and 6,6-disubstituted 1,11-bis(substituted phenyl)-undeca-1,3,8,10-tetraene-5,7-dione compounds were synthesized and biological activity evaluated (FIG. 10). Unexpectedly, these newly synthesized diketone compounds not only have distinguishably reduced in fluorescent density, but also, more importantly, retain potent biological activity of anti-androgen/AR activity comparable to or in some compounds are more potent than their 4-mono-substituted counterparts. Another advancement of such structure modification is an improvement of metabolic stability. For example, structural modification of ASC-Q49 by introducing a methyl group at C4 position (see, Compound 6 in FIG. 10) improved its metabolic stability and reduced fluorescent density while retained the biological activity.

The innovations presented in this invention provide a more user friendly (i.e., less coloring) topical therapeutics for skin disorders such as acne, alopecia, wound healing and other diseases, disorders and conditions discussed herein and as applicable to the present invention.

Figure 11A:
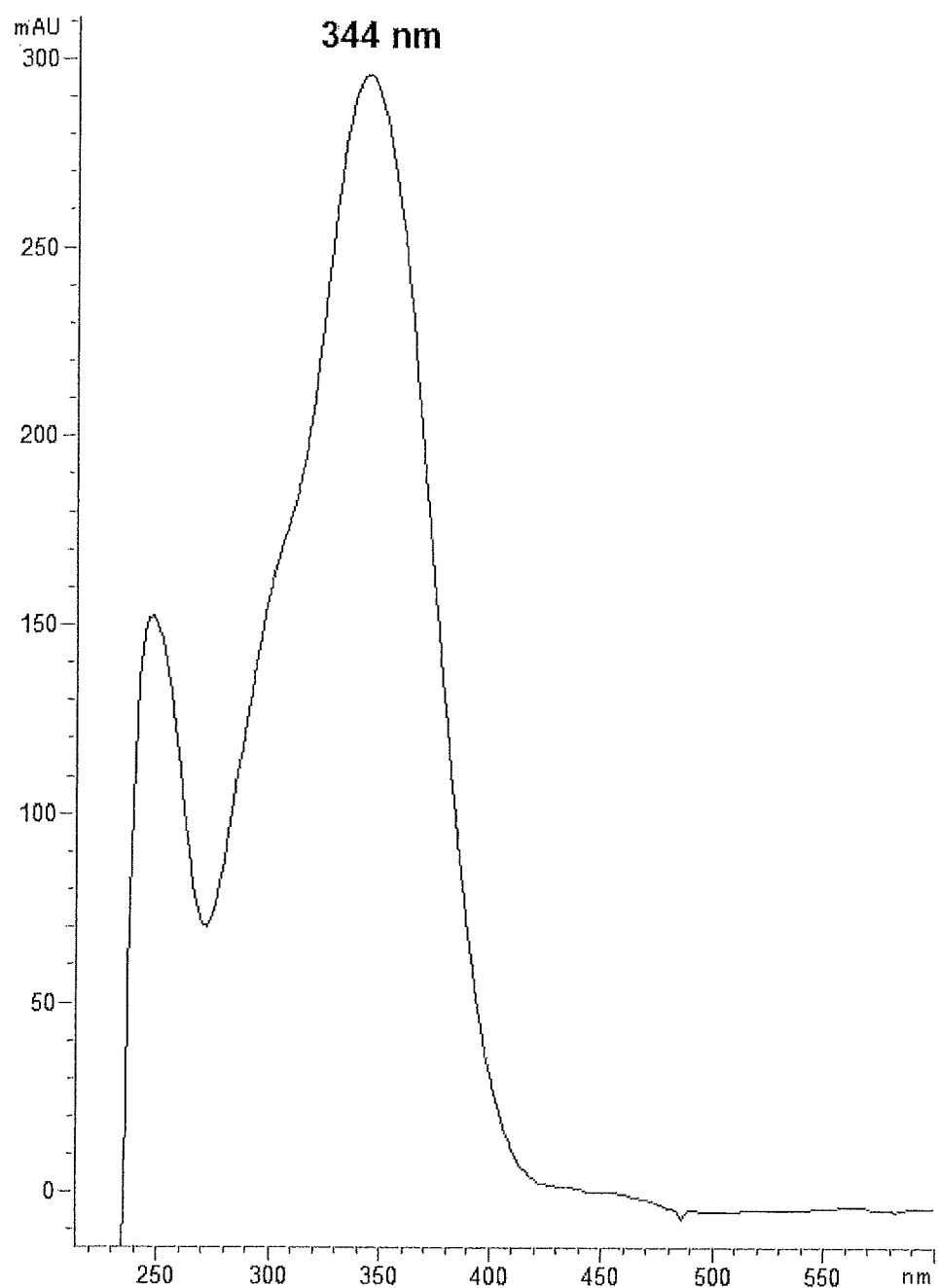
FIG. 11A, FIG. 11B and FIG. 11C: depict UV spectra of ASC-Q49 diketone tautomer peak (FIG. 11A, RT 20.6 minutes), enol tautomer peak (FIG. 11B, RT 23.7 minutes), and compound 6 (FIG. 11C, RT 21.1 minutes) from HPLC analysis.
Figure 11B:
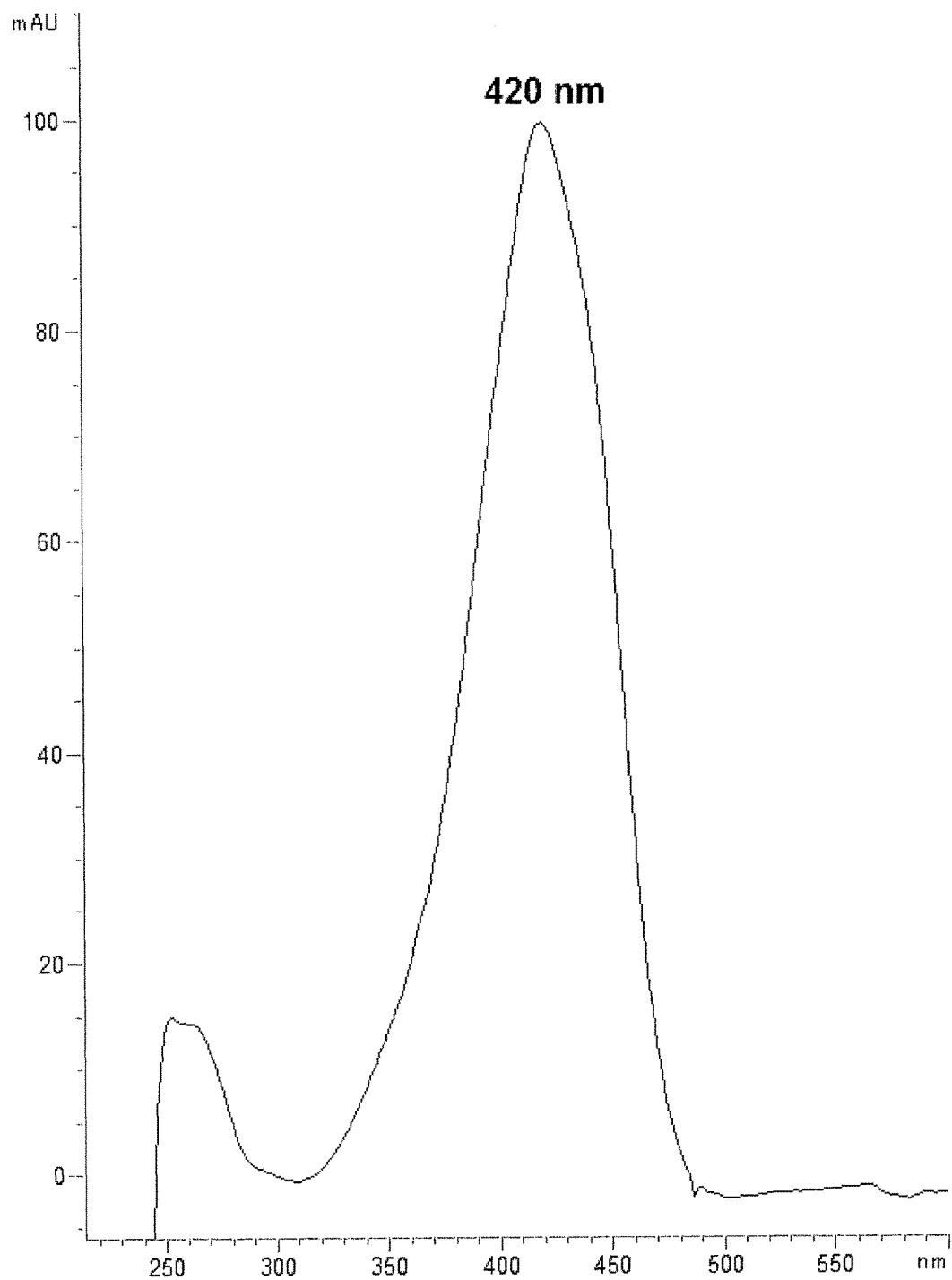
Figure 11C:
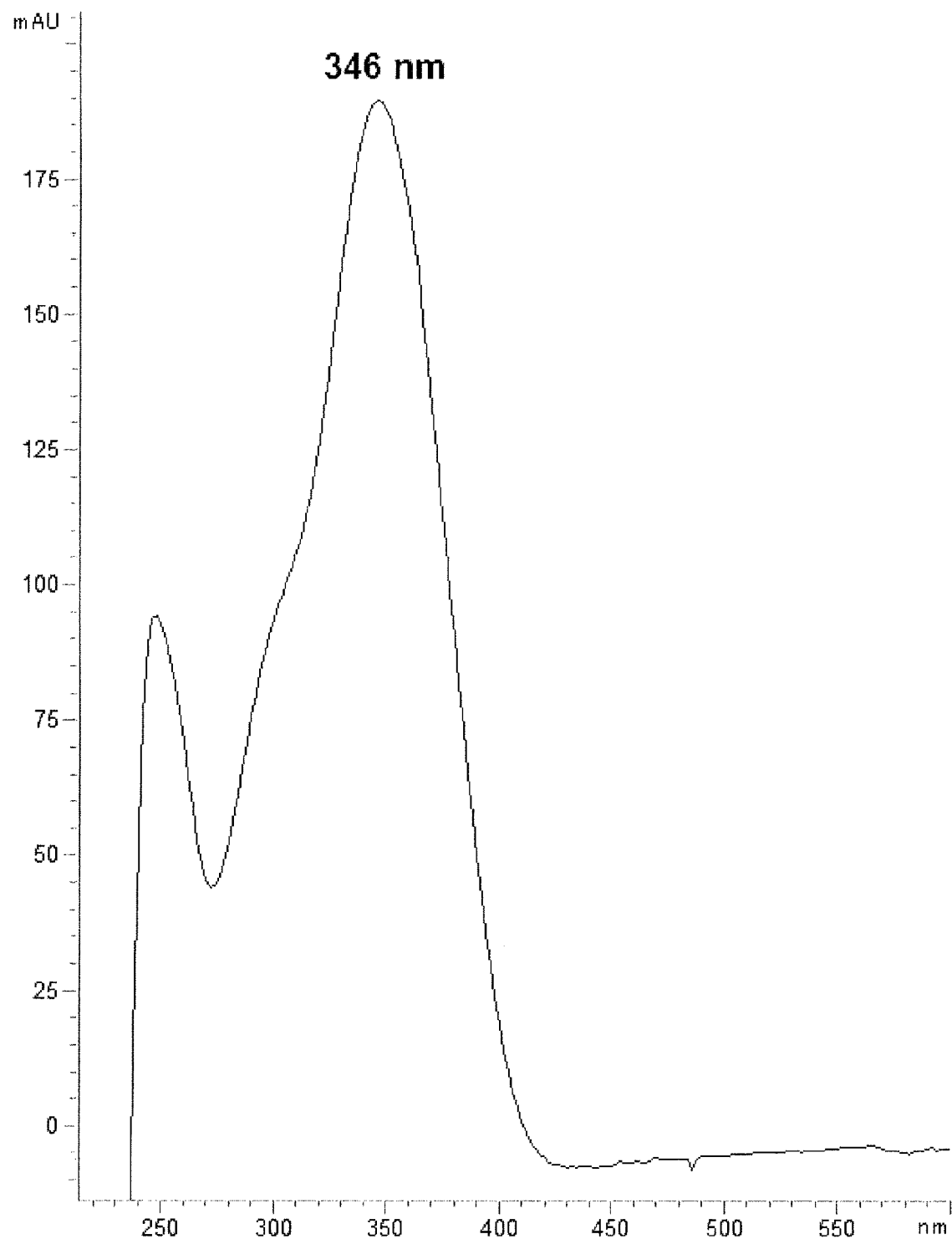

Interestingly and unexpectedly, these newly synthesized diketone, i.e., the further series of compounds, their intrinsic deep yellow or dark orange color (under visual light) had dramatically diminished or reduced to a light/pale yellow or a whitish color. This observation is evident by the HPLC profile and UV spectrum of compound ASC-Q49 which has a deep orange color and possess two separated tautomer peaks on HPLC, i.e., one diketone peak with UV maximum at 344 nm (FIG. 11A) and the one enol peak with UV maximum at 429 nm (FIG. 11B); whereas "compound 6" (a derivative of ASC-Q49), shows a light yellow color and only has one diketone peak exhibited UV maximum at 346 nm. (FIG. 11C). This single peak property of these compounds has significantly simplified the compound analysis and quantification, i.e., by eliminating or reducing the complexity of polymorphism and will benefit the process of pharmaceutical active ingredient (API) development, and chemical analysis of the API.

Interestingly and unexpectedly, was the finding that most of the further series of compounds have retained their biological activity, i.e., possess potent anti-androgen/AR activity, comparable to or in some case more potent than their 4-mono-substituted counterparts (Table 2). In addition, some compounds were also found to have their metabolic stability significantly improved in acidic condition as wells in biological fluids (such as human and rats plasmas) (Table 3 through Table 5). For example, ASC-Q49, an 4-monosubstituted-1,7-bis-(3,4-dimethoxyphenyl)-5-hydroxy-hepta-1,4,6-trien-3-one analog, was shown as a potent anti-androgen/AR agent (e.g., FIG. 5). However, its metabolic instability had made it a less ideal drug candidate. However, with the structural modification by introducing a methyl group to the C4 position according to, for example, Formula VI and Formula VIII, results in the compound 6 (in FIG. 10) and had significantly improved metabolic stability (Table 4 through Table 5).

The innovative findings presented in this invention can greatly increase the usefulness of the compounds as drugs (ie. increase the drugability) and thus benefit the therapeutic drug development. The reduction in intrinsic color of the compounds also increased the potential of development of these further series of compounds into topical drugs that could avoid the potential skin discoloration and make them more user friendly.

C. Pharmaceuticals and Cosmetics Including Compounds Having at Least One (Substituted Phenyl)-Propenal Moiety The present invention includes the disclosed compounds themselves, as well as their salts and their prodrugs, if applicable. The salts or prodrugs should retain a portion of the desired biological activity of the parent compound or be provided in a form that the body or subject can convert to a biologically active form. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, tartrate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Nonlimiting examples of prodrugs include esters and other pharmaceutically acceptable derivatives, which, upon administration to a subject, are capable of providing the compounds derivatives described above.

The compounds of the present invention may be formulated for administration for the prevention or treatment of a variety of medical conditions. Pharmaceutical formulations may include at least one of the disclosed compounds or pharmaceutically acceptable salt thereof in combination with a pharmaceutically acceptable carrier. Techniques of pharmaceutical production are well known in the art of the present invention and typically include mixing a compound or salt in the presence of a suitable carrier. Suitable carriers for use with the compounds of the present invention include diluents, excipients, or carrier materials, selected according to the intended form of administration and consistent with conventional pharmaceutical or cosmetic practice. Examples of suitable carriers include, but are not limited to, water, physiological saline, phosphate-buffered saline, a physiologically compatible buffer, saline buffered with a physiologically compatible salt, a water-in-oil emulsion, and an oil-in-water emulsion, an alcohol, dimethylsulfoxide, dextrose, mannitol, lactose, glycerin, propylene glycol, polyethylene glycol, polyvinylpyrrolidone, lecithin, albumin, sodium glutamate, cysteine hydrochloride, and the like, and mixtures thereof. Suitable carriers can also include appropriate pharmaceutically acceptable antioxidants or reducing agents, preservatives, suspending agents, solubilizers, stabilizers, chelating agents, complexing agents, viscomodulators, disintegrating agents, binders, flavoring agents, coloring agents, odorants, opacifiers, wetting agents, pH buffering agents, and mixtures thereof, as is consistent with conventional pharmaceutical practice ("Remington: The Science and Practice of Pharmacy", 20th edition, Gennaro (ed.) and Gennaro, Lippincott, Williams & Wilkins, 2000).

The pharmaceutical and cosmetic formulations may be provided depending on the desired route of administration using methods known in the pharmaceutical and cosmetic arts. Suitable routes of administration may include oral, intestinal, parenteral, transmucosal, transdermal, intramuscular, subcutaneous, rectal, intramedullary, intrathecal, intravenous, intraventricular, intraatrial, intraaortal, intraarterial, or intraperitoneal administration.

The pharmaceutical compositions of the present invention can be administered to the subject by a medical device, such as, but not limited to, implantable devices, biodegradable implants, patches, and pumps. Where such a device is used, the compositions may be formulated to include a dissolvable or nondissolvable matrix or medium (for example, a coating, membrane, film, impregnated matrix, polymer, sponge, gel, or porous layer on or within the medical device) to permit the release of the active compound or compounds over a specified period of time.

For use in a living, whole organism, such as in a human subject, compositions of the present invention can be formulated and provided in any formulation suitable to the intended form of administration and consistent with conventional pharmaceutical practice ("Remington: The Science and Practice of Pharmacy", $20^{th}$ edition, Gennaro (ed.) and Gennaro, Lippincott, Williams & Wilkins, 2000). Examples of suitable formulations include tablets, capsules, syrups, elixirs, ointments, creams, lotions, sprays, aerosols, inhalants, solids, powders, particulates, gels, suppositories, concentrates, emulsions, liposomes, microspheres, dissolvable matrices, sterile solutions, suspensions, or injectables, and the like. Injectables can be prepared in conventional forms either as liquid solutions or suspensions, as concentrates or solid forms suitable for solution or suspension in liquid prior to injection, or as emulsions.

D. Medical Treatments Incorporating Compounds Having at Least One (Substituted Phenyl)-Propenal Moieties Compounds of the present invention were tested for their effect on steroid receptors and their effect on cancer cell populations. It was found that compounds of the present invention were able to reduce androgen receptor expression (see, FIG. 3 and FIG. 4). Further investigation demonstrated that compounds of the present invention were able to inhibit cancer cell growth (see, FIG. 5) and reduce expression of the androgen receptor within cancer cells (see, FIG. 6 and FIG. 8). The inventors also considered potential mechanisms of action or potential pathways. FIG. 7 supports the inventors' beliefs that the compounds of the present invention induce degradation of the androgen receptor. Thus the activities demonstrated herein support therapeutic or prophylactic treatment against medical conditions such as a variety of cancers and androgen associated disorders.

The present invention includes methods of treating, ameliorating symptoms from or preventing the progression of a variety of medical conditions using the disclosed compounds and compositions, including pharmaceutical and cosmetic formulations. The medical conditions may, at least in part, be modulated by a steroid receptor. Steroid receptors of particular interest may include but are not limited to androgen receptor (AR), progesterone receptor (PR), estrogen receptor (ER), glucocorticoid receptor (GR), peroxisome proliferator-activated receptor (PPAR), retinoic acid receptors (RARs and RXRs), and orphan steroid hormone receptors. Compositions or compounds of the present invention may target a specific receptor, such as the androgen receptor or may target particular receptors within the steroid receptor superfamily.

The methods of the present invention may prevent, treat or ameliorate symptoms from cancers such as but not limited to prostate cancer, liver cancer, bladder cancer, cervical cancer, lung cancer and breast cancer, skin cancer, small cell lung cancer, testicular cancer, lymphoma, leukemia, esophageal cancer, stomach cancer, colon cancer, endometrial cancer, ovarian cancer, central nervous system cancer, and the like. The methods of the present invention may induce cytotoxicity against tumor cells or may inhibit tumor cell growth. Determining whether a compound or pharmaceutical is beneficial for the treatment or prevention of a particular disease may include testing the compounds or their derivatives in vitro, in vivo in an animal model or with a cell-based assay on a suitable cell line. In the instance of cancer, cell lines having a profile of a cancerous cell, such as cell lines prepared from cancer cells, may be utilized. In some embodiments activities of compounds of the present invention are evaluated for the ability to inhibit cancer cell growth or proliferation, optionally stimulated with a stimulator, such as DHT. Compounds disclosed herein were specifically shown to reduce growth or proliferation of prostate cancer cells.

In other embodiments, the compounds their derivatives, pharmaceutical compositions and the like are used to prevent, treat or ameliorate symptoms from neurological and neuromuscular disorders such as Kennedy Disease. Spinal and bulbar muscular atrophy (SBMA), or Kennedy's disease, is a gender-specific motor neuron disease that affects 1 in every 40,000 males (reviewed by Katsuno et al., 2004). SBMA patients have a mutated androgen receptor containing an expanded polyglutamine tract. The expanded polyglutamine androgen receptor forms aggregates that interfere with cell functioning and is the factor that causes the proximal muscle atrophy associated with SBMA. The methods of the present invention may include relieving the stress caused by aggregate formation by reducing the amount of the mutant AR to a level that could be more easily policed by the cells' native housekeeping machinery. The methods of the present invention may including selectively degrading the androgen receptor and thus may be used as a therapy for SBMA. The disclosed compounds that can enhance androgen receptor degradation may suppress the steady-state level of the receptor thus, attenuating the severity of aggregate formation in patients.

Compounds and compositions of present invention may prevent, treat or ameliorate symptoms from androgen related hair disorders. For example, androgenetic alopecia or "male pattern baldness" is hair loss caused by androgen activity on the androgen receptors in follicles and adjacent cells. As another example, hirsutism is excessive growth of thick dark hair in locations where hair growth in women usually is minimal or absent. Such male-pattern growth of terminal body hair usually occurs in androgen-stimulated locations, such as the face, chest, and areolae. Methods of the present invention may include administering a compound, pharmaceutical or cosmetic formulation to an individual in need of such treatment or prevention.

Compounds and compositions of the present invention may treat inflammation (e.g., rheumatoid arthritis), acne, alopecia, and may accelerate wound healing. Acne is caused by androgen-induced AR activation of sebaceous glands and may therefore be treated by administering a compound capable of preventing or decreasing AR activation. Compounds of the present invention are believed to induce degradation of the androgen receptor and thus would provide an effective treatment against such medical conditions. Androgenetic alopecia and other hair growth disorders are known to cause by the activation of androgen receptors (AR) in hair follicles by endogenous androgen. Certain inflammation conditions and wound healing are also believed to be associated with the androgen receptor in response to androgen. Methods of the present invention may include administering a compound, pharmaceutical or cosmetic formulation to an individual in need of such treatment or prevention. Topical application of such formulations may be of particular interest.

Compounds and compositions of the present invention may be used in the treatment of endocrine disorders. Androgen excess is one of the most common endocrine disorders in women (reviewed by Bulun and Adashi, 2003). This pathophysiological status can be found in women with various endocrine disorders, including polycystic ovary syndrome (PCOS), pituitary adenoma-induced hyperprolactinemia, Cushing's syndrome, congenital adrenal hyperplasia, non-classical adrenal hyperplasia, ovary or adrenal tumor, and iatrogenic androgen excess. Among these disorders, PCOS, occurring in 5-10% of reproductive-age women, is the most frequently identified cause of hyperandrogenism. Recently, a relative increase in the ratio of circulating androgens to circulating estrogens (named as androgenicity) has been observed in post-menopausal women (Lee et al., 2004). Androgenicity is the consequence of a greater decrease in estradiol and estrone synthesis than that of androgen synthesis after menopause, and its clinical implications are under active study. It has been shown that women exhibiting androgenicity are more frequently seen with central obesity (Peohlman et al., 1995). Fat deposit in the abdominal wall is metabolically active and is associated with insulin resistance in the peripheral tissues (Evans et al., 1983). Other than the above-mentioned endocrine disturbances, hyperandrogenic symptoms can also be detected in human immunodeficiency virus (HIV)-infected women showing lipodystrophy syndrome (Hadigan et al., 2000). It has been suggested that hyperandrogenism may be involved in lipid aberrations observed in the latter group of patients.

The methods of the present invention include the treatment of a variety of medical conditions as disclosed herein or are believed to be associated at least in part with a steroid or steroid associated disorder. The methods of treatment include administering a compound, pharmaceutical formulation or cosmetic formulation of the present invention to an individual or subject in need thereof. Subjects may be treated with a therapeutically effective dosage. A therapeutically effective dosage may vary somewhat from compound to compound, patient to patient, and will depend on the condition of the patient and route of delivery. As general guidance, a dosage from about 0.1 to about 50 mg/kg may have therapeutic efficacy, while still higher dosages potentially being employed.

Many of the features of the present invention are explained in greater detail in the following non-limiting examples. Thus the following examples are provided to further illustrate the various aspects and embodiments of the present invention. It is be understood; however, that the invention as fully described herein and as recited in the claims is not intended to be limited by the details of the following examples.

EXAMPLES

Example 1

Preparation of Compounds and Derivatives Having at Least One (3,4-Alkoxy or Hydroxy Substituted Phenyl)-Propenal Moiety In some embodiments, compounds composed of a single (substituted phenyl) propenal core structural unit (monomers) were prepared through standard and advanced organic syntheses. In some embodiments, compounds consisting of two or more (substituted phenyl) propenal core structural moieties were prepared by a condensation of substituted benzaldehydes and 2,4-pentanedion or 3-substituted 2,4-pentanedions by the method known in the literature. Pedersen et al. (Liebigs Ann. Chem., 1557-1569, 1985). The desired substituents on the biphenyl ring and on the C4 of conjugation bridge were synthesized either before or after the condensation. The length of conjugation bridge between the two phenyl moieties could be varied from 5 carbons to 11 carbons through synthetic strategies. Properly adding and removing protecting groups allow ultimate synthesis of the disclosed derivatives. In addition, various synthetic steps may be performed in an alternate sequence in order to give the desired compounds.

Derivative phosphate prodrugs were further prepared by reacting compounds having compounds a (substituted phenyl)-propenal moiety with phosphorous oxychloride in an appropriate solvent, e.g., dichloromethane, in the presence of an organic base, e.g., triethylamine. Tartrate of disclosed compounds as water-soluble salts were synthesized by reacting compounds having a (substituted phenyl)-propenal moiety with tartaric acid in water.

Chemical Synthesis

Melting points were determined on a Fisher-John melting point apparatus and are uncorrected. Proton Nuclear Magnetic Resonance ($^1$H NMR) and $^{13}$C NMR spectra were measured on Varian Gemini 300 or Inova 500 spectrometers with tetramethylsilane (TMS) as the internal standard. $^{31}$P NMR was conducted on 500 MHz Varian Inova spectrometer using phosphoric acid as external standard. Chemical shifts are reported in δ (ppm). Mass spectra (MS) were obtained on an Agilent 1100 series LC-MSD-Trap or PE-Sciex API-3000 spectrometers. Flash column chromatography was performed on silica gel (100-200 mesh) or alumina (aluminum oxide, basic, Brockmann I, standard grade, ~150 mesh). HPLC was conducted on Shimadzu SCL 10A instrument. HPFC was conducted on a Biotage system or ISCO Inc. Chemflash chromatographic system. Preparative thin layer chromatography (PTLC) on silica gel plates (Kieselgel 60, F254, 1.00 mm) were also used for separation and purification. Precoated silica gel plates (Kieselgel 60, F254, 0.25 mm) were used for thin layer chromatography (TLC) analysis. ASC-J9 was synthesized as starting material by reaction of 3,4-dimethoxybenzaldehyde with 2,4-pentanedione based on a published method (Pedersen et al., Liebigs Ann. Chem., 1557-1569, 1985).

Synthesis of Monomers 1, 3, 5-7.

The monomers, structurally with a (3,4-dimethoxy or 3-methoxy, 4-hydroxy substituted phenyl)-propenal moiety, a basic structure of the currently provided compounds, have been synthesized by reaction of 3-(3',4'-Dimethoxy-phenyl)-acrylic acid with corresponding reagents (monomers 1, 3), or reaction of 3,4-dimethoxybenzaldehyde or 3-methoxy-4-hydroxy benzaldehyde with ethyl levulinate (monomers 5 and 6). Monomor-7 was synthesized starting from 3-(3,4-dimethoxypheny)propane through two steps. More specifically, the synthesis methods for the monomers are described as below and illustrated in Scheme 1.

Monomer 1, 3-(3',4'-Dimethoxy-phenyl)-acrylic acid methyl ester, was synthesized by reaction of 3-(3',4'-Dimethoxy-phenyl)-acrylic acid with methanol in the presence of acetic chloride. After refluxing for 2.5 h, the reaction mixture was concentrated by evaporation to ⅓ and the white solid was filtered and dried in vacuo to get the desired product in 76% yield as a white crystalline solid. mp. 74-75° C. ESI MS m/z: 223.0 [M+H]$^+$; $^1$H NMR (300 MHz, CDCl$_3$) δ: 7.64 (d, 1H, J=15.9 Hz, H-3), 7.11 (dd, 1H, J=6.9, 2.1 Hz, H-6'), 7.05 (d, 1H, J=2.4 Hz, H-2'), 6.85 (d, 1H, J=8.4 Hz, H-5'), 6.32 (d, 1H, J=15.9 Hz, H-2), 3.92 (s, 6H, phenyl OCH$_3$), 3.80 (s, 3H, ester OCH$_3$).

Monomer 3, a mixed anhydride, was prepared by reaction of 3-(3',4'-Dimethoxy-phenyl)-acrylic acid in toluene/CH$_2$Cl$_2$ (1:1) in the presence of Et$_3$N. The solution was cooled to 0° C., ethyl chloroformate (1.5 eq.) was added dropwise. After stirring at 0° C. for 2 h, the precipitate was filtered out. The filtrate was concentrated to get a relatively pure white solid, which was purified by a fast filtration through a thin silica gel pad and eluted with hexanes:ethyl acetate (1:0 to 4:1) to afford the desired product as a white solid in quantity. ESI MS m/z: 281.0 [M+H]$^+$; $^1$H NMR (300 MHz, CDCl$_3$) δ: 7.78 (d, 1H, J=15.9 Hz, H-3), 7.15 (dd, 1H, J=8.4, 1.8 Hz, H-6'), 7.06 (d, 1H, J=1.8 Hz, H-2'), 6.89 (d, 1H, J=8.4 Hz, H-5'), 6.29 (d, 1H, J=15.9 Hz, H-2), 4.37 (q, 2H, J=6.9 Hz, OC$\underline{H_2}$CH3), 3.92 (d, 6H, J=1.2 Hz, phenyl OCH$_3$), 1.40 (t, 3H, J=7.2, OCH$_2$C$\underline{H_3}$).

Monomer 5, i.e., 6-(3',4'-Dimethoxy-phenyl)-4-oxo-hex-5-enoic acid ethyl ester, was synthesized by reaction of 3,4-dimethoxy-benzaldehyde with ethyl levulinate as shown in Scheme 1. Ethyl levulinate (1 eq.) reacted with boron oxide (0.7 eq) in ethyl acetate at 40° C. for 30 min. To the resulting mixture tributyl borate and 3,4-dimethoxy-benzaldehyde (both 1 eq.) were added and the mixture was stirred at 40-42° C. for 30 min. A solution of butyl amine (0.7 eq) in ethyl acetate was added slowly and the mixture was further allowed to stir at 40-42° C. overnight. 5% hydrochloride acid (1.3 eq) was added and the reaction mixture was stirred at 60° C. for 1 h. The reaction mixture was cooled to r.t. and was partitioned. The aqueous portion was extracted with ethyl acetate twice. The combined ethyl acetate extract was washed with water to pH 4 and dried over MgSO$_4$. After filtration and concentration, the crude was purified by PTLC to give monomer 5 as white solid. mp. 62-63° C. ESI MS m/z: 293.2 [M+H]$^+$; $^1$H NMR (300 MHz, CDCl$_3$) δ: 7.55 (d, 1H, J=16.2 Hz, H-6), 7.14 (dd, 1H, J=9.0, 2.1 Hz, H-6'), 7.08 (d, 1H, J=1.8 Hz, H-2'), 6.88 (d, 1H, J=8.4 Hz, H-5'), 6.65 (d, 1H, J=16.2 Hz, H-5), 4.16 (q, 2H, J=6.9 Hz, OC$\underline{H_2}$CH$_3$), 3.93 (s, 6H, phenyl OCH$_3$), 3.01 (t, 2H, J=6.6 Hz, H-3), 2.69 (t, 2H, J=6.6 Hz, H-2), 1.27 (t, 3H, J=6.9, OCH$_2$C$\underline{H_3}$).

Monomer 6, 6-(4-Hydroxy-3-methoxy-phenyl)-4-oxo-hex-5-enoic acid ethyl ester, was synthesized by reaction of vanillin with ethyl levulinate with a similar method recorded in the synthesis of Monomer 5. The desired compound was obtained as a yellow crystalline solid. mp. 55-56° C. ESI MS m/z: 279.2 [M+H]$^+$; $^1$H NMR (300 MHz, CDCl$_3$) δ: 7.54 (d, 1H, J=15.0 Hz, H-6), 7.12-7.06 (m, 2H, aromatic-H), 6.94 (d, 1H, J=8.1 Hz, aromatic H-5'), 6.63 (d, 1H, J=15.0 Hz, H-5), 4.16 (q, 2H, J=7.2 Hz, OC$\underline{H_2}$CH$_3$), 3.94 (s, 3H, phenyl OCH$_3$), 3.01 (t, 2H, J=6.9 Hz, H-3), 2.69 (t, 2H, J=6.9 Hz, H-2), 1.27 (t, 3H, J=7.2, OCH$_2$C$\underline{H}_3$).

Monomer 7, i.e., 7-(3,4-Dimethoxy-phenyl)-hept-6-ene-2,5-dione was made by 3-(3,4-dimethoxypheny)propane through 2 steps. 3,4-dimethoxycinnamaldehyde was made as described in the synthesis of Q110 (Scheme 13) in 60% yield. Dissolving the resulting compound (1 eq.) in dry EtOH, 3-butene-2-one (1 eq.) was added. The reaction solution was heated to 80° C. under N$_2$, 3-Benzyl-5-(2-hydroxyethyl)-4-methyl-1,3-thiazoliumchloride (0.1 eq.), TEA (0.4 eq.) in EtOH was added dropwise. The resulting reaction mixture was stirred at the temperature for 10 h, then evaporated to get a yellow oily residue. The crude was dissolved in CH$_2$Cl$_2$ and washed with 0.5% H$_2$SO$_4$, 2% NaHCO$_3$, and brine. After drying over Na$_2$SO$_4$, the crude was purified by chromatography though an Al$_2$O$_3$ flash column, followed by crystallization from ethyl ether and pentane to afford the target compound as an off-white solid. mp. 71-73° C. ESI MS m/z: 263.0 [M+H]$^+$; $^1$H NMR (300 MHz, CDCl$_3$) δ: 7.55 (d, 1H, J=16.2 Hz, H-6), 7.14 (dd, 1H, J=9.9, 2.1 Hz, H-6'), 7.08 (d, 1H, J=1.8 Hz, H-2'), 6.88 (d, 1H, J=8.4 Hz, H-5'), 6.64 (d, 1H, J=16.2 Hz, H-5), 3.93 (s, 6H, phenyl OCH$_3$), 2.98 (t, 2H, J=6.0 Hz, H-3), 2.83 (t, 2H, J=6.0 Hz, H-3), 2.24 (s, 3H, COC$\underline{H}_3$).

Scheme 1

1. Synthesis of Monomer 1:

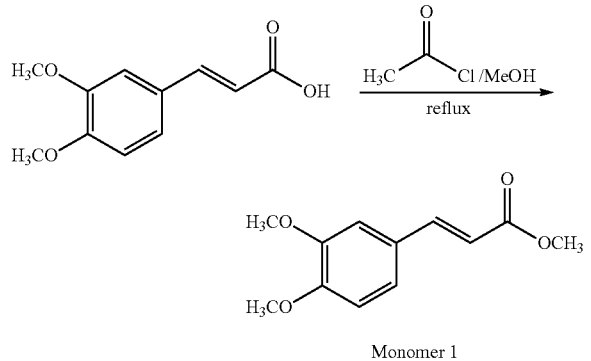

Monomer 1

2. Synthesis of Monomer 3:

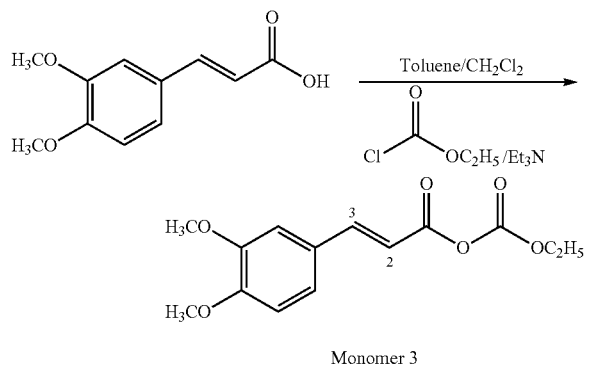

Monomer 3

3. Synthesis of Monomer 5:

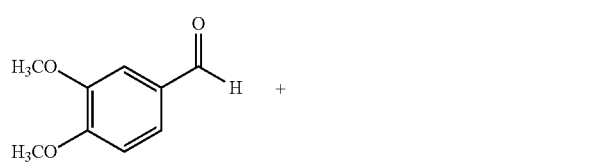

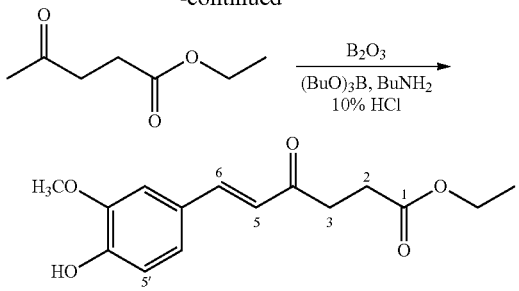

Monomer 5

4. Synthesis of Monomer 6:

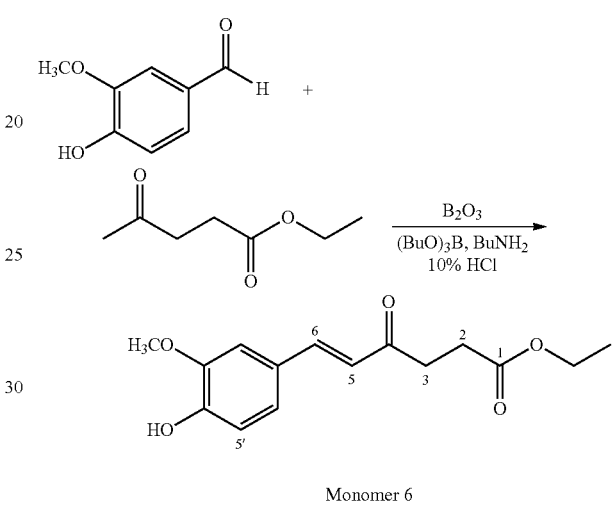

Monomer 6

5. Synthesis of Monomer 7:

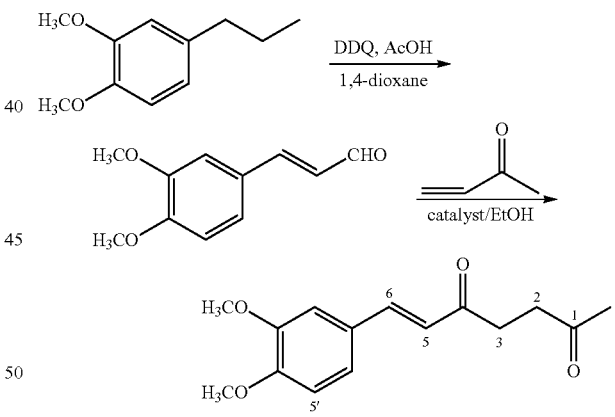

Monomer 7
catalyst: 3-Benzyl-5-(2-hydroxylethyl)-4-methyl-1,3-thiazoliumchloride Synthesis of compounds Q9, Q44, Q49, Q50, Q77, and Q98.

In order to study the effect of C4-substitution of the compounds on AR activity, a verity of C4-substituted compounds with different functional groups (e.g., hydroxyl, ester and amide, etc) were synthesized. These compounds were prepared by treatment of 1,7-Bis-(3,4-dimethoxy-phenyl)-5-hydroxy-hepta-1,4,6-trien-3-one (ASC-J9), synthesized through the method described in Scheme 2 with an appropriate bromide or chloride compound (or with ethylene oxide as an alternative for making compound Q9) in basic condition.

Compounds Q9 was synthesized as follows. To a 1N NaOH aqueous solution (0.2 mL, 0.2 mmol) containing 0.1 mmol of tetrabutylammonium bromide (phase transferring catalyst, PTC) was added ASC-J9 (0.1 mmol) in $CH_2Cl_2$ (0.5 mL) The mixture was stirred at room temperature for 10 min and 2-bromoethane alcohol (0.2 mmol) or ethylene oxide (25 mmol) was added. The resulting reaction mixture was stirred at 40° C. overnight for compound Q9. The two layers were separated, and the aqueous was extracted with $CH_2Cl_2$ 3 times. The combined organic layer was dried over $Na_2SO_4$ and concentrated. The crude residue was purified by PTLC and recrystallized from EtOAc. Analytical data for compound Q9 is shown below.

Compound Q9: Yellow crystalline solid (EtOAc), mp. 149-150° C. ESI MS m/z: 441.3 $[M+H]^+$; $^1H$ NMR (300 MHz, CDCl3) δ: 7.63 (d, 1H, J=15.9 Hz, H-1), 7.53 (d, 1H, J=15.9 Hz, H-7), 7.14-7.04 (m, 4H, aromatic ring H), 6.88-6.85 (2H, aromatic ring H), 6.65 (d, 1H, J=15.9 Hz, H-2), 6.31 (d, 1H, J=15.9 Hz, H-6), 4.29 (t, 2H, J=12, and 6 Hz, $CH_2\underline{CH_2}OH$), 3.94-3.88 (12H, $OCH_3$), 2.84-2.79 (t, 1H, C4-H), 2.14-2.10 (m, 2H, $C\underline{H_2}CH_2OH$).

Compounds Q44, Q49, Q77 were synthesized by reacting ASC-J9 in $CH_2Cl_2$ or THF with an appropriate bromide or chloride compound in the presence of $K_2CO_3$ and $Cs_2CO_3$ (9:1) or NaH as shown scheme 2. For the examples of making compounds Q49 and Q77. To a solution of NaH (4 eq.) in THF was added ASC-J9 (1 eq.) at 0° C. The resulting solution was stirred at 0° C. for 0.5 h then room temperature for 1.5 h. 2-Chloride-N,N-diethylacetamide (4 eq.) (for Q49) or 2-Chloride-N,N-dimethylacetamide (4 eq.) (for Q77) were added. The resulting mixture was heated to reflux overnight. The reaction mixture was cooled to r.t. (room temperature), diluted with EtOAc, and washed with 10% $H_2SO_4$ aq. The organic layer was further washed with sat. $NaHCO_3$, $H_2O$ and brine, and dried over $Na_2SO_4$. The desired product was purified by flash column chromatography and crystallized from EtOAc.

Compound Q49: Yellow crystalline solid, mp. 166-167° C. ESI MS m/z: 510.7$[M+H]^+$; $^1H$ NMR (300 MHz, CDCl3) δ: 7.68 (d, 2H, J=15.9 Hz, H-1,7), 7.16-7.06 (4H, aromatic ring H), 6.87-6.84 (2H, aromatic ring H), 6.80 (d, 2H, J=15.9 Hz, H-2,6), 4.97 (t, 1H, J=12.0 and 6.0 Hz, C4-H), 3.92-3.89 (12H, $OCH_3$), 3.43-3.33 (m, 4H, $CH_2CON(\underline{CH_2}CH_3)_2$), 3.04 (d, 2H, J=6.6 Hz, C4-$\underline{CH_2}CON(CH_2CH_3)_2$), 1.24 (t, 3H, $CH_2CON(CH_2C\underline{H_3})_2$), 1.09 (t, 3H, $CH_2CON(CH_2C\underline{H_3})_2$).

Compound Q77: Yellow crystalline solid, mp. 155-157° C. ESI MS m/z: 482.2 $[M+H]^+$; $^1H$ NMR (300 MHz, CDCl3) δ: 7.68 (d, 2H, J=15.6 Hz, H-1,7), 7.16-7.06 (4H, aromatic ring H), 6.87-6.83 (2H, aromatic ring H), 6.77 (d, 2H, J=15.6 Hz, H-2,6), 4.92 (t, 1H, J=13.5 and 6.6 Hz, C4-H), 3.92-3.88 (12H, $OCH_3$), 3.09-3.04 (m, 5H, —$C\underline{H_2}CO$ and $N(C\underline{H_3})$), 2.94 (s, 3H, $N(C\underline{H_3})$).

Compounds Q50 and Q98 were synthesized to compare their activity with Q44 and Q49 (Scheme 3). To a solution of 5-Hydroxy-1,7-bis-(4-hydroxy-3-methoxy-phenyl)-hepta-1,4,6-trien-3-one and 3,4-dihydro-2H-pyran (20 eq.) in dry dichloromethane was added pyridinium chlorochromate (PPTS) (0.1 eq.). The resulting solution was stirred at r.t. for 48 h. The solution was then washed with water. The solvent was removed and the resulting compound was purified on Biotage column chromatography. Reaction of the obtained product (Q1) with ethyl bromoacetae (Q50) or 2-Chloride-N,N-diethylacetamide (4 eq.) (Q98) in the presence of $K_2CO_3$ and $Cs_2CO_3$ (9:1) then removal of THP protecting group by PPTS/EtOH gave the desired products Q50 and Q98 respectively.

Compound Q50: Amorphous. mp. 63-65° C. ESI MS m/z: 455.2 $[M+H]^+$; $^1H$ NMR (300 MHz, CDCl3) δ: 7.65 (d, 2H, J=15.9 Hz, H-1,7), 7.19-7.04 (6H, aromatic ring H), 6.72 (d, 2H, J=15.9 Hz, H-2,6), 4.16 (2H, $COOC\underline{H_2}CH_3$), 3.96-3.92 (6H, $OCH_3$), 3.04 (d, 2H, J=7.2 Hz, C4-$\underline{CH_2}COOCH_2CH_3$), 1.27-1.23 (3H, $COOCH_2C\underline{H_3}$).

Compound Q98: Amorphous. mp. 68-71° C. ESI MS m/z: 482.10 $[M+H]^+$; $^1H$ NMR (300 MHz, CDCl3) δ: 7.65 (d, 2H, J=15.9 Hz, H-1,7), 7.12-7.03 (4H, aromatic ring H), 6.94-6.89 (2H, aromatic ring H), 6.76 (d, 2H, J=15.9 Hz, H-2,6), 4.96 (t, 1H, J=13.2 and 6.9 Hz, C4-H), 3.92-3.89 (6H, $OCH_3$), 3.44-3.33 (m, 4H, $CH_2CON(\underline{CH_2}CH_3)_2$), 3.04 (d, 2H, J=6.6 Hz, C4-$\underline{CH_2}CON(CH_2CH_3)_2$), 1.25 (t, 3H, $CH_2CON(C\underline{H_2}CH_3)_2$), 1.10 (t, 3H, $CH_2CON(CH_2C\underline{H_3})_2$).

Scheme 2

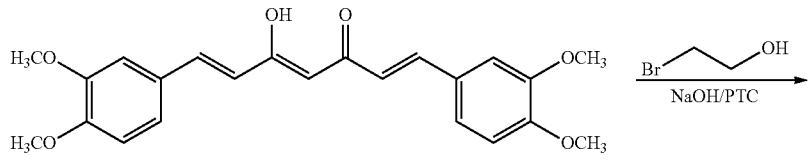

ASC-J9

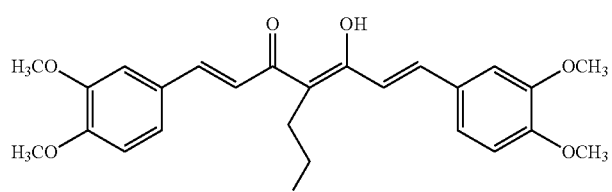

Compound Q9:

-continued
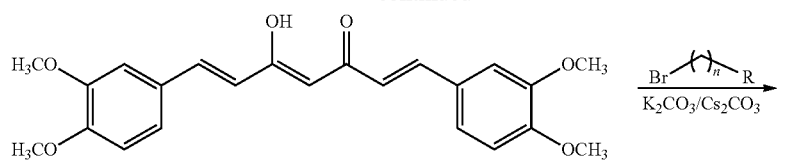
ASC-J9
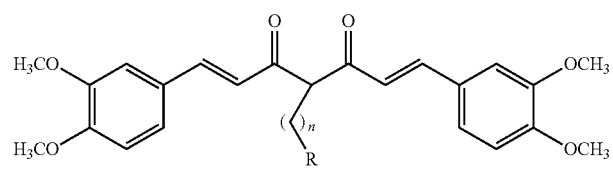
Compound Q44: n = 1, R = COOC$_2$H$_5$
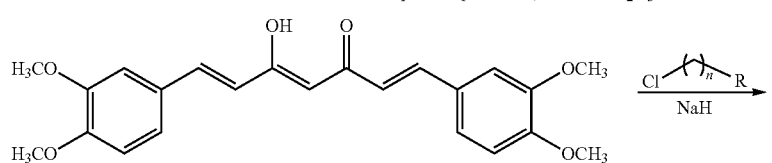
ASC-J9
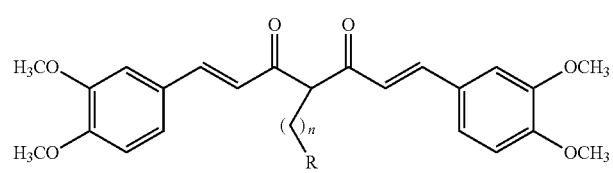
Compound Q49: n = 1, R = CON(C$_2$H$_5$)$_2$
Compound Q77: n = 1, R = CON(CH$_3$)$_2$
Scheme 3
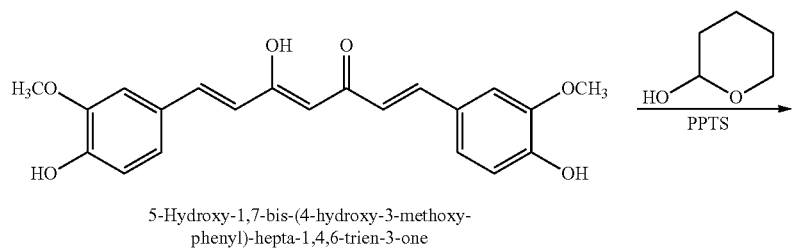
5-Hydroxy-1,7-bis-(4-hydroxy-3-methoxy-phenyl)-hepta-1,4,6-trien-3-one
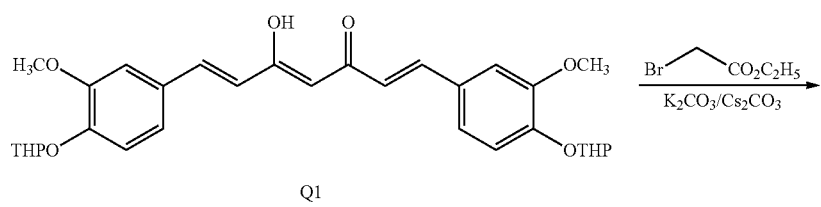
Q1
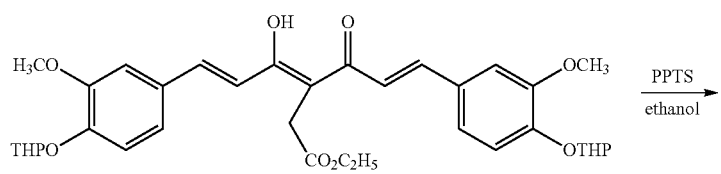

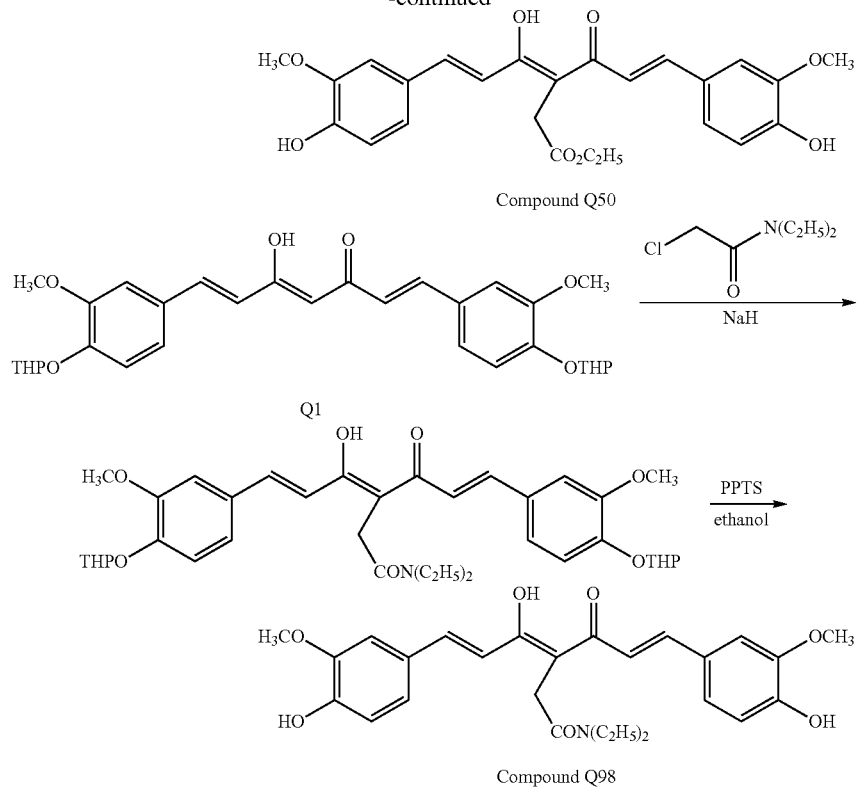

Compound Q50

Compound Q98

Synthesis of Compound: Q12.

This compound was synthesized starting from a commercially available substituted benzaldehyde with 4-acetyl-5-oxohexanoate as shown in Scheme 4.

More specifically, 4-acetyl-5-oxohexanoate was reacted with boron oxide (0.7 eq) in ethyl acetate at 40° C. for 30 min. To the resulting mixture tributyl borate and 3-methyl-4-hydroxy benzaldehyde (both 1.6-1.8 eq) were added and the mixture was stirred at 40-42° C. for 30 min. A solution of butyl amine (1.5 eq) in ethyl acetate was added slowly and the mixture was further allowed to stir at 40-42° C. overnight. 10% hydrochloride acid (2.5 eq) was added and the reaction mixture was stirred at 60° C. for 1 h. The reaction mixture was cooled to r.t. and partitioned. The aqueous portion was extracted with ethyl acetate twice. The combined ethyl acetate extract was washed with water to pH-4 and dried over MgSO$_4$. After filtration and concentration, the crude was purified by silica gel column chromatography (HPFC) with hexanes:ethyl acetate as eluent and crystallized from ethyl acetate.

Scheme 4

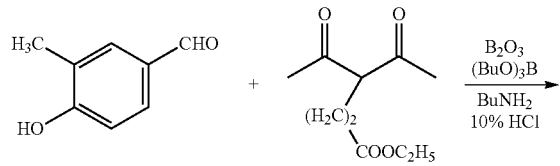

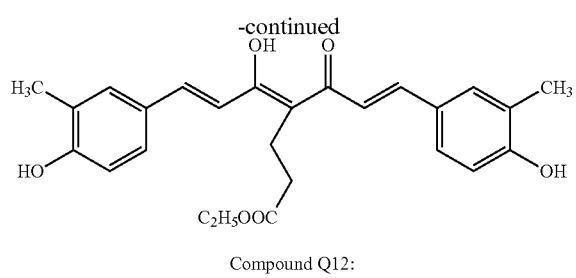

Compound Q12:

Synthesis of Compounds: Q30, Q35, and Q70

To study the function of di-ketone group in AR activity, a series of compounds with an imine group replacing one of ketones were synthesized.

Compounds Q30, Q35 were synthesized by reaction of ASC-J9 with appropriate amines in the presence of BF$_3$.OEt$_2$ (Scheme 5). For example, to a solution of ASC-J9 in 1,2-dichloroethane, N,N-diethylamine (compound Q30) (1.2 eq.) was added. The resulting solution was cooled to −30° C. and fresh BF$_3$.OEt$_2$ (2 eq.) was added dropwise. The mixture was stirred under nitrogen at −30° C. to room temperature with TLC monitoring. After quenching with the addition of pyridine (approximately 3 eq.) the mixture was washed with brine and dried over MgSO$_4$. Evaporation of the solvent and purification with flash column chromatography yielded the desired product Q30. ESI MS m/z: 452.4 [M+H]$^+$.

Compounds Q70 was synthesized by reaction of ASC-J9 (0.75 mmol) with (R)-(−)-2-phenylglycinol (1.16 mmol) in anhydrous toluene as shown in the scheme 5. The reaction mixture was heated to reflux with a Dean-Stark trap overnight. The solvent was evaporated, and ethyl acetate was added and re-evaporated. The obtained crude was purified by column chromatograghy on Biotage system to afford the desired product Q70 as a light yellow solid. ESI MS m/z: 516.4 [M+H]$^+$; $^1$H NMR (300 MHz, CDCl3) δ: 7.54 (d, 1H, J=15.6 Hz, H-1), 7.40-7.28 (5H, aromatic ring H), 7.13 (d, 1H, J=15.9 Hz, H-6), 7.16-7.09 (2H, aromatic ring H), 6.95-6.80 (4H, aromatic ring H), 6.68 (d, 1H, J=15.6 Hz, H-2), 6.63 (d, 1H, J=15.9 Hz, H-7), 5.63 (s, 1H, C4-H), 3.94-3.83 (m, 15H).

cifically, an aqueous solution of NaOH (2 eq.) and tetrabutylammonium bisulfate (TBABS) was stirred for 5 min. To the reaction solution was added a solution of ASCJ-9 (1 eq.) in 1,4-dioxane dropwise at rt and the resulting red two phased-mixture was stirred at rt. for 10 min. To this mixture was added 3-Chloro-2-methoxymethoxy-propene (1.5 eq) in 1,4-dioxane and the resulting solution was stirred at rt. for 5 min then at 70° C. overnight. The solid was removed by filtration and the filtrate was concentrated to dryness. The

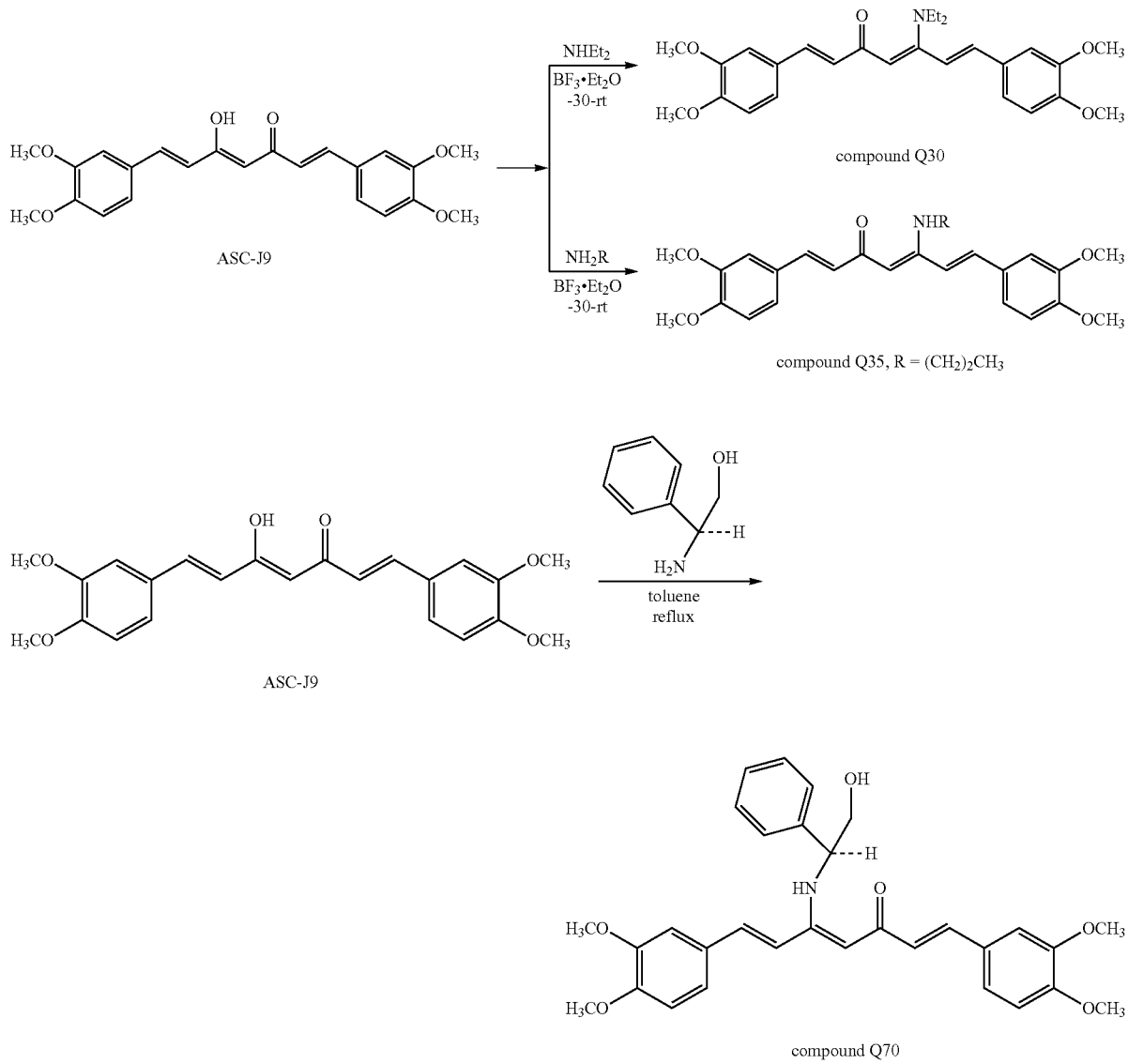

Synthesis of Compounds: Q99, Q106, Q113, JM2, and JM20.

In the continually exploring the effects of C4 side chain on AR activity, a series of compounds with a carbonyl group containing C4-substitutions were synthesized. Compound Q99 was synthesized by reaction of ASCJ-9 with 3-Chloro-2-methoxymethoxy-propene, followed by removal of methoxymethyl group as showed in Scheme 6. More speresulting residue was suspended in 1% $H_2SO_4$/dioxane (2:1, volume) and the suspension was stirred at rt. for 4 h with TLC monitoring. The reaction mixture was extracted with $CH_2Cl_2$, dried over $Na_2SO_4$, filtered and concentrated. The crude was purified by flash column chromatography and eluted with hexanes/EtOAc mixture to give the desired product as a yellow crystalline solid. M.p. 163-166° C. ESI MS m/z: 453.1 [M+H]$^+$.

Scheme 6

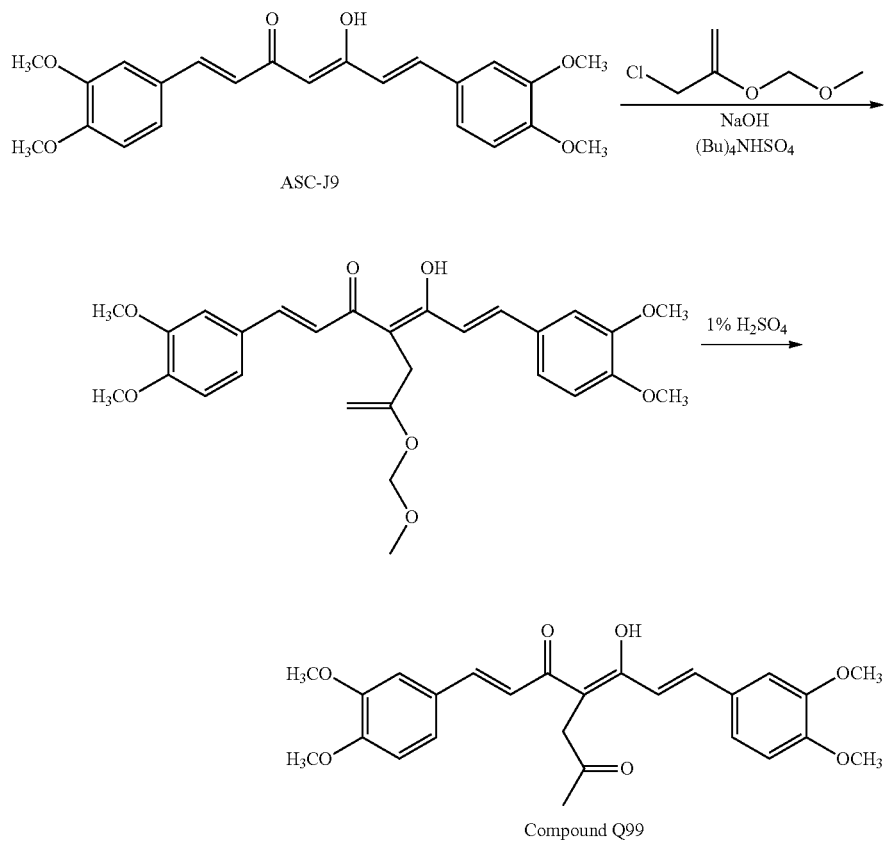

Compounds Q106 and Q113 was synthesized with the method described for making the compound Q44 in Scheme 2. An example to make Q106 was described as below. To a solution of ASC-J9 (0.25 mmol) in dry $CH_2Cl_2$ (5 mL) was added 2-bromo-1-phenyl-ethanone (1.2 eq.), $K_2CO_3$/ $Cs_2CO_3$ (10:1) (~2 eq.). The reaction mixture was stirred at rt overnight with TLC monitoring. The reaction mixture was diluted with EtOAc and washed with $H_2O$, then dried over $Na_2SO_4$. The obtained crude was purified by silica gel flash column chromatography eluted by hexanes and EtOAc mixture to get the desired product.

Compounds Q106, yellow crystal, mp. 160-2° C. ESI MS m/z: 515.2 [M+H]$^+$. $^1$H NMR (300 MHz, CDCl$_3$) δ: 8.14-8.01 (2H, aromatic ring H), 7.74-7.68 (2H, H-1,7), 7.65-7.46, (m, 4H, aromatic ring H), 7.18-7.15 (1H, aromatic ring H), 7.09-7.06 (2H, aromatic ring H), 6.91-6.80 (m, 4H, aromatic ring H), 6.69 (d, 2H, J=15.3 Hz, H-2,6), 3.92-3.90 (12H, OCH$_3$), 3.78 (2H, —C$\underline{H}_2$CO).

Compounds Q113, yellow fluffy solid, mp. 145-7° C. ESI MS m/z: 479.1 [M+H]$^+$. $^1$H NMR (300 MHz, CDCl$_3$) δ: 7.75 (d, 1H, J=15.3 Hz, H-1,7), 7.20-7.17 (2H, aromatic ring H), 7.07-7.06 (2H, aromatic ring H), 6.90, 6.88 (2H, aromatic ring H), 6.86 (1H, J=15.3 Hz, H-2,6), 3.95-3.93 (12H, OCH$_3$), 3.76 (2H, —C$\underline{H}_2$CO), 2.14-2.05 (m, 1H, cyclopropyl-H), 1.10-1.04 (m, 2H, cyclopropyl-H), 0.93-0.86 (m, 2H, cyclopropyl-H).

Compound JM2 was synthesized by reaction of ASC-J9 (40 mg) with iodoacetamide (80 mg) and anhydrous sodium carbonate (40 mg) in dry acetone as showed in Scheme 7. The reaction mixture was heated to reflux for 24 hours. After cooling, the mixture was filtered to remove inorganic solid and filtrate was evaporated. The obtained crude residue was purified by preparative silica gel chromatography plate (Ethyl acetate only) to afford the desired product as a light yellow solid.

Compound JM2, amorphous; ESI MS m/z: 452.2 [M+H]$^+$; $^1$H NMR (300 MHz, CDCl3) δ: 7.79 (d, 2H, J=15.3 Hz, H-1, 7), 7.4-6.4 (6H, aromatic ring H), 6.33 (d, 2H, J=15.3 Hz, H-2, 6), 3.93, 3.92 (all s, both 6H, OC$\underline{H}_3$), 2.06 (d, J=6.3 Hz, 2H, C$\underline{H}_2$CONH$_2$).

Synthesis of JM-10. A mixture of 1.0 gram of ASC-J9, 5 ml of acetic anhydride, and 1 ml of trimethyl orthoformate was stirred at 70° C. for 22 hours (Scheme 7). The solution was then vacuum evaporated to dryness. The residue was re-dissolved in CH$_2$Cl$_2$-ethanol to re-crystallize. Compound JM10 was afforded as orange-reddish crystals (270 mg); mp. 137-138° C.; ESI MS m/z: 425.2 [M+H]$^+$; $^1$H NMR (300 MHz, CDCl$_3$) δ: 10.37 (s, 1H, C4-CO$\underline{H}$), 7.94, 7.71 (both d, 2H each, J=15.6 Hz, H-1, 2, 6, 7), 7.26 (dd, 2H, J=1.8, 8.7 Hz, aromatic 5'-H), 7.17 (d, 2H, J=1.8 Hz, aromatic 2'-H), 6.91 (d, 2H, J=8.7 Hz, aromatic 6'-H), 3.97, 3.95 (both s, 6H each, OCH$_3$).

Scheme 7

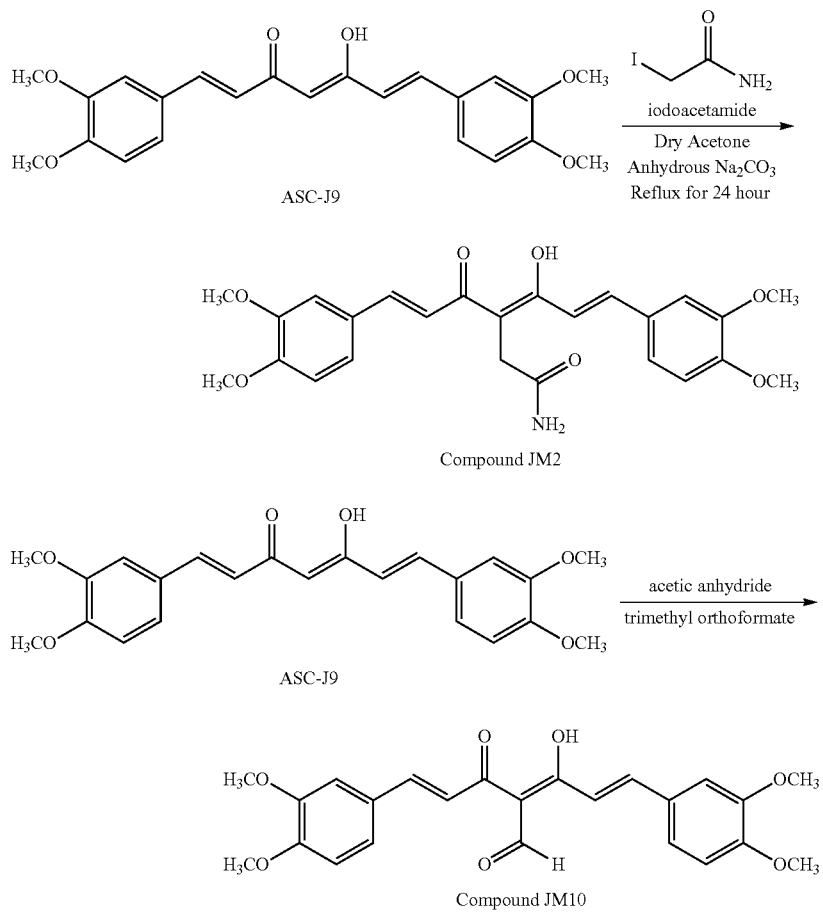

Synthesis of Compound Q100, Q101, JM1, JM6, and JM7.

Compounds Q100, Q101, JM1, JM6, and JM7 were made with an unsaturated side chain at C4 position of ASC-J9 intending to enhance anti-prostate cancer activity. Compound Q100 was synthesized by reaction of ASC-J9 with 3-bromo-propyne in $CH_2Cl_2$ at 60° C. over night in the presence of $K_2CO_3$. Compound Q101 was made by reaction of ASC-J9 with bromopropene in DMF at 100° C. for 2 h in the presence of $K_2CO_3$ and KI (Scheme 8). The crude compounds were purified by silica gel flash column chromatography eluted by hexanes and EtOAc mixture to get the desired products.

Compound Q100, yellow solid amorphous, mp. 75-78° C. ESI MS m/z: 453.1 [M+H]$^+$. $^1$H NMR (300 MHz, $CDCl_3$) δ: 7.75 (d, 1H, J=15.3 Hz, H-1), 7.69 (d, 1H, J=15.6 Hz, H-7), 7.23-7.05, and 6.91-6.85 (m, 7H, aromatic ring H and H-2), 6.73 (1H, J=15.6 Hz, H-6), 3.96-3.91 (12H, $OCH_3$), 3.46 (1H, C4-H), 2.96 (s, 114, acetylene), 2.94-2.90 (dd, 2H, —C$\underline{H}_2$CCH).

Compound Q101, amorphous, mp. 69-72° C. ESI MS m/z: 437.1 [M+H]$^+$. $^1$H NMR (300 MHz, $CDCl_3$) δ: 7.71 (d, 1H, J=15.6 Hz, H-1), 7.70 (d, 1H, J=15.6 Hz, H-7), 7.18-7.12 (m, 2H, aromatic ring H), 7.06-7.00 (m, 2H, aromatic ring H), 6.90-6.85 (2H, aromatic ring H), 6.85 (1H, J=15.6 Hz, H-2), 6.67 (1H, J=15.6 Hz, H-6), 5.64-5.49 (m, 1H, ethylene H), 5.19-5.07 (m, 2H, ethylene H), 3.94-3.91 (m, 12H, $OCH_3$), 296 (d, 2H, —C$\underline{H}_2$—).

Scheme 8

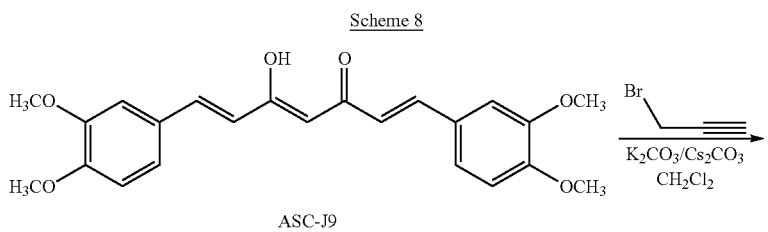

-continued

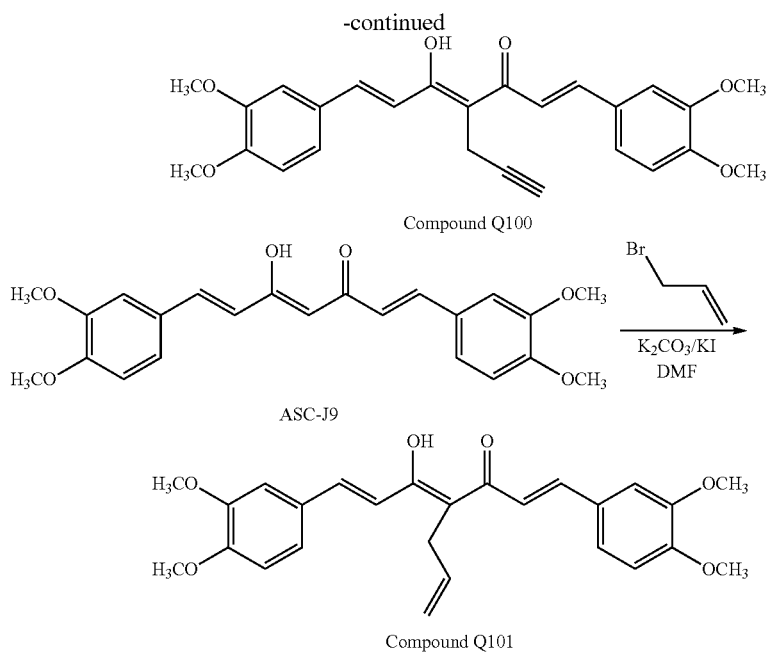

Compound Q100

ASC-J9

Compound Q101

Compound JM1 was synthesized by reaction of ASC-J9 (40 mg) with cinnamyl bromide and anhydrous sodium carbonate in dry acetone (Scheme 9). The reaction mixture was heated to reflux for 24 hours. After cooling, the mixture was filtered to remove inorganic solid and filtrate was evaporated. The obtained crude was purified by preparative silica gel chromatography plate (n-Hexane-Ethyl acetate=1:1) to afford the desired product JM1 as a light yellow solid. Amorphous; ESI MS m/z: 513.4 [M+H]$^+$; $^1$H NMR (300 MHz, CDCl3) δ: 7.74 (d, 2H, J=15.3 Hz, H-1, 7), 7.32 (d, 1H, J=18.6 Hz, —CH2CH=C$\underline{H}$—), 7.4-6.4 (11H, aromatic ring H), 6.93 (d, 2H, J=15.3 Hz, H-2, 6), 6.46 (d, 1H, J=18.6 Hz, —CH2C$\underline{H}$=CH—), 3.91, 3.88 (all s, both 6H, OC$\underline{H_3}$), 3.50 (br d, 2H, —C$\underline{H}$2CH=CH—).

Compound JM6 was synthesized by reaction of ASC-J9 (60 mg) with bromomethyl acetate (50 mg) and sodium hydroxide (20 mg) in dry acetone (Scheme 9). The reaction mixture was heated to reflux for 24 hours. After cooling, the mixture was filtered to remove inorganic solid and filtrate was evaporated. The obtained crude was purified by preparative silica gel chromatography plate (n-Hexane-Ethyl acetate=1:2) to afford the desired product JM6 as a light yellow solid (ESI MS m/z: 467.3 [M+H]$^+$).

Scheme 9

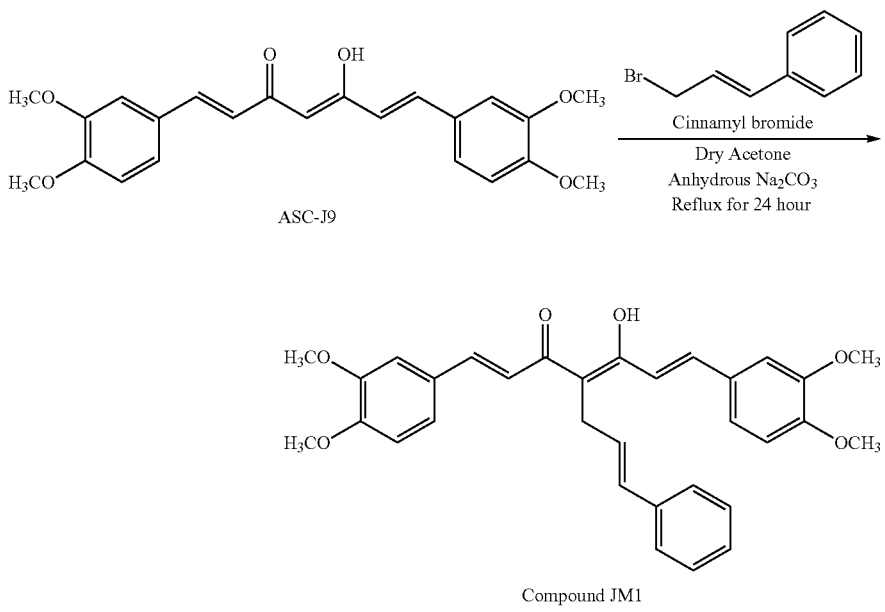

Compound JM1

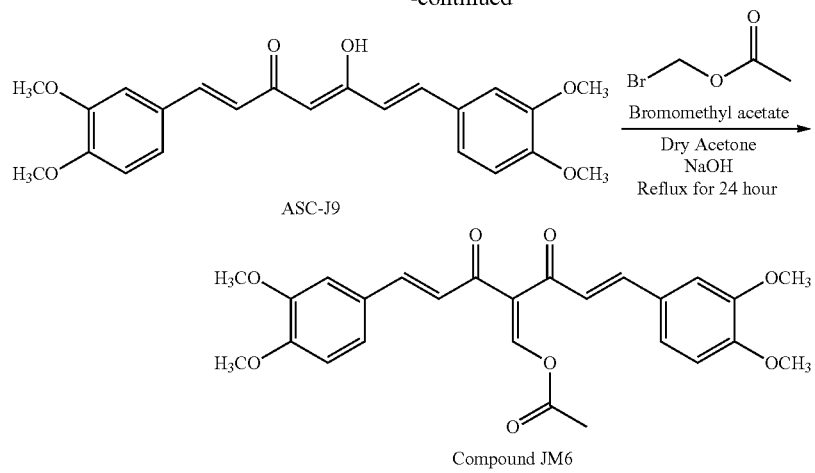

ASC-J9

Compound JM6

Compound JM7, obtained as a by-product of JM4 aforementioned, yellow fine crystals from EtOAc/hexanes; mp. 109-110° C.; ESI MS m/z: 545.2 [M+H]$^+$; $^1$H NMR (300 MHz, CDCl$_3$) δ: 7.83 (s, 1H, CH=C— at C4), 7.79, 7.51, 6.98, 6.83 (all d, 1H each, J=15.5 Hz, H-1, 2, 6, 7), 7.20, 7.15, 7.08 (all dd, 1H each, J=1.8, 8.4 Hz, aromatic 5'-H), 6.87 (d, 1H, J=8.4 Hz, aromatic 6'-H), 6.83 (d, 2H, J=8.4 Hz, aromatic 6'-H), 7.07, 7.06, 6.99 (all d, 1H each, J=1.8 Hz, aromatic 2'-H), 3.92, 3.88 (all s, 6H each, OCH$_3$), 3.90, 3.83 (all s, 3H each, OCH$_3$).

Synthesis of Compounds: Q102-Q104, Q108, Q114-Q115, JM12-JM14, and JM16-JM19.

Compounds Q102-Q104, Q108, JM12-JM14, JM17 were synthesized to evaluate the properties of the C4-alkyl substitution on ASC-J9 with differences in chain length, in ring size, and in functional groups at chain-end (e.g., Q108 and JM14). Compounds Q114-Q115, JM16, JM18-19 were synthesized to evaluate the functions of not only the C4-side chain but also the substitutions on the bi-phenyl moiety. All compounds were prepared by reaction of 2,4-pentadione with appropriate alkyl or alkylene (or substituted alkyl or alkylene) bromide or iodine in benzene with DBU as a base.

The resulting product 3-substituted 2,4-pentadione further reacted with 3,4-dimethoxybenzaldehyde or 4-methoxybenzaldehyde or 3-methoxy-4-hydroxybenzaldehyde to afford the desired products (Scheme 10). An example to make Q104 was illustrated as below. Mix 2,4-pentadione 0.2 g (2 mmol) and DBU 30 ul (1 eq.) in benzene 3 mL To this solution was added dropwise 0.48 g (1 eq.) of octyl iodine in 1 mL of benzene at r.t. The resulting solution was stirred at r.t. overnight. The reaction mixture was washed with brine and extracted the CH$_2$Cl$_2$, dried over Na$_2$SO$_4$ and purified by silica gel flash column chromatography to give a mixture of C3-octanyl substituted 2,4-pentadione and O-octyl substituted 2,4-pentadione. Reaction of the mixture with 3,4-methoxybenzaldehyde through the method mentioned above afforded the compound Q104.

Compound Q104, yellow solid from EtOAc/hexanes (2:1), mp. 87-90° C. ESI MS m/z: 509.3 [M+H]$^+$; $^1$H NMR (300 MHz, CDCl3) δ: 7.71 (d, 1H, J=15.6 Hz, H-1), 7.63 (d, 1H, J=15.9 Hz, H-7), 7.21-7.14 (m, 2H, aromatic H), 7.08-7.05 (m, 2H, aromatic H), 6.95 (d, 1H, J=15.6 Hz, H-2), 6.91-6.84 (m, 2H, aromatic H), 6.73 (d, 1H, J=15.9 Hz, H-6), 3.94-3.91 (m, 12H, —OCH$_3$), 2.55 (t, 1H, H-4), 1.61-1.22 (m, 12H, butyl group), 0.87 (m, 3H, —CH$_3$).

Scheme 10

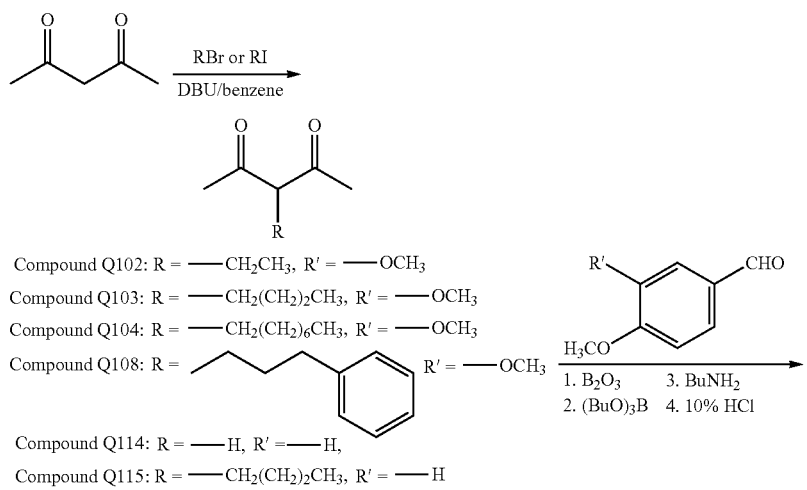

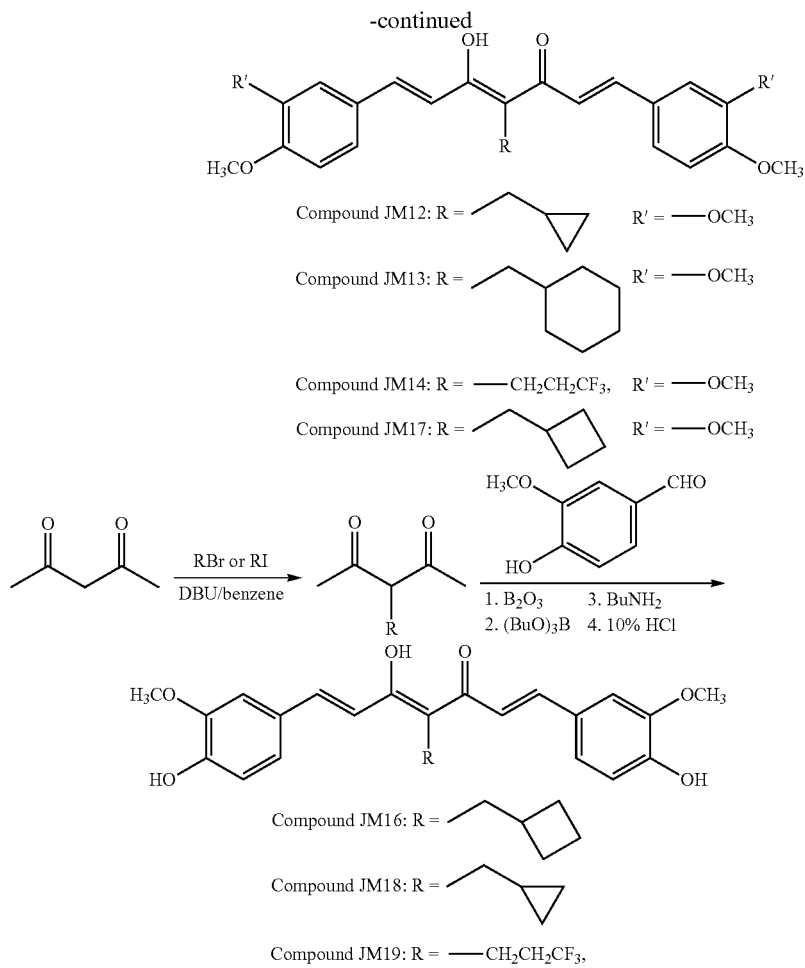

Compound Q102, a red needle crystal from EtOAc/hexanes, mp. 162-164° C. ESI MS m/z: 425.2 [M+H]$^+$; $^1$H NMR (300 MHz, CDCl3) δ: 7.73 (d, 2H, J=15.3 Hz, H-1,7), 7.23-7.19 (dd, 2H, J=8.1, 1.8 Hz, aromatic H), 7.09 (d, 2H, J=1.5 Hz, aromatic H), 6.96 (d, 2H, J=15.3 Hz, H-2, 6), 6.90 (d, 2H, J=8.1 Hz, aromatic ring H), 3.96 (s, 6H, OCH$_3$), 3.94 (s, 6H, OCH$_3$), 2.66-2.57 (m, 2H, —C$\underline{H}_2$CH$_3$), 1.24 (t, 2H, J=15.0, 6.0 Hz, —CH$_2$C$\underline{H}_3$).

Compound Q103, yellow crystal from EtOAc, mp. 125-126° C. ESI MS m/z: 453.2 [M+H]$^+$; $^1$H NMR (300 MHz, CDCl3) δ: 7.74-7.61 (2H, H-1,7), 7.21-7.06 (m, 4H, aromatic H), 6.99-6.71 (4H, H-2,6 and aromatic H), 3.94-3.92 (12H, —OCH$_3$), 2.57 (t, 1H, H-4), 1.51-1.22 (m, 6H, —CH$_2$CH$_2$CH$_2$—), 0.87 (3H, —CH$_3$).

Compound Q108, yellow solid from EtOAc, mp. 60-62° C. ESI MS m/z: 515.2 [M+H]$^+$; $^1$H NMR (300 MHz, CDCl3) δ: 7.72-7.60 (2H, H-1,7), 7.34-7.00 (m, 8H, aromatic H), 6.91-6.84 (3H, aromatic H), 6.82-6.68 (2H, H-2, 6), 3.95-3.92 (12H, —OCH$_3$), 3.46 (t, 1H, H-4), 2.80-2.52 (m, 2H, benzyl C$\underline{H}_2$), 2.12-1.84 (2H, —C$\underline{H}_2$—), 1.68-1.50 (2H, —CHC$\underline{H}_2$—).

Compound JM12, orange needles from EtOAc/hexanes; mp. 138-139° C.; ESI MS m/z: 451.2 [M+H]$^+$; $^1$H NMR (300 MHz, CDCl$_3$) δ: 7.72, 6.99 (both d, 2H each, J=15.3 Hz, H-1, 2, 6, 7), 7.21 (dd, 2H, J=1.8, 8.4 Hz, aromatic 5'-H), 7.08 (d, 2H, J=1.8 Hz, aromatic 2'-H), 6.90 (d, 2H, J=8.4 Hz, aromatic 6'-H), 5.30 (br. s, 1H, O$\underline{H}$), 3.95, 3.93 (both s, 6H each, OCH$_3$), 2.65 (d, 2H, J=6.0 Hz, C4-CH$_2$—), 0.95 (m, 1H, CH of cyclopropane), 0.95 (m, 1H, CH of cyclopropane), 0.51, 0.24 (both m, 2H each, CH$_2$ of cyclopropane).

Compound JM13, orange needles from EtOAc/hexanes; mp. 172-174° C.; ESI MS m/z: 493.2 [M+H]$^+$; $^1$H NMR (300 MHz, CDCl$_3$) δ: 7.71, 6.97 (both d, 2H each, J=15.3 Hz, H-1, 2, 6, 7), 7.20 (dd, 2H, J=1.8, 8.4 Hz, aromatic 5'-H), 7.08 (d, 2H, J=1.8 Hz, aromatic 2'-H), 6.92 (d, 2H, J=8.4 Hz, aromatic 6'-H), 5.30 (br. s, 1H, O$\underline{H}$), 3.95, 3.94 (both s, 6H each, OCH$_3$), 2.46 (d, 2H, J=6.9 Hz, C4-CH$_2$—), 1.90-1.00 (m, 11H, 1 CH and 5 CH$_2$ of cyclohexane).

Compound JM14, orange needles from EtOAc/hexanes; mp. 131-132° C.; ESI MS m/z: 493.2 [M+H]$^+$; $^1$H NMR (300 MHz, CDCl$_3$) δ: 9.87 (br.s, 1H, OH), 7.76, 6.90 (both d, 2H each, J=15.3 Hz, H-1, 2, 6, 7), 7.19 (dd, 2H, J=1.8, 8.4 Hz, aromatic 5'-H), 7.10 (d, 2H, J=1.8 Hz, aromatic 2'-H), 6.91 (d, 2H, J=8.4 Hz, aromatic 6'-H), 5.30 (br. s, 1H, O$\underline{H}$), 3.95, 3.94 (both s, 6H each, OCH$_3$), 2.86, 2.37 (both m, 2H each, C4-CH$_2$—CH$_2$—).

Compound JM16, orange amorphous; ESI MS m/z: 437.2 [M+H]$^+$; $^1$H NMR (300 MHz, CDCl$_3$, 2:1 tautomerism observed, data for major form listed) δ: 7.62, 6.71 (both d, 2H each, J=15.9 Hz, H-1, 2, 6, 7), 7.12 (dd, 2H, J=1.8, 8.4 Hz, aromatic 5'-H), 7.05 (d, 2H, J=1.8 Hz, aromatic 2'-H), 6.92 (d, 2H, J=8.4 Hz, aromatic 6'-H), 5.96 (br. s, 2H, OH X 2), 3.97 (s, 3H, OCH$_3$), 3.94 (s, 9H, OCH$_3$ X 3), 2.68 (d, 2H, J=6.9 Hz, C4-CH$_2$—), 2.19-1.59 (m, 7H, 1 CH and 3 CH$_2$ of cyclobutane).

Compound JM17, orange needle from EtOAc/hexanes, mp. 126-127° C.; ESI MS m/z: 465.2 [M+H]$^+$; $^1$H NMR (300 MHz, CDCl$_3$) δ: 7.72, 7.00 (both d, 2H each, J=15.3 Hz, H-1, 2, 6, 7), 7.21 (dd, 2H, J=1.8, 8.4 Hz, aromatic 5'-H), 7.09 (d, 2H, J=1.8 Hz, aromatic 2'-H), 6.92 (d, 2H, J=8.4 Hz, aromatic 6'-H), 3.96, 3.95 (both s, 6H each, OCH$_3$), 2.70 (d, 2H, J=6.9 Hz, C4-CH$_2$—), 2.08 (m, 2H, 1 CH$_2$ of cyclobutane), 1.83 (m, 4H, 2 CH$_2$ of cyclobutane).

Compound JM18, orange amorphous; ESI MS m/z: 423.2 [M+H]$^+$; $^1$H NMR (300 MHz, CDCl$_3$, 2:1 tautomerism observed, data for major form listed) δ: 7.65, 6.73 (both d, 2H each, J=15.9 Hz, H-1, 2, 6, 7), 7.12 (dd, 2H, J=1.8, 8.4 Hz, aromatic 5'-H), 7.05 (d, 2H, J=1.8 Hz, aromatic 2'-H), 6.92 (d, 2H, J=8.4 Hz, aromatic 6'-H), 3.93 (s, 12H, OCH$_3$ X 4), 2.71, 2.65 (both d, 1H each, J=6.0 Hz, C4-CH$_2$—), 0.95 (m, 1H, CH of cyclopropane), 0.51, 0.24 (both m, 2H each, CH$_2$ of cyclopropane).

Compound JM19, orange reddish needle from EtOAc/hexanes; mp. 153-154° C.; ESI MS m/z: 465.2 [M+H]$^+$; $^1$H NMR (300 MHz, CDCl$_3$) δ: 7.75, 6.88 (both d, 2H each, J=15.5 Hz, H-1, 2, 6, 7), 7.17 (dd, 2H, J=1.6, 8.5 Hz, aromatic 5'-H), 7.07 (d, 2H, J=1.6 Hz, aromatic 2'-H), 6.96 (d, 2H, J=8.5 Hz, aromatic 6'-H), 5.90 (s, 2H, O$\underline{H}$ X 2), 3.96 (s, 6H, OCH$_3$ X 2), 2.86, 2.35 (both m, 2H each, C4-CH$_2$—CH$_2$—).

Compound Q114, yellow crystalline solid from EtOAc/hexanes, mp. 166-167° C. ESI MS m/z: 337.0 [M+H]$^+$; $^1$H NMR (300 MHz, CDCl3) δ: 7.63 (d, 2H, J=16.1 Hz, H-1,7), 7.53-7.50 (m, 4H, aromatic H), 6.94-6.91 (m, 4H, aromatic H), 6.50 (d, 2H, J=16.1 Hz, H-2, 6), 5.79 (s, 1H, H-4), 3.85 (s, 6H, OCH$_3$).

Compound Q115, yellow crystal from EtOAc, mp. 142-143° C. ESI MS m/z: 393.1 [M+H]$^+$; $^1$H NMR (300 MHz, CDCl3) δ: 7.73 (d, 2H, J=15.6 Hz, H-1,7), 7.55-7.52 (4H, aromatic H), 6.99-6.92 (6H, H-2,6 and aromatic H), 3.86 (6H, —OCH$_3$), 2.55 (t, 1H, H-4), 1.53-1.40 (m, 6H, —CH$_2$CH$_2$CH$_2$—), 1.01 (t, 3H, —CH$_3$).

Synthesis of Compounds: JM4, JM20, and Q116.

Compounds JM4, JM20, Q116 structurally share the property of a (substituted)-triaryl system [three (substituted phenyl) propenal conjugation]. One of the purposes to synthesize these compounds is to study the effect of multi-phenyl propenal moiety on anti-AR and anti-prostate cancer activities. Compound JM4 were synthesized from a condensation of 3,4-dimethyoxybenzaldehyde with triacetylmethane as shown in Scheme 11.

Compounds JM20 and Q116 were synthesized with the same method described as JM4.

Compound JM20, red powder, mp. 165-167° C.; ESI MS m/z: 455.2 [M+H]$^+$; $^1$H NMR (300 MHz, d$_6$-DMSO) δ: 7.69 (d, 2H, J=15.6 Hz, H-1,7), 7.03 (d, 1H, J=16.2 Hz, C4 side chain —COCH═C$\underline{H}$—), 7.62-7.34 (m, 6H, aromatic ring H), 6.67 (d, 1H, J=15.6 Hz, C4 side chain —COC$\underline{H}$═CH—), 6.90-6.72 (m, 4H, aromatic H), 6.57 (d, 2H, J=15.9 Hz, H-2,6).

Compound Q116, yellow amorphous solid, mp. 70-72° C. ESI MS m/z: 497.1 [M+H]$^+$; $^1$H NMR (300 MHz, CDCl3) δ: 7.78 (d, 2H, J=15.3 Hz, H-1,7), 7.60 (d, 1H, J=15.6 Hz, C4 side chain —COCH═C$\underline{H}$—), 7.54-7.51 (2H, aromatic ring H), 7.47-7.44 (4H, aromatic ring H), 6.97 (d, 1H, J=15.6 Hz, C4 side chain —COC$\underline{H}$═CH—), 6.92-6.85 (6H, aromatic H), 6.71 (d, 2H, J=15.3 Hz, H-2,6), 3.84-3.82 (9H, —OCH$_3$).

Scheme 11

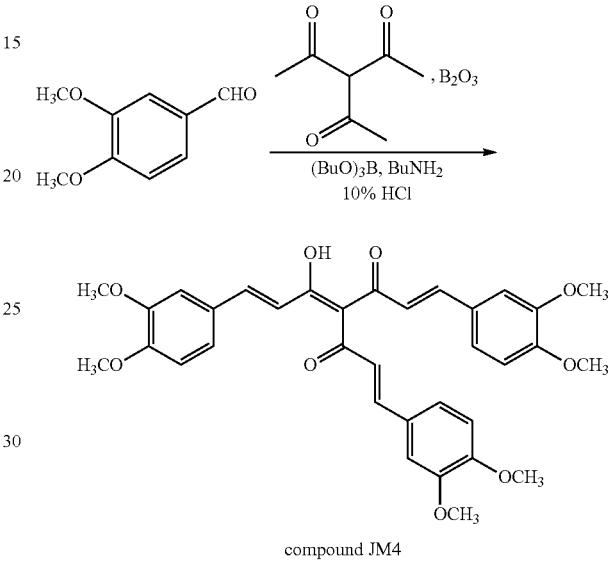

compound JM4

Synthesis of Compound: JM5.

Compound JM5 structurally containing four (substituted phenyl) propenal moieties was synthesized by reaction of ASC-J9 (18.9 g) with bromomethyl acetate (10.0 g) in anhydrous acetone (250 mL) in the presence of sodium carbonate (5.0 g) (Scheme 12). After heating to reflux for 80 h, the solid was filtered and the filtrate was concentrated under vacuum. The residue was subjected repeated silica gel column chromatography (n-hexanes:ethyl acetate-2:1) to afford the desired product and recovered starting material ASC-J9 (15 g). The obtained product was dissolved in 0.5 mL of ethyl acetate and was added dropwise to 5 mL of hexanes with stirring. After filtration and drying in vacuum to give compound JM5 (877 mg) as a yellow powder. Compound JM5 was also synthesized by reaction of ASC-J9 with bromomethyl methyl ether and sodium carbonate in anhydrous acetone in shorter time and with higher yield.

Scheme 12

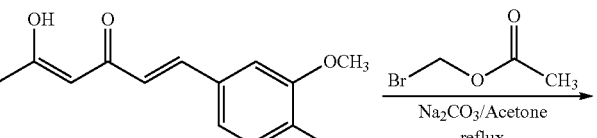

ASC-J9

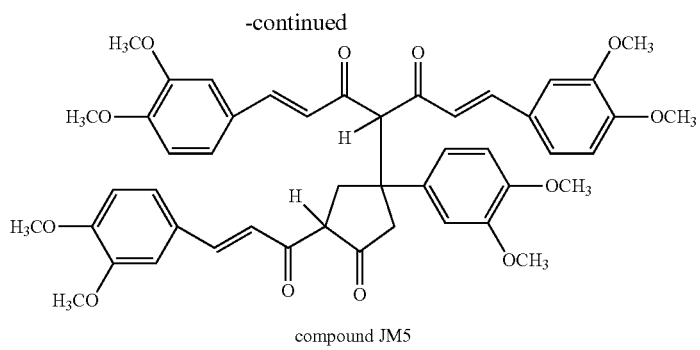

compound JM5

Analytical Data on Compound JM5 are Shown Below.

Yellow amorphous. mp. 111-114° C. ESI MS m/z: 804.87 [M+H]$^+$; $^1$H and $^{13}$C NMR data on 500 MHz Varian, (CDCl3) was listed in Table 1.

TABLE 1

$^1$H and $^{13}$C NMR Spectral Data of ASC-JM5.

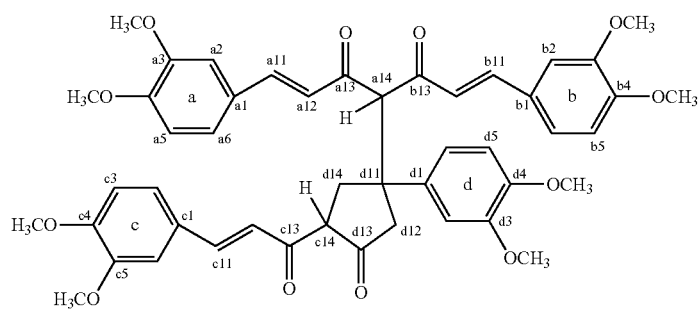 [SMILES: COc1ccc(/C=C/C(=O)C2CC(c3ccc(OC)c(OC)c3)(C(C(=O)/C=C/c3ccc(OC)c(OC)c3)C(=O)/C=C/c3ccc(OC)c(OC)c3)CC2=O)cc1OC]

| No. | Groups | δ $^1$H | δ $^{13}$C |
|---|---|---|---|
| a1 | Ar. =C | | 126.83 |
| a2 | Ar. =CH | 7.098 (d, J = 1.5) | 109.62 |
| a3, 4, b3, 4, c3, c4, d3, 4. | Ar. =C(OCH3) | *3.812 (s), 3.596, 3.708, 3.968, 3.950, 3.946, 3.857, 3.931 | 147.77, 147.93, 148.96, 149.15, 149.17, 151.25, 151.69, 151.87 |
| a5 | Ar. =CH | 6.878 (d, J = 8.0) | 110.82 |
| a6 | Ar. =CH | 7.167 (dd, J = 8.0, 1.5) | 123.31 |
| a11 | =CH | 7.732 (d, J = 15.5) | 143.25 |
| a12 | =CH | 7.017 (d, J = 15.5) | 116.46 |
| a13 | C=O | | 182.21 |
| a14 | —CH— | 4.317 (s) | 40.75 |
| b1 | Ar. =C | | 127.84 |
| b2 | Ar. =CH | 6.881 (d, J = 2.0) | 109.57 |
| b5 | Ar. =CH | 6.740 (d, J = 8.0) | 110.71 |
| b6 | Ar. =CH | 7.061 (dd, J = 8.0, 2.0) | 124.09 |
| b11 | =CH | 7.681 (d, J = 15.5) | 145.83 |
| b12 | =CH | 6.739 (d, J = 15.5) | 118.33 |
| b13 | C=O | | 196.29 |
| c1 | Ar. =C | | 126.80 |
| c2 | Ar. =CH | 7.055 (d, J = 1.5) | 109.80 |
| c5 | Ar. =CH | 6.878 (d, J = 8.5) | 110.82 |
| c6 | Ar. =CH | 7.195 (dd, J = 8.5, 1.5) | 123.84 |
| c11 | =CH | 7.60 (d, J = 15.5) | 144.71 |
| c12 | =CH | 7.038 (d, J = 15.5) | 119.03 |
| c13 | C=O | | 194.59 |
| c14 | —CH— | 4.317 (d, J = 7.5) | 40.69 |
| d1 | Ar. =C | | 133.03 |
| d2 | Ar. =CH | 6.653 (s) | 111.92 |
| d5 | Ar. =CH | 6.740 (d, J = 8.5) | 110.71 |
| d6 | Ar. =CH | 6.676 (d, J = 8.0) | 120.28 |
| d11 | —C— | | 68.86 |
| d12 | —CH$_2$ | 3.268 (d, J = 16.5), 3.352 (d, J = 16.5) | 24.13 |
| d13 | C=O | | 190.32 |
| d14 | —CH$_2$ | 2.734 (d, J = 19.5), 3.516 (dd, J = 19.5, 7.5) | 37.74 |

TABLE 1-continued $^{1}$H and $^{13}$C NMR Spectral Data of ASC-JM5.

[Structure diagram of ASC-JM5 showing four aryl groups (a, b, c, d) each with methoxy substituents connected through a central cyclopentane ring with carbonyl groups]

| No. | Groups | δ $^{1}$H | δ $^{13}$C |
|---|---|---|---|
| a3, 4, b3, 4, c3, c4, d3, 4. | —OCH$_3$ | 3.596 (s), | 55.40 |
| | | 3.708 (s), 3.812 (s), | 55.59 |
| | | 3.857 (s), 3.946 (s), | 55.87 |
| | | 3.931 (s), 3.950 (s), | 55.94 |
| | | 3.968 (s) | 56.05 |

*1H data of the methoxy protons

Synthesis of Compounds: Q110 and Q111.

In order to study the contribution of the length of the conjugation bridge to the AR activity, compound Q110 with a four-conjugated-double bond linker and compound Q111 with a five-conjugated-double bond linker were synthesized and illustrated in Scheme 13. Compound Q110 was synthesized starting from 1,2-dimethoxy-4-propylbenzene. To a solution of 3-(3, 4-dimethoxypheny) propane in dry dioxane was added with DDQ (3.1 eq.) and catalytic amount of acetic acid. The mixture was sonicated for 2 h with TLC monitoring. After completion of the reaction, the solid was filtered out and the filtration was concentrated. The residue was dissolved in EtOAc and washed with water, 2% NaHCO$_3$, and brine. The organic extract was dried over Na$_2$SO$_4$ and concentrated to afford a crude as yellow-brownish solid, which was purified with neutral alumina column chromatography and eluted with hexanes-ethyl acetate mixture to give a light yellow solid, 3,4-dimethoxycinnamaldehyde in 60% yield (B. P. Joshi et al., Tetrahedron, 62, 2590-2593, 2006). A solution of 2,4-petanedione (3 eq.) and B$_2$O$_3$ (1 eq.) in EtOAc was stirred at 40° C. for 0.5 h, 3,4-dimethoxycinnamaldehyde (1 eq.) and tributyl borane (1 eq.) were added. The resulting reaction mixture was stirred at 40° C. for 0.5 h. Butylamine (1.2 eq.) in EtOAc was added dropwise at the temperature and stirred at 40° C. for 16 h. To the red reaction mixture, 1% HCl aq was added and the mixture was stirred to 60° C. for 1 h. After cooling to rt, the aqueous was separated and the organic was washed with water to pH~7 and dried over Na2SO4. The crude was purified by silica gel flash column chromatography to get the intermediate product 8-(3,4-Dimethoxy-phenyl)-4-hydroxy-octa-3,5,7-trien-2-one as an off-white solid. A solution of the intermediate (1 eq.) and B$_2$O$_3$ (0.7 eq.) in EtOAc was stirred at 70° C. for 0.5 h. 3,4-dimethoxybenzaldehyde (1 eq.) and trubutyl borane (1 eq.) were added and the reaction mixture was stirred at 70° C. for 0.5 h. Piperidine (1.2 eq.) in EtOAc was added dropwise and the reaction mixture was stirred at 88-90° C. for 1 h. After cooling to 60° C., 1% HCl aq was added and the mixture was stirred at 60° C. for 0.5 h. The reaction mixture was worked-up by following the procedure described above and the crude was purified by silica gel column chromatography to afford the desired product Q110 as a red solid. Amorphous, mp. 65-68° C., ESI MS m/z: 423.1 [M+H]$^+$; $^1$H NMR (300 MHz, CDCl3) δ: 7.64-7.58 (d, 2H, H-1 and 2), 7.16-7.02 (4H, aromatic ring H and trans double bond H), 6.90-6.82 (4H, aromatic ring H), 6.53-6.48 (1H, trans double bond H), 6.18-6.12 (1H, trans double bond H), 5.75 (s, 1H, H-4), 3.94-3.92 (12H, —OCH$_3$).

Compound Q111 was synthesized by reaction of 8-(3,4-Dimethoxy-phenyl)-4-hydroxy-octa-3,5,7-trien-2-one (3) with 3,4-dimethoxycinnamaldehyde (2) as described in the synthesis of Q110 (Scheme 13). A red amorphous solid was afforded, mp. 187-9° C. ESI MS m/z: 449.1 [M+H]$^+$; $^1$H NMR (300 MHz, CDCl3) δ: 7.49-7.40 (d, 2H, H-1 and 11), 7.06-7.02 (4H, aromatic ring H), 6.87-6.81 (2H, aromatic ring H, and 4H for trans double bond H), 6.17-6.12 (2H, trans double bond H), 5.75 (s, 1H, H-4), 3.94-3.92 (12H, —OCH$_3$).

Scheme 13

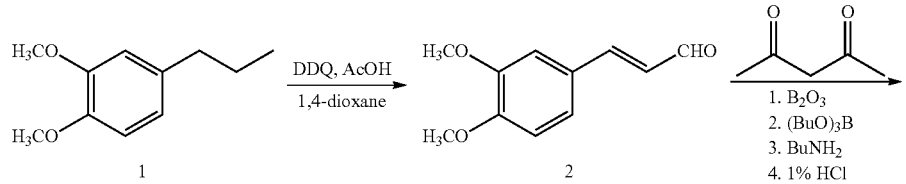

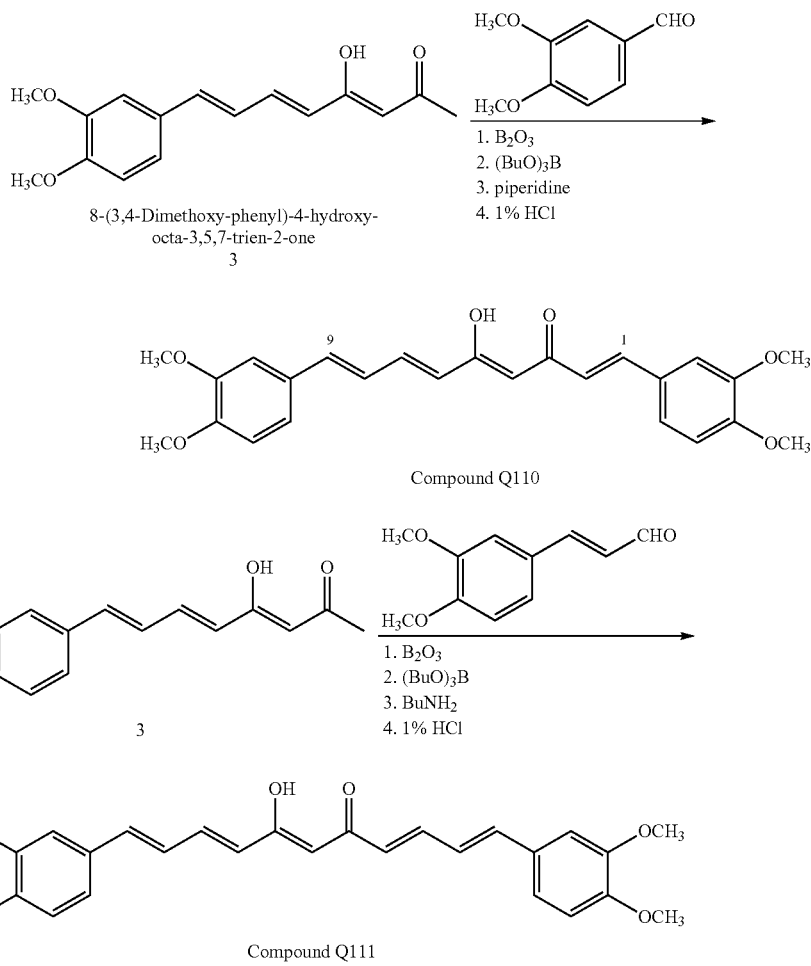

Example 2

Detecting Biological Effects of Compounds Having at Least One (3,4-Alkoxy or Hydroxy Substituted Phenyl)-Propenal Moiety on Human Androgen Receptor (AR) and Androgen/AR-Mediated Activity Representative ASC compounds and monomers were tested for their activity to block androgen/AR-induced functions. A cell growth assay using human prostate cancer cells, either LNCaP or CWR22Rv1, was applied in the studies. Functional AR proteins are expressed in both cancer cell lines; whereas the growth of LNCaP cells is DHT dependant, but the growth of CWR22Rv1 cells, derived from a relapsed hormone-refractory tumor, was not. In addition, Western Blot analysis were performed by testing monomers, and some representative new compounds in prostate cancer cells to demonstrate that compounds with at least one (4-hydroxy-3-methoxy-phenyl)-propenal moiety are capable of reducing AR protein expression levels and inhibiting cancer cell growth in vitro.

In Vitro Cell Growth Assays Using Human Prostate Cancer Cell Lines, LNCaP and CWR22Rv1

The MTT cell proliferation assay was applied in the present invention to detect the capability of compounds to suppress or inhibit prostate cancer cells growth. The MTT assay, which is a method widely used to detect proliferation of culture cells and is relied upon the conversion of a colorless substrate to reduced tetrazolium by a mitochondrial dehydrogenase (possessed by all viable cells), and has been demonstrated previously (Su et al., 1999) to assess the growth of various tissue-cultured cells. Briefly, $1 \times 10^3$ LNCaP or CWR22Rv1 cells suspended in complete medium were plated into each well of a 96-well Microtest III tissue culture plate (Falcon, N.J.). Two days later, the medium was replaced with RPMI-1640 medium containing 10% charcoal/dextran-deprived FBS (hormone-deprived fetal bovine serum). Testing compounds were added to the medium at indicated concentrations with or without 1 nM DHT and cells were cultured for 5 days in an incubator (at 37° C.). MTT substrate solution (5 mg/ml in PBS) in 1/10 of volume was added to the cells in each well at 2 hours before harvesting. After 2 hour incubation, the plates were centrifuged (10 min at 1,000 rpm) and the supernatant from each well was carefully removed. A 100 µl of lysis buffer (50% dimethyl formamide, 5% sodium dodecyl sulphate, 0.35 M acetic acid, and 50 mM HCl) was added to each well to lyse the cells and dissolved tetrazolium in each well. The relative quantity of enzyme activity from each well was measured based on absorbance read at a wavelength of 450 nm using a Bio-RAD BenchMark microplate reader. Data derived from the MTT assay were also verified by the actual cell count and cell morphology on a separate plate set up in parallel. Data from this parallel plate demonstrated a positive relationship between the quantity of enzyme activity and the number of viable cells in the well.

Western Blot Analysis of AR Protein Expression Levels in Prostate Cancer Cells

A widely used Western Blotting analysis was employed to measure AR protein expression level. Human prostate cancer cells, LNCaP and CWR22Rv1, both express high levels of AR proteins and were used in this study. In this invention representative ASC compounds were tested in Western blot assay to evaluate their activity in reducing AR expression; and the assays were carried out in either the presence or absence of dihydrotestosterone (DHT, 1 nM). After cells were incubated with testing compounds for the designated time, they were harvested and lysed according to Western Blot techniques known in the biochemical arts. Details of Western Blotting analysis method have been published previously (Su et al., 1999). Briefly, cells were harvested either in 2× sodium dodecyl sulphate/polyacrylamide gel electrophoresis (SDS/PAGE) loading buffer or in Radio-Immunoprecipitation Assay (RIPA) lysis buffer strengthened with 10 µg/ml of benzamidine, 10 µg/ml of trypsin inhibitor, and 1 mM of phenylmethylsulfonyl fluoride. A sample of total protein (approximately 40 µg) from each cell lysate was separated by electrophoresis on a SDS/PAGE gel. After separation by electrophoresis, the proteins were transferred from the gel to a nitrocellulose membrane following the standard procedures. The membrane was then incubated with 10% non-fat milk in phosphate-buffered saline supplemented with 0.1% Tween-20 (PBST) for 1 hour and then followed with an overnight incubation with a primary human AR-specific antibody (purchased from BD-PharMingen) at 4° C. After incubation, the membrane was rinsed with PBST buffer three times; 10 min each time; an alkaline phosphatase-conjugated secondary antibody was then added and incubated for 1 hour at room temperature. After second antibody incubation, membrane was again rinsed with PBST, and AR protein signal in the membrane was visualized by adding alkaline phosphatase substrates, bromochloroindolyl phosphate and nitro blue tetrazolium to the membrane. To assure that an equal amount of protein from each sample was analyzed, a portion of the membrane was stained with a specific antibody for a house keeping protein β-actin (Santa Cruz Biotechnology) and actin signal was revealed with a second antibody as described above. The protein signal intensity (shown as colour band on the membrane) was measured using densitometer and analysed by using NIH Image J software (NIH 1.33). The quantity of AR protein was calculated by normalizing the quantity of AR to the quantity of β-actin in each sample and data are expressed in relative quantity.

Detection of AR Degradation Using a Cycloheximide Chasing Assay Method:

AR protein "degradation" in prostate cancer cells was measured by using cycloheximide (a protein synthesis inhibitor) chasing assay method. Briefly, LNCaP cells were incubated with testing ASC compound at the designated concentrations for 24 hours. Subsequently, cycloheximide was added to the cells at a concentration of 15 µg/ml to block new protein synthesis. After incubation, cells were harvested at designated time periods and the resultant change in AR protein levels were analysed using Western Blot analysis as described above.

Example 3

Preparation of Compounds and Derivatives having (1E, 6E)-1,7-bis-(substituted phenyl)-4,4-disubstituted-hepta-1,6-diene-3,5-dione or (1E, 10E)-1,11-bis(substituted phenyl)-6,6-disubstituted undeca-1,3,8,10-tetraene-5,7-dione structural scaffold Chemical Synthesis:

Melting points were determined using a Fisher-John melting point apparatus without calibration. Proton Nuclear Magnetic Resonance ($^1$H NMR) and $^{13}$C NMR spectra were measured on Inova 400 spectrometers with tetramethylsilane as the internal standard. Chemical shifts were reported in δ (ppm). Mass spectra (MS) were obtained on a Shimadzu LCMS-2010. A CombiFlash chromatographic system was performed over Grace silica gel cartridge for general separation and purification. Preparative thin layer chromatography using silica gel plates (Kieselgel 60, F254, 1.00 mm) were also used for separation and purification. Precoated silica gel plates (Kieselgel 60, F254, 0.25 mm) were used for thin layer chromatography (TLC) analysis. All reagents and solvents were purchased from Aldrich, Fisher, VWR, or other venders.

Synthesis of Compounds 1-8, 22, 24, 28, 29, 31

Compounds 1-8, 22 were synthesized with a general procedure as illustrated in Scheme 14. An example to make the compound 2 was described as below. To a solution of JM17 (5.0 g) in dry acetone (50 mL) was added methyl iodide (2.5 ml) and K$_2$CO$_3$ (5.0 g). The reaction mixture was refluxed and stirred for 2 days with TLC monitoring. The reaction mixture was cooled down and filtered to remove inorganic powder then vacuum evaporated. The obtained crude was purified by silica gel column chromatography eluted by hexane and EtOAc mixture to get the desired product.

Compound 24 was synthesized by hydrolysis of 22 with trimethyltin hydroxide (10 eq.) in 1,2-dichloromethane (Scheme 1). The mixture was heated at 80° C. for 8 h or with TLC monitoring. After removal of the solvent the residue was dissolved in EtOAc and washed with 5% HCl aq. (×3). The organic was then washed with brine (×2), dried over Na$_2$SO$_4$, filtered and concentrated. The obtained crude was purified by preparative TLC to give the desired product.

Scheme 14
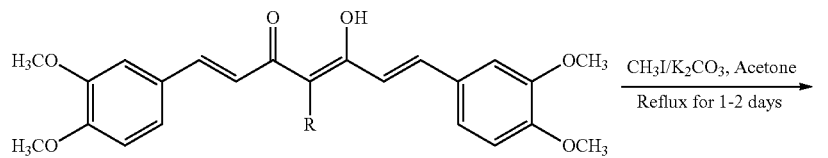
JM12, R = CH₂—▷
JM17, R = CH₂—□
3, R = CH₂—⬠
JM13, R = CH₂—⬡
Q49, R = CH₂—C(O)N(C₂H₅)₂
Q77, R = CH₂—C(O)N(CH₃)₂
Q103, R = (CH₂)₃CH₃
Q95, R = CH₂—C(O)OC₂H₅
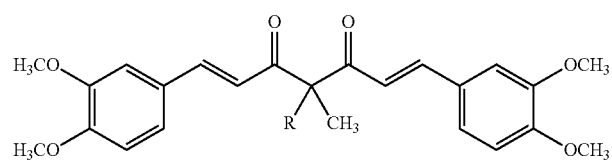
1, R = CH₂—▷
2, R = CH₂—□
4, R = CH₂—⬠
5, R = CH₂—⬡
6, R = CH₂—C(O)N(C₂H₅)₂
7, R = CH₂—C(O)N(CH₃)₂
8, R = (CH₂)₃CH₃
22, R = CH₂—C(O)OC₂H₅
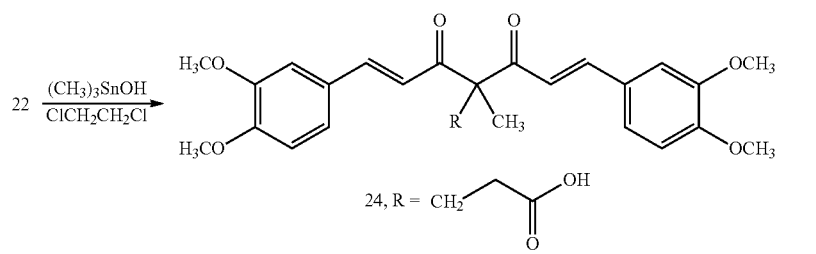
24, R = CH₂—C(O)OH
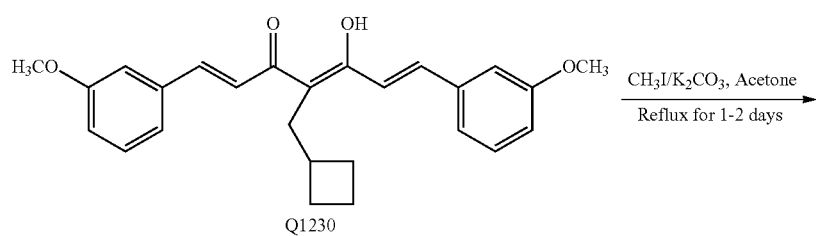
Q1230

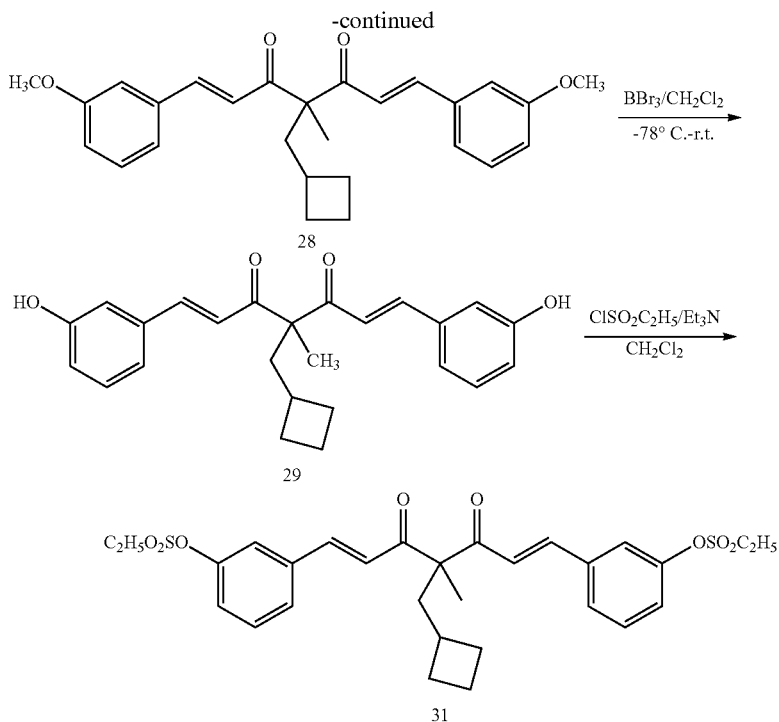

Compound 1, pale yellow amorphous. ESI MS m/z: 465.2 [M+H]$^+$. $^1$H NMR (400 MHz, CDCl$_3$) δ: 7.66 (d, 2H, J=15.6 Hz, H-1,7), 7.10 (dd, 2H, J=2.0, 8.4 Hz, aromatic H-6'), 6.97 (d, 2H, J=2.0 Hz, aromatic H-2'), 6.81 (d, 2H, J=8.4 Hz, aromatic H-5'), 6.63 (d, 2H, J=15.6 Hz, H-2,6), 3.87 (12H, OCH$_3$ X 4), 1.97 (d, 2H, J=6.4 Hz, CH$_2$—C4), 1.53 (s, 3H, CH$_3$—C4), 0.6-0.03 (m, 5H of cyclopropane).

Compound 2, white-yellow crystal, mp 161-162° C. ESI MS m/z: 479.2 [M+H]$^+$. $^1$H NMR (400 MHz, CDCl$_3$) δ: 7.64 (d, 2H, J=15.2 Hz, H-1,7), 7.09 (dd, 2H, J=2.6, 8.4 Hz, aromatic H-6'), 6.96 (d, 2H, J=2.0 Hz, aromatic H-2'), 6.80 (d, 2H, J=8.4 Hz, aromatic H-5'), 6.59 (d, 2H, J=15.2 Hz, H-2,6), 3.87 (12H, OCH$_3$ X 4), 3.0-1.6 (m, 7H of cyclobutane), 1.39 (s, 3H, CH$_3$—C4), 1.22 (t, 2H, J=6.9 Hz, CH$_2$—C4).

Compound 4, pale yellow amorphous. ESI MS m/z: 493.2 [M+H]$^+$. $^1$H NMR (400 MHz, CDCl$_3$) δ: 7.64 (d, 2H, J=15.2 Hz, H-1,7), 7.09 (dd, 2H, J=2.6, 8.4 Hz, aromatic H-6'), 6.96 (d, 2H, J=2.0 Hz, aromatic H-2'), 6.80 (d, 2H, J=8.4 Hz, aromatic H-5'), 6.59 (d, 2H, J=15.2 Hz, H-2,6), 3.87 (12H, OCH$_3$ X 4), 3.0-1.6 (m, 7H of cyclopentane), 1.39 (s, 3H, CH$_3$—C4), 1.22 (t, 2H, J=6.9 Hz, CH$_2$—C4).

Compound 5, pale yellow crystal, mp 128-129° C. ESI MS m/z: 507.2 [M+H]$^+$. $^1$H NMR (400 MHz, CDCl$_3$) δ: 7.63 (d, 2H, J=15.6 Hz, H-1,7), 7.10 (dd, 2H, J=2.6, 8.4 Hz, aromatic H-6'), 6.97 (d, 2H, J=2.0 Hz, aromatic H-2'), 6.81 (d, 2H, J=8.4 Hz, aromatic H-5'), 6.65 (d, 2H, J=15.6 Hz, H-2,6), 3.87 (12H, OCH$_3$ X 4), 1.97 (d, 2H, J=5.6 Hz, CH$_2$—C4), 1.65-0.85 (m, 11H of cyclohexane), 1.46 (s, 3H, CH$_3$—C4).

Compound 6, off-white crystal, ESI MS m/z: 524.3 [M+H]$^+$. $^1$H NMR (400 MHz, CDCl$_3$) δ: 7.63 (d, 2H, J=15.6 Hz, H-1,7), 7.09 (dd, 2H, J=2.0, 8.0 Hz, aromatic H-6'), 6.98 (d, 2H, J=2.0 Hz, aromatic H-2'), 6.80 (d, 2H, J=15.6 Hz, H-2,6), 6.80 (d, 2H, J=8.0 Hz, aromatic H-5'), 3.85 (12H, OCH$_3$ X 4), 3.39-3.28 (m, 4H, —N(CH$_2$CH$_3$)$_2$, 3.12 (s, 2H, C4-CH$_2$CO), 1.62 (s, 3H, CH$_3$—C4), 1.20 (t, 3H, J=7.2 Hz, —N(CH$_2$CH$_3$)$_2$), 1.04 (t, 3H, J=7.2 Hz, —N(CH$_2$CH$_3$)$_2$.

Compound 7, off-white crystal, ESI MS m/z: 496.4 [M+H]$^+$. $^1$H NMR (400 MHz, CDCl$_3$) δ: 7.63 (d, 2H, J=15.6 Hz, H-1,7), 7.09 (dd, 2H, J=8.4 Hz, aromatic H-6'), 6.97 (s, 2H, aromatic H-2'), 6.81 (d, 2H, J=15.6 Hz, H-2,6), 6.80 (d, 2H, J=8.4 Hz, aromatic H-5'), 3.85 (12H, OCH$_3$ X 4), 3.17 (s, 2H, C4-CH$_2$CO), 3.06 (s, 3H, —N(CH$_3$)$_2$), 2.88 (s, 3H, —N(CH$_3$)$_2$), 1.64 (s, 3H, CH$_3$—C4).

Compound 8, light yellow crystal, ESI MS m/z: 467.2 [M+H]$^+$. $^1$H NMR (400 MHz, CDCl$_3$) δ: 7.64 (d, 2H, J=15.6 Hz, H-1,7), 7.09 (d, 2H, J=8.4 Hz, aromatic H-6'), 6.98 (d, 2H, J=2.0 Hz, aromatic H-2'), 6.80 (d, 2H, J=8.4 Hz, aromatic H-5'), 6.63 (d, 2H, J=15.6 Hz, H-2,6), 3.86 (12H, OCH$_3$ X 4), 2.00-1.96 (m, 2H, —CH$_2$(CH$_2$)$_2$CH$_3$), 1.42 (s, 3H, CH$_3$—C4), 1.34-1.27 (m, 2H, CH$_2$(CH$_2$)$_2$CH$_3$), 1.16-1.10 (m, 2H, —CH$_2$(CH$_2$)$_2$CH$_3$), 0.85 (t, 3H, J=6.8 Hz, —CH$_2$(CH$_2$)$_2$CH$_3$).

Compound 22, yellow amorphous, ESI MS m/z: 511.2 [M+H]$^+$, 533.2 [M+Na]$^+$. $^1$H NMR (400 MHz, CDCl$_3$) δ: 7.65 (d, 2H, J=15.2 Hz, H-1,7), 7.09 (dd, 2H, J=2.0, 8.0, Hz, aromatic H-6'), 6.96 (d, 2H, J=2.0 Hz, aromatic H-2'), 6.79 (d, 2H, J=8.4 Hz, aromatic H-5'), 6.61 (d, 2H, J=15.2 Hz, H-2,6), 4.10-4.05 (m, 2H, OCH$_2$CH$_3$), 3.85 (s, 12H, OCH$_3$ X 4), 2.36-2.19 (m, 4H, C4-CH$_2$CH$_2$CO—), 1.42 (s, 3H, CH$_3$—C4), 1.20 (t, 3H, J=7.6 Hz, OCH$_2$CH$_3$).

Compound 24, yellow amorphous, ESI MS m/z: 483.18 [M+H]$^+$, 505.15 [M+Na]$^+$. $^1$H NMR (400 MHz, CDCl$_3$) δ: 7.66 (d, 2H, J=15.6 Hz, H-1,7), 7.09 (dd, 2H, J=1.6, 8.0 Hz, aromatic H-6'), 6.97 (d, 2H, J=1.6 Hz, aromatic H-2'), 6.80 (d, 2H, J=8.0 Hz, aromatic H-5'), 6.61 (d, 2H, J=15.6 Hz, H-2,6), 3.86 (s, 12H, OCH$_3$ X 4), 2.36-2.24 (m, 4H, C4-CH$_2$CH$_2$CO—), 1.43 (s, 3H, CH$_3$—C4).

Compound 28 was synthesized by methylation of Q1230 with methyl iodide in acetone using potassium carbonate as described above (Scheme 1). Demethylation of 28 with boron tribromide (3 eq.) in methylene chloride and purification through combiflash column chromatograph yielded the Compound 29. Treatment of 29 with ethanesulfonyl chloride (3 eq.) in the presence of triethyl amine afforded the Compound 31.

Compound 28, light yellow amorphous, ESI MS m/z: 419.3 [M+H]$^+$. $^1$H NMR (400 MHz, CDCl$_3$) δ: 7.65 (d, 2H, J=15.6 Hz, H-1,7), 7.24 (t, 2H, J=8.0 Hz, aromatic H), 7.07 (d, 2H, J=7.6 Hz, aromatic H), 6.98 (d, 2H, J=2.4 Hz, aromatic H), 6.89 (dd, 2H, J=2.8, 8.4 Hz, H-2,6), 6.71 (d, 2H, J=15.6 Hz, H-2,6), 3.78 (s, 6H, OCH$_3$ X 2), 2.28-2.21 (m, 1H, cyclobutane), 2.13 (d, 2H, 11.6 Hz, C4-CH$_2$), 1.99-1.93 (m, 2H, cyclobutane), 1.80-1.60 (m, 4H, cyclobutane), 1.39 (s, 3H, C4-CH$_3$).

Compound 29, yellow amorphous, ESI MS m/z: 391.3 [M+H]$^+$. $^1$H NMR (400 MHz, CDCl$_3$) δ: 7.62 (d, 2H, J=15.6 Hz, H-1,7), 7.19 (t, 2H, J=8.0 Hz, aromatic H), 7.08-6.96 (m, 4H, aromatic H), 6.89-6.83 (m, 2H, aromatic H), 6.89 (dd, 2H, J=2.8, 8.4 Hz, H-2,6), 6.70 (d, 2H, J=15.6 Hz, H-2,6), 2.27-2.19 (m, 1H, cyclobutane), 2.13-2.11 (m, 2H, C4-CH$_2$), 1.97-1.91 (m, 2H, cyclobutane), 1.79-1.54 (m, 4H, cyclobutane), 1.39 (s, 3H, C4-CH$_3$).

Compound 31, light yellow amorphous, ESI MS m/z: 575.4 [M+H]$^+$. $^1$H NMR (400 MHz, CDCl$_3$) δ: 7.68 (d, 1H, J=15.6 Hz, H-1), 7.64 (d, 1H, J=15.6 Hz, H-7), 7.51-7.35 (m, 6H, aromatic-H), 7.27 (d, br, 2H, J=8.0 Hz, aromatic H), 7.11 (d, 1H, J=15.6 Hz, H-2), 6.73 (d, 1H, J=15.6 Hz, H-6), 3.34-3.25 (m, 4H, OSO$_2$CH$_2$CH$_3$×2), 2.28-2.21 (m, 1H, cyclobutane), 2.17 (m, 2H, C4-CH$_2$), 1.99-1.93 (m, 2H, cyclobutane), 1.82-1.60 (m, 4H, cyclobutane), 1.57-1.51 (m, 6H, OSO$_2$CH$_2$CH$_3$×2), 1.40 (s, 3H, C4-CH$_3$).

Synthesis of Compounds 9-12

Compounds 9-12 were synthesized with a general procedure as illustrated in Scheme 15.

Chloroacetic acid (2 eq.) was dissolved in methylene chloride. To the solution was added a solution of DCC (1 eq.) in methylene chloride. The mixture was stirred at rt for 10 min, and a solution of DMAP (0.5 eq) and an appropriate amine in methylene chloride was added slowly. The reaction mixture was allowed to stir at rt overnight or with TLC monitoring. The solid was filtered and the filtrate was washed with water, 6N HCl, 6N NaOH and water. After drying over Na$_2$SO$_4$, and evaporating to remove solvent, the desired amide product was obtained without further purification. Reaction of the amide (1 eq.) with 2,4-pentanedione (1.5 eq.) in acetonitrile in the presence of DBU (1 eq.) at rt yielded a corresponding product 3-acetyl-4-oxopentanamide as illustrated in the Scheme 2. The resulting product (1 eq.) was then mixed the 3,4-dimethoxybenzaldehyde (2 eq.) in the presence of B$_3$O$_2$ (0.5 eq.), (BuO)$_3$B (2 eq.) and NH$_2$Bu (0.4 eq.) in DMA and the mixture was allowed to stir at 65° C. for 3-5 h with TLC monitoring. 1% HCl aqueous was added upon the reaction completion, and the resulting mixture was stirred at 65° C. for 1-2 hours. The mixture was then diluted with ethyl acetate and extracted with water twice or until pH~5. The ethyl acetate extract was dried over Na2SO4, filtered and concentrated. The crude was purified by crystallization from ethyl acetate or Combiflash colume chromatograph to give the desired product, such as compound 9 or 10. Reaction of 9 or 10 by following the procedure described in the Scheme 1 yielded the compounds 11 and 12.

Scheme 15

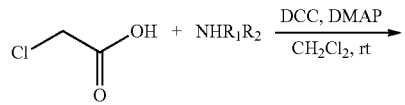

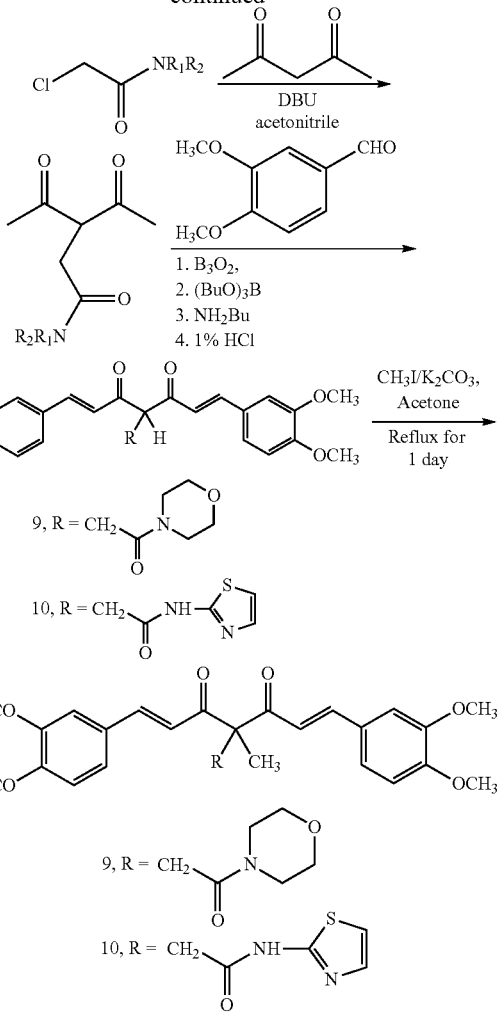

Compound 9, light-yellow crystalline solid, ESI MS m/z: 524.5 [M+H]$^+$. $^1$H NMR (400 MHz, CDCl$_3$) δ: 7.64 (d, 2H, J=15.6 Hz, H-1,7), 7.11 (dd, 2H, J=2.0, 8.4 Hz, aromatic H-6'), 7.02 (d, 2H, J=1.6 Hz, aromatic H-2'), 6.82 (d, 2H, J=8.4 Hz, aromatic H-5'), 6.76 (d, 2H, J=15.6 Hz, H-2,6), 3.87 (s, 6H, OCH$_3$ X 2), 3.84 (s, 6H, OCH$_3$ X 2), 3.70-3.65 (m, 4H, morpholine-H), 3.63-3.59 (m, 4H, morpholine-H), 3.57-3.52 (m, 1H, C4-H), 3.00 (d, 2H, J=6.8 Hz, C4-CH$_2$CO).

Compound 10, red-orange crystalline solid, ESI MS m/z: 551.6 [M+H]$^+$. $^1$H NMR (400 MHz, CDCl$_3$) δ: 7.68 (d, 2H, J=15.6 Hz, H-1,7), 7.43 (d, 1H, J=4.0 Hz, thiazole-H), 7.15 (dd, 2H, J=2.0, 8.4 Hz, aromatic H-6'), 7.01 (d, 2H, J=2.0 Hz, aromatic H-2'), 6.90 (d, 1H, J=4.0 Hz, thiazole-H), 6.83 (d, 2H, J=8.4 Hz, aromatic H-5'), 6.78 (d, 2H, J=15.6 Hz, H-2,6), 3.87 (s, 6H, OCH$_3$ X 2), 3.85 (s, 6H, OCH$_3$ X 2), 2.98 (s, 2H, C4-CH$_2$CO).

Compound 11, light yellow crystalline solid, ESI MS m/z: 538.6 [M+H]$^+$. $^1$H NMR (400 MHz, CDCl$_3$) δ: 7.65 (d, 2H, J=15.2 Hz, H-1,7), 7.09 (dd, 2H, J=2.0, 8.4 Hz, aromatic H-6'), 6.98 (d, 2H, J=2.0 Hz, aromatic H-2'), 6.80 (d, 2H, J=15.2 Hz, H-2,6), 6.80 (d, 2H, J=8.4 Hz, aromatic H-5'), 3.87 (s, 6H, OCH$_3$ X 2), 3.82 (s, 6H, OCH$_3$ X 2), 3.68-3.60 (m, 4H, morpholine-H), 3.56-3.53 (m, 4H, morpholine-H), 3.15 (s, 2H, C4-CH$_2$CO), 1.64 (s, 3H, CH$_3$—C4).

Compound 12, light yellow crystalline solid, ESI MS m/z: 551.6 [M+H]$^+$. $^1$H NMR (400 MHz, CDCl$_3$) δ: 7.69 (d, 2H, J=15.2 Hz, H-1,7), 7.45 (d, 1H, J=4.0 Hz, thiazole-H), 7.12 (dd, 2H, J=2.0, 8.4 Hz, aromatic H-6'), 6.99 (d, 2H, J=2.0 Hz, aromatic H-2'), 6.93 (d, 1H, J=4.0 Hz, thiazole-H), 6.81 (d, 2H, J=15.2 Hz, H-2,6), 6.81 (d, 2H, J=8.4 Hz, aromatic H-5'), 3.87 (s, 6H, OCH₃ X 2), 3.85 (s, 6H, OCH₃ X 2), 3.46 (s, 2H, C4-CH₂CO), 1.72 (s, 3H, CH₃—C4).

Synthesis of Compounds 13-19, 23, 25, 27

The compounds 13-19, 23 were synthesized with the general method as illustrated in Scheme 16. An example to make compound 14 was described as below. To a solution of JM17 (2.2 g) in acetonitrile (20 mL) was added N-Fluorodibenzenesulfonimide (1.5 g). The reaction mixture was stirred at room temperature for 1 day with TLC monitoring. The reaction mixture was vacuum evaporated and obtained crude was purified by silica gel column chromatography eluted by hexanes and EtOAc mixture to get the desired product.

Compound 25 was made by conversion of compound 23 through the method of making 24 from 22.

Compound 27 was synthesized starting from 4-hydroxy-3-methoxybenzaldehyde through general MOM protection (chloro-methoxy methane) and condensation reactions to make Q15M. Fluoridation of Q15M, the resulting compound (0.06 mM) was subjected a de-protection reaction with zinc bromide (ZnBr) (1.5 eq.) and propylthiol (3 eq.) in methylene chloride at rt for 30 min. During which time, a red solution was generated. Methylene chloride was added and the solution was stirred in an ice bath for 10 min. Sat. NaHCO₃ (0.3-0.5 mL) was added and the mixture was stirred in cold for 15 min. After filtration through celite, extraction with CH₂Cl₂, (×2), and purification through combiflash column chromatograph, the desired product was obtained.

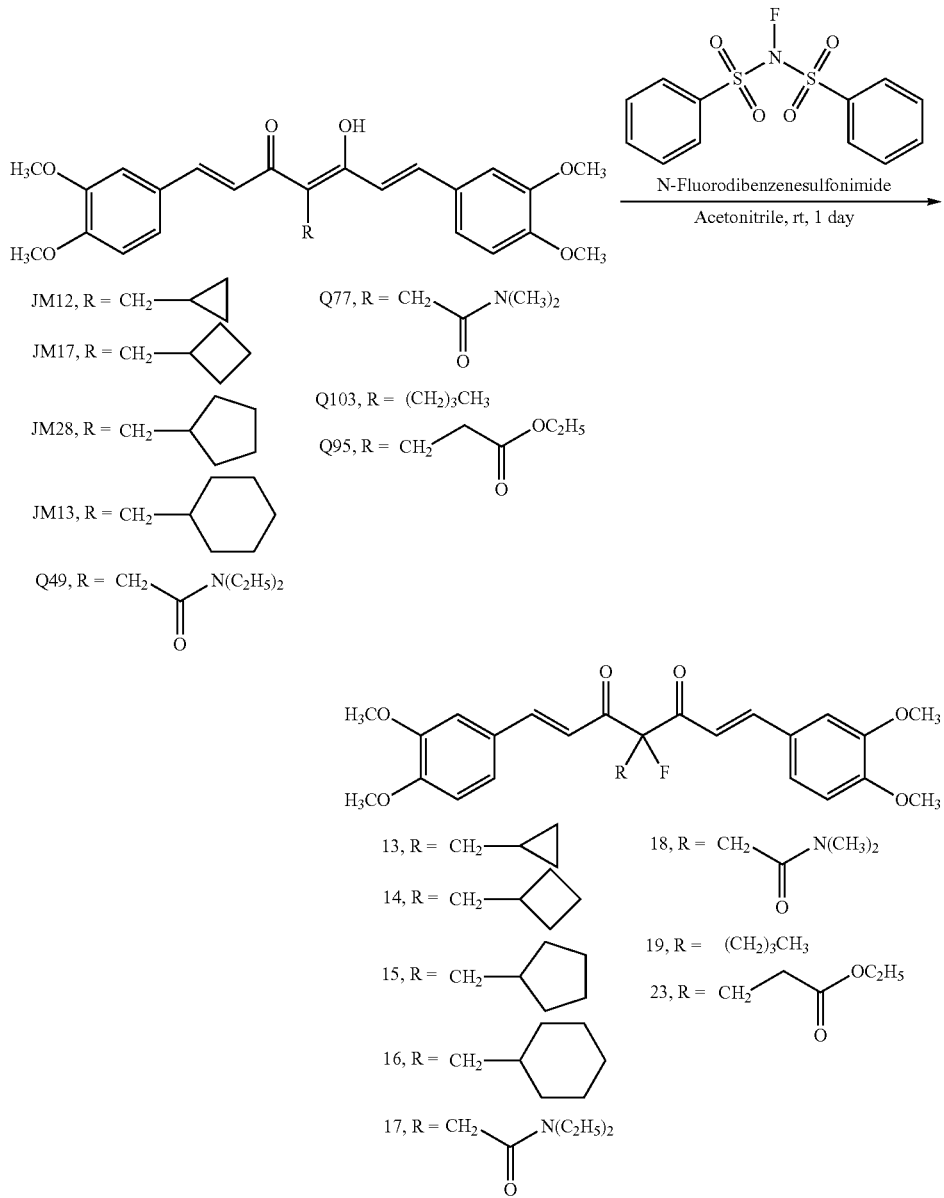

Scheme 16

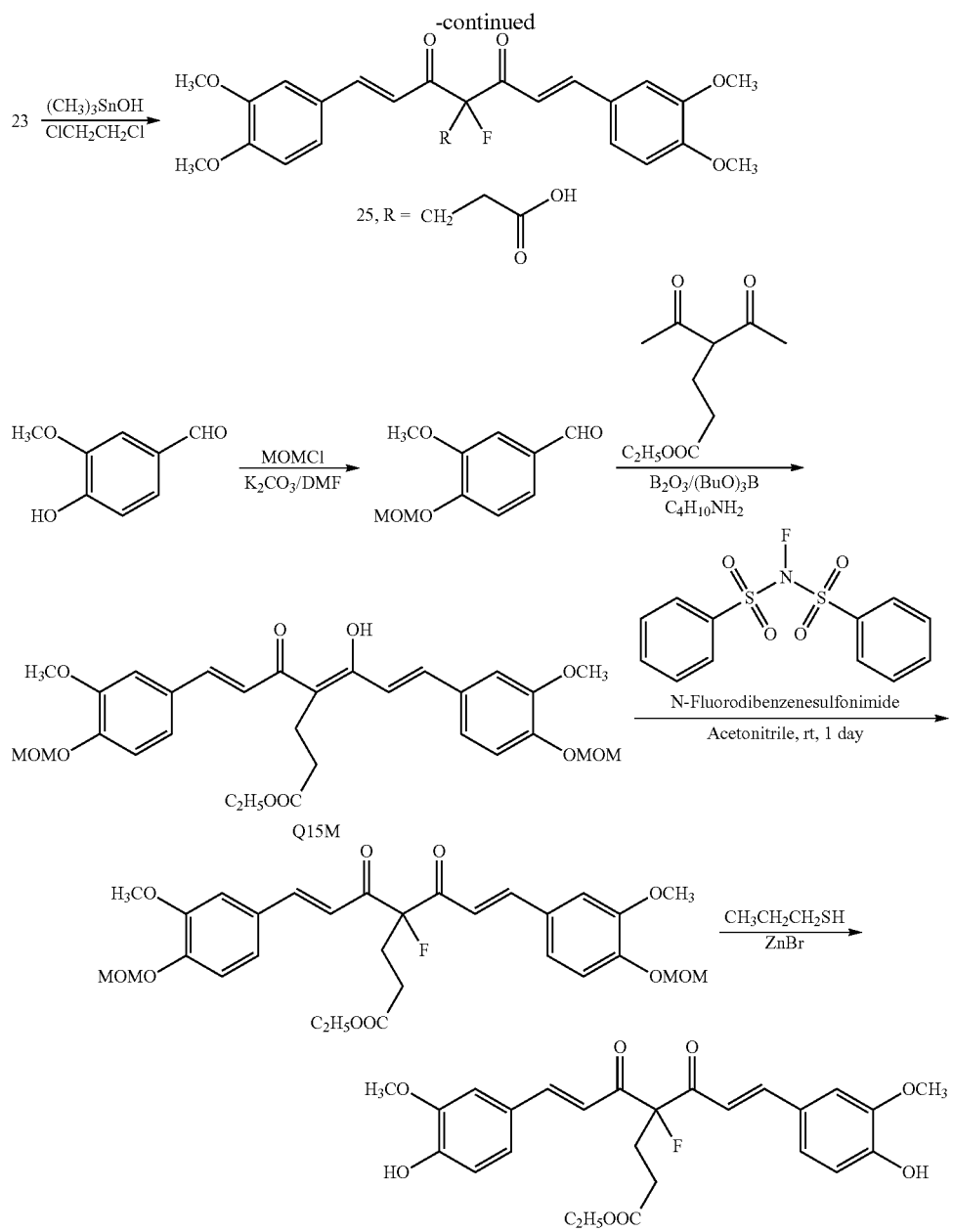

Compound 13, pale yellow crystal, mp 104-105° C. ESI MS m/z: 469.2 [M+H]+. 1H NMR (400 MHz, CDCl3) δ: 7.72 (d, 2H, J=15.6 Hz, H-1,7), 7.18 (dd, 2H, J=2.6, 8.4 Hz, aromatic H-6'), 7.09 (dd, 2H, $J_{H-F}$=2.4, 15.6 Hz, H-2,6), 7.08 (d, 2H, J=2.0 Hz, aromatic H-2'), 6.84 (d, 2H, J=8.4 Hz, aromatic H-5'), 3.91, 3.90 (both s, 6H each, OCH3 X 4), 2.20 (dd, 2H, J=7.0, 24.4 Hz, CH2—C4), 0.8-0.1 (m, 5H of cyclopropane).

Compound 14, pale yellow crystal, mp 98-100° C. ESI MS m/z: 483.2 [M+H]+. 1H NMR (400 MHz, CDCl3) δ: 7.70 (d, 2H, J=16 Hz, H-1,7), 7.17 (dd, 2H, J=2.6, 8.4 Hz, aromatic H-6'), 7.08 (d, 2H, J=2.0 Hz, aromatic H-2'), 7.05 (dd, 2H, $J_{H-F}$=2.8, 16 Hz, H-2,6), 6.84 (d, 2H, J=8.4 Hz, aromatic H-5'), 3.91, 3.89 (both s, 6H each, OCH3 X 4), 2.5-1.7 (m, 9H of methylcyclobutane).

Compound 15, pale yellow amorphous. ESI MS m/z: 497.2 [M+H]+. 1H NMR (400 MHz, CDCl3) δ: 7.70 (d, 2H, J=16 Hz, H-1,7), 7.17 (dd, 2H, J=2.6, 8.4 Hz, aromatic H-6'), 7.08 (d, 2H, J=2.0 Hz, aromatic H-2'), 7.05 (dd, 2H, $J_{H-F}$=2.8, 16 Hz, H-2,6), 6.84 (d, 2H, J=8.4 Hz, aromatic H-5'), 3.91, 3.89 (both s, 6H each, OCH3 X 4), 2.5-1.7 (m, 9H of methylcyclopentane).

Compound 16, pale yellow amorphous. ESI MS m/z: 511.2 [M+H]+. 1H NMR (400 MHz, CDCl3) δ: 7.71 (d, 2H, J=15.6 Hz, H-1,7), 7.17 (dd, 2H, J=2.0, 8.4 Hz, aromatic H-6'), 7.09 (d, 2H, J=2.0 Hz, aromatic H-2'), 7.08 (dd, 2H, $J_{H-F}$=2.0, 16 Hz, H-2,6), 6.84 (d, 2H, J=8.4 Hz, aromatic H-5'), 3.91, 3.89 (both s, 6H each, OCH3 X 4), 2.19 (dd, 2H, J=6.4, 24.8 Hz, CH2—C4), 1.8-0.9 (m, 11H of cyclohexane).

Compound 17, off-white crystal, ESI MS m/z: 528.5 [M+H]+. 1H NMR (400 MHz, CDCl3) δ: 7.73 (d, 2H, J=15.6 Hz, H-1,7), 7.24 (dd, 2H, J=2.4, 15.6 Hz, H-2,6), 7.19 (dd, 2H, J=1.6, 8.4 Hz, aromatic H-6'), 7.12 (d, 2H, J=2.0 Hz, aromatic H-2'), 6.85 (d, 2H, J=8.4 Hz, aromatic H-5'), 3.91 (s, 12H, OCH3 X 4), 3.48 (d, 2H, J=24.4 Hz, C4-CH2CO), 3.40-3.29 (m, 4H, —N(CH2CH3)2), 1.21 (t, 3H, J=7.2 Hz, —N(CH2CH3)2), 1.10 (t, 3H, J=7.2 Hz, —N(CH2CH3)2.

Compound 18, off-white crystal, ESI MS m/z: 500.4 [M+H]+. 1H NMR (400 MHz, CDCl3) δ: 7.71 (d, 2H, J=15.2 Hz, H-1,7), 7.20 (dd, 2H, J=2.4, 15.2 Hz, H-2,6), 7.17 (d, 2H, J=8.0 Hz, aromatic H-6'), 7.11 (s, 2H, aromatic H-2'), 6.83 (d, 2H, J=8.4 Hz, aromatic H-5'), 3.89 (s, 12H, OCH3 X 4), 3.47 (d, 2H, J=25.2 Hz, C4-CH2CO), 3.01 (s, 3H, —N(CH3)2), 2.92 (s, 3H, —N(CH3)2).

Compound 19, light yellow crystal, ESI MS m/z: 471.2 [M+H]+. 1H NMR (400 MHz, CDCl3) δ: 7.72 (d, 2H, J=15.6 Hz, H-1,7), 7.17 (dd, 2H, J=1.6, 8.4 Hz, aromatic 7.08 (d, 2H, J=2.0 Hz, aromatic H-2'), 7.06 (dd, 2H, J=2.8, 15.6 Hz, H-2,6), 6.84 (d, 2H, J=8.4 Hz, aromatic H-5'), 3.91 (s, 6H, OCH3 X 2), 3.90 (s, 6H, OCH3 X 2), 2.29-2.19 (m, 2H, —CH2(CH2)2CH3), 1.40-1.30 (m, 4H, CH2(CH2)2CH3), 0.88 (t, 3H, J=6.8 Hz, —CH2(CH2)2CH3).

Compound 23, yellow-orange amorphous, ESI MS m/z: 515.17 [M+H]+, 537.15 [M+Na]+. 1H NMR (400 MHz, CDCl3) δ: 7.73 (d, 2H, J=15.6 Hz, H-1,7), 7.17 (dd, 2H, J=2.0, 8.4, Hz, aromatic H-6'), 7.07 (d, 2H, J=2.0 Hz, aromatic H-2'), 7.03 (dd, 2H, J=2.8, 16.8 Hz, H-2,6), 6.84 (d, 2H, J=8.0 Hz, aromatic H-5'), 4.13-4.06 (m, 2H, OCH2CH3), 3.90 (s, 6H, OCH3 X 2), 3.89 (s, 6H, OCH3 X 2), 2.65-2.55 (m, 2H, C4-CH2CH2CO—), 2.43-2.39 (m, 2H, C4-CH2CH2CO—), 1.21 (t, 3H, J=6.4 Hz, OCH2CH3).

Compound 25, yellow amorphous, ESI MS m/z: 487.17 [M+H]+. 1H NMR (400 MHz, CDCl3) δ: 7.74 (d, 2H, J=15.6 Hz, H-1,7), 7.16 (d, 2H, J=8.4, Hz, aromatic H-6'), 7.07 (s, 2H, aromatic H-2'), 7.02 (d, 2H, J=16.8 Hz, H-2,6), 6.83 (d, 2H, J=8.4 Hz, aromatic H-5'), 3.90 (s, 6H, OCH3 X 2), 3.89 (s, 6H, OCH3 X 2), 2.64-2.48 (m, 4H, C4-CH2CH2CO—).

Compound 27, yellow-orange amorphous, ESI MS m/z: 487.28 [M+H]+. 1H NMR (400 MHz, CDCl3) δ: 7.72 (d, 2H, J=16.0 Hz, H-1,7), 7.15 (dd, 2H, J=1.6, 8.4 Hz, H-6'), 7.06 (d, 2H, J=2.0 Hz, aromatic H-2'), 7.01 (dd, 2H, J=2.4, 15.6 Hz, H-2,6), 6.89 (d, 2H, J=8.0 Hz, aromatic H-5'), 5.95 (s, 2H, phenol OH), 4.13-4.07 (m, 2H, OCH2CH3), 3.92 (s, 6H, OCH3 X 2), 2.62-2.55 (m, 2H, C4-CH2CH2CO—), 2.43-2.39 (m, 2H, C4-CH2CH2CO—), 1.21 (t, 3H, J=7.2 Hz, OCH2CH3).

Synthesis of Compounds 20-21

Compounds 20 and 21 were synthesized with the method as illustrated in the Scheme 17. To a solution of Q49 or Q77 (1 eq.) in THF was added Et3N (1.5 eq.). The mixture was cooled in an ice-bath and trifluoromethanesulfonyl chloride (1 eq.) in THF was added slowly. The reaction mixture was allowed to stir at rt (1 h) then heat to 50° C. for 5 hour or with TLC monitoring. The reaction was quenched by addition of ice water and ethyl acetate. After extracting with water followed by ethyl acetate, the crude was purified by Combiflash column chromatograph eluting with methylene chloride and ethyl acetate to get the desired product.

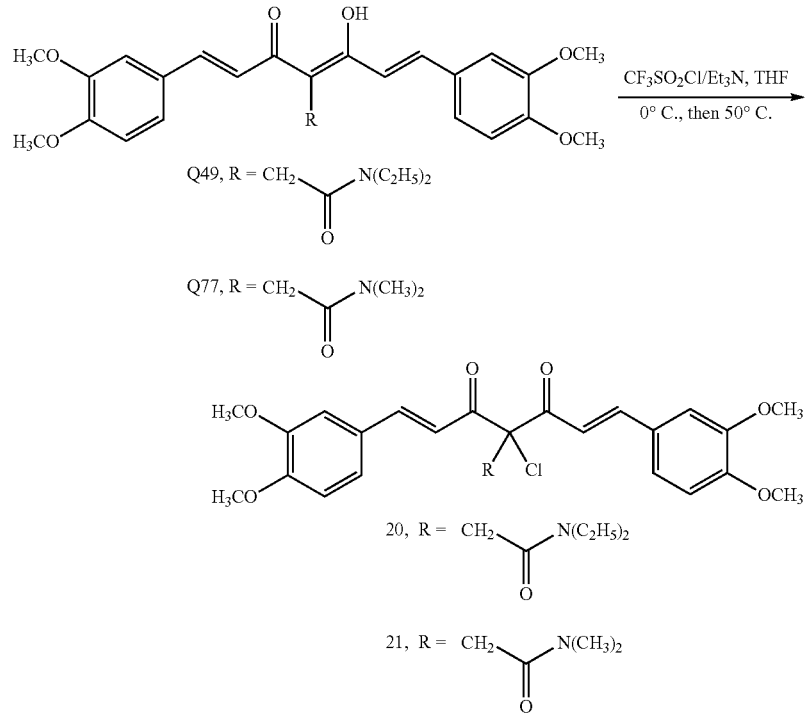

Scheme 17

Compound 20, off-white crystal, ESI MS m/z: 545.5 [M+H]+. 1H NMR (400 MHz, CDCl3) δ: 7.73 (d, 2H, J=15.6 Hz, H-1,7), 7.15 (d, 2H, J=15.6 Hz, H-2,6), 7.15-7.13 (m, 2H, aromatic H-6'), 7.04 (br, 2H, aromatic H-2'), 6.82 (d, 2H, J=8.4 Hz, aromatic H-5'), 3.88 (s, 6H, OCH3 X 2), 3.82 (s, 6H, OCH3 X 2), 3.60 (s, 2H, C4-CH2CO), 3.38-3.33 (m, 4H, —N(CH2CH3)2), 1.22 (t, 3H, J=6.8 Hz, —N(CH2CH3)2), 1.08 (t, 3H, J=6.8 Hz, —N(CH2CH3)2.

Compound 21, off-white crystal, ESI MS m/z: 516.4 [M+H]$^+$. $^1$H NMR (400 MHz, CDCl$_3$) δ: 7.69 (d, 2H, J=15.6 Hz, H-1,7), 7.18 (d, 2H, J=15.6 Hz, H-2,6), 7.14 (dd, 2H, J=3.6, 10.0 Hz, aromatic H-6'), 7.04 (d, 2H, J=2.0 Hz, aromatic H-2'), 6.82 (d, 2H, J=8.4 Hz, aromatic H-5'), 3.89 (s, 6H, OCH$_3$ X 2), 3.82 (s, 6H, OCH$_3$ X 2), 3.62 (s, 2H, C4-CH$_2$CO), 3.07 (s, 3H, —N(CH$_3$)$_2$), 2.92 (s, 3H, —N(CH$_3$)$_2$).

Synthesis of Compound 26

Compound 26 was synthesized from Q15M through methylation and deprotection (Scheme 18). The procedure was described above as making the compound 27. ESI MS m/z: 483.2 [M+H]$^+$, 506.2 [M+Na]$^+$. $^1$H NMR (400 MHz, CDCl$_3$) δ: 7.65 (d, 2H, J=16.0 Hz, H-1,7), 7.05 (dd, 2H, J=2.0, 8.4, Hz, aromatic H-6'), 6.96 (d, 2H, J=2.0 Hz, aromatic H-2'), 6.85 (d, 2H, J=8.0 Hz, aromatic H-5'), 6.59 (d, 2H, J=16.0 Hz, H-2,6), 5.89 (s, 2H, phenol OH), 4.11-4.05 (m, 2H, OCH$_2$CH$_3$), 3.88 (s, 6H, OCH$_3$ X 2), 2.38-2.19 (m, 4H, C4-CH$_2$CH$_2$CO—), 1.42 (s, 3H, CH$_3$—C4), 1.21 (t, 3H, J=7.2 Hz, OCH$_2$CH$_3$).

phenyl ethanesulfonate was synthesized starting from reaction of 3-methoxybenzaldehyde by the method described by U. Peterson (Liebigs Ann. Chem. 1985, 1557-1569) to give compound Q1 (Scheme 19). Methylation at C4 position through the method described above to yield compound Q2. Removal of the protecting group by stirring Q2 in 50% HOAc at 80° C. for 5 hrs followed by extraction with EtOAc and purification by PTLC to get Q3. The desired product 30 was obtained by introducing an ethane sulfonyl group (reaction with 3 eq. of ethane sulfonyl chloride and triethyl amine in CH$_2$Cl$_2$ for 3 hrs) as described above. Light yellow amorphous, ESI MS m/z: 497.4 [M+H]$^+$. $^1$H NMR (400 MHz, CDCl$_3$) δ: 7.66 (d, 1H, J=15.6 Hz, H-1), 7.63 (d, 1H, J=15.6 Hz, H-7), 7.43 (d, br, 1H, J=7.6 Hz, aromatic H), 7.37 (t, 1H, J=8.0 Hz, aromatic H), 7.34 (t, 1H, J=1.6 Hz, aromatic-H), 7.28-7.23 (m, 3H, aromatic H), 7.09 (d, br, 1H, J=7.6 Hz, aromatic H), 6.99 (t, 1H, J=1.6 Hz, aromatic H), 6.90 (dd, 1H, J=2.4, 8.0 Hz, aromatic H), 6.73 (d, 1H, J=15.6 Hz, H-2), 6.71 (d, 1H, J=15.6 Hz, H-6), 3.79 (s, 3H, OCH$_3$), 3.27 (q, 2H, J=7.2, Hz, OSO$_2$CH$_2$CH$_3$), 2.28-2.18 (m, 1H, cyclobutane), 2.14 (s, 1H, C4-CH$_2$), 2.12 (d, 1H, J=2.4, Hz,

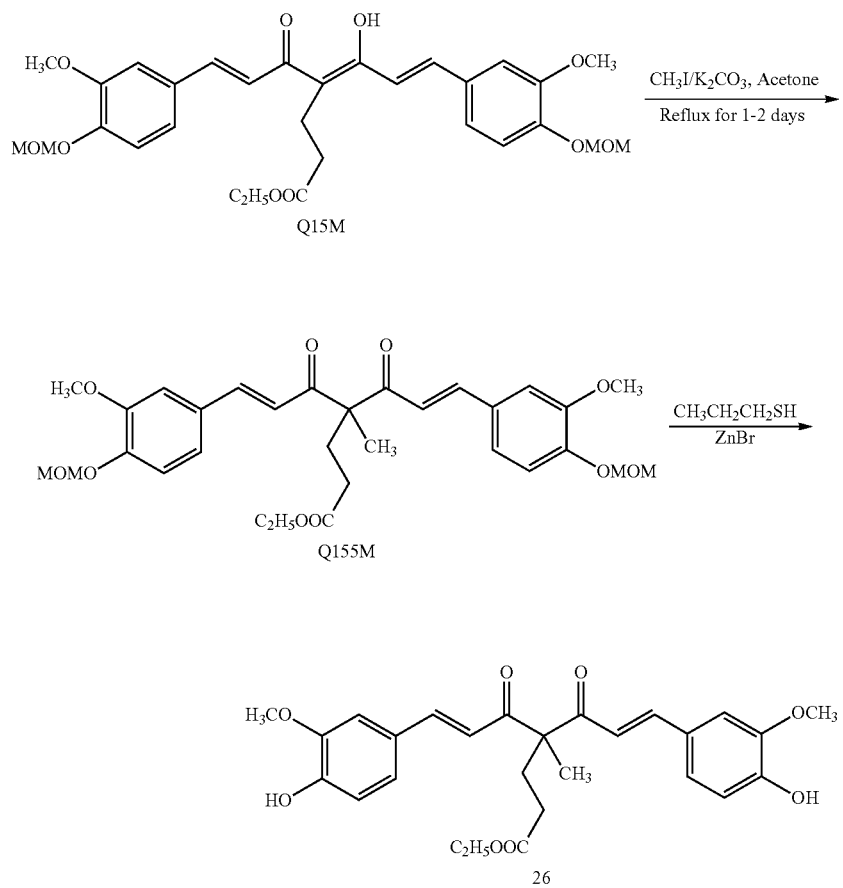

Synthesis of Compound 30

Compound 30, 3-((1E,6E)-4-(cyclobutylmethyl)-7-(3-methoxyphenyl)-4-methyl-3,5-dioxohepta-1,6-dien-1-yl)

C4-CH$_2$), 1.99-1.92 (m, 2H, cyclobutane), 1.81-1.61 (m, 4H, cyclobutane), 1.52 (t, 3H, OSO$_2$CH$_2$CH$_3$), 1.40 (s, 3H, C4-CH$_3$).

Scheme 19

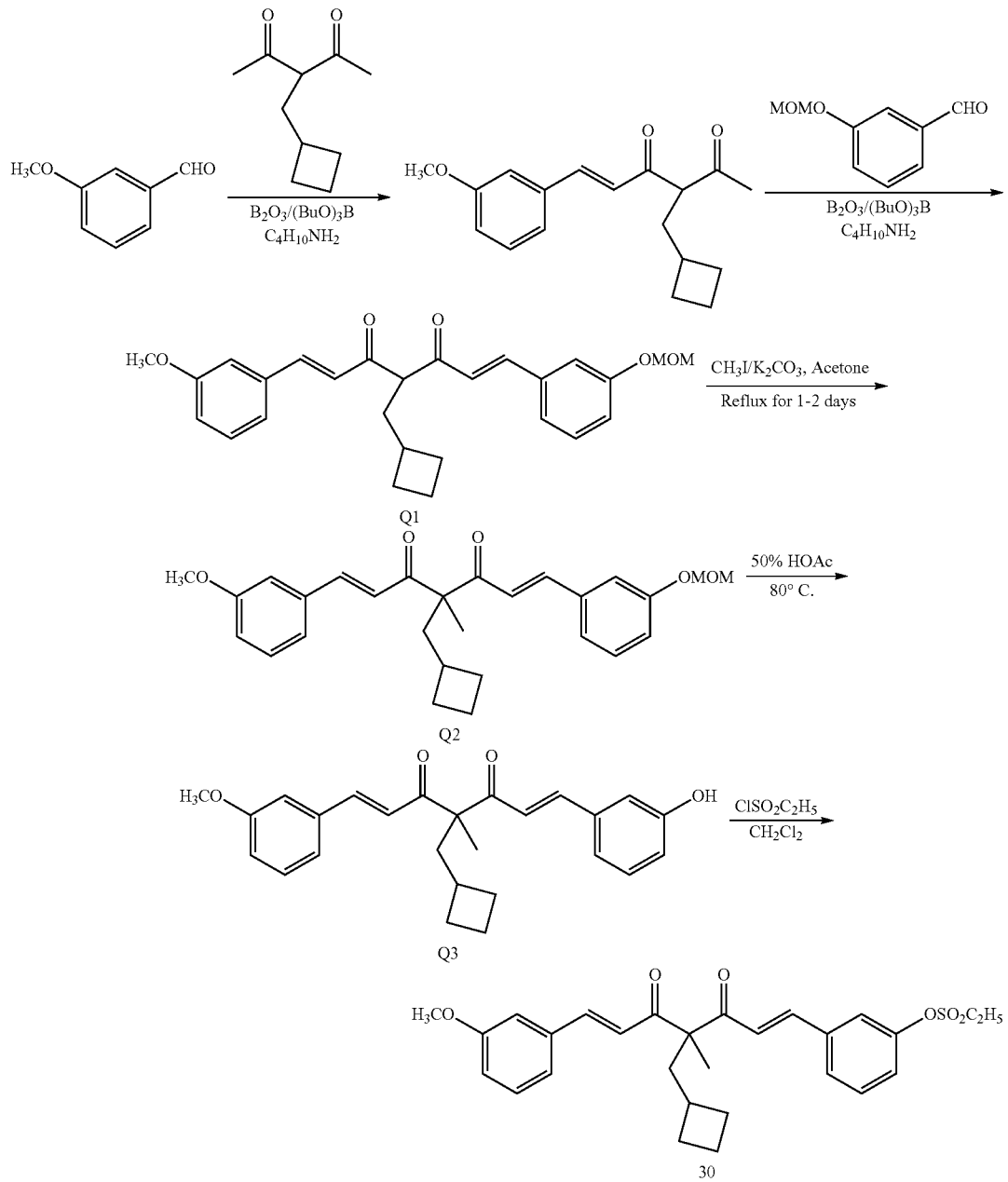

Synthesis of Compounds 32-33

Compounds 32-33 were synthesized starting from 1,2-dimethoxy-4-propylbenzene by reaction with DDQ in 1,4-dioxane under sonication (Scheme 7). The resulting aldehyde (>70% yield) was further reacted with appropriate 3-substituted diones (U. Peterson: Liebigs Ann. Chem. 1985, 1557-1569) to give the compounds JM49Z6 and JM17Z6. Methylation of JM49Z6 with methyl iodide (1.2 eq.) in refluxing acetone as described above afforded compound 32. Reaction of JM17Z6 with N-Fluorodibenzenesulfonimide in acetonitrile at r.t as described above yielded the desired product 33.

Compound 32, yellow-orange amorphous, ESI MS m/z: 576.6[M+H]$^+$. $^1$H NMR (400 MHz, CDCl$_3$) δ: 7.46 (d, 1H, J=15.0 Hz, H-3), 7.43 (d, 1H, J=15.0 Hz, H-9), 6.99-6.95 (m, 4H, aromatic H), 6.86 (d, 2H, J=15.2 Hz, H-1,11), 6.80 (d, 2H, J=8.0 Hz, aromatic H), 6.72 (d, 1H, J=15.2 Hz, H-2), 6.69 (d, 1H, J=15.2 Hz, H-10), 6.45 (d, 2H, J=15.0 Hz, H-4,8), 3.84 (12H, OCH$_3$ X 4), 3.36-3.29 (m, 4H, —N(CH$_2$CH$_3$)$_2$, 3.09 (s, 2H, C4-CH$_2$CO), 1.54 (s, 3H, CH$_3$—C4), 1.23-1.13 (m, 6H, —N(CH$_2$CH$_3$)$_2$).

Compound 33, yellow-orange amorphous, ESI MS m/z: 535.6[M+H]$^+$. $^1$H NMR (400 MHz, CDCl$_3$) δ: 7.51 (d, 1H, J=14.8 Hz, H-3), 7.49 (d, 1H, J=14.8 Hz, H-9), 7.03-6.98 (m, 4H, aromatic H), 6.94 (d, 2H, J=15.2 Hz, H-1,11), 6.83 (d, 2H, J=8.4 Hz, aromatic H), 6.79 (d, 1H, J=15.2 Hz, H-2), 6.76 (d, 1H, J=15.2 Hz, H-10), 6.68 (dd, 2H, J=2.4, 14.8 Hz, H-4,8), 3.90 (6H, OCH$_3$ X 2), 3.88 (6H, OCH$_3$ X 2), 2.47-2.38 (m, 1H, cyclobutane), 2.31 (d, 1H, J=7.2, C4-CH$_2$), 2.25 (d, 1H, J=7.2, Hz, C4-CH$_2$), 2.00-1.85 (m, 2H, cyclobutane), 1.83-1.64 (m, 4H, cyclobutane).

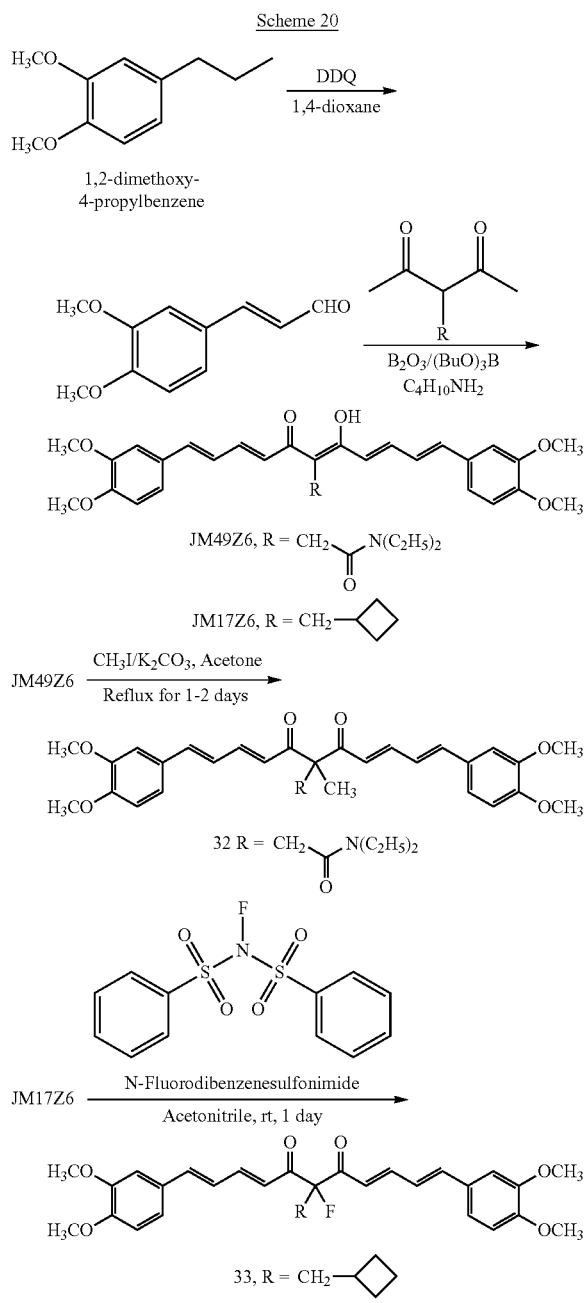

Example 4

Detecting Biological Activity of Compounds and Derivatives having (1E, 6E)-1,7-bis-(substituted phenyl)-4,4-disubstituted-hepta-1,6-diene-3,5-dione or (1E, 10E)-1,11-bis(substituted phenyl)-6,6-disubstituted undeca-1,3,8,10-tetraene-5,7-dione Structural Scaffold The materials and methods used in this example have been described above in this application, such as but not limited to, Example 2. The results of the following assays and experiments are provided in Table 2.

For AR reduction, the indicated compound induced AR protein expression in cancer cells as assayed and determined by Western blotting at 24 or 48 hr post-incubation. The dose of each compound, which induces 50% reduction of AR expression are shown.

For inhibition of tumor cell growth, in vitro, cells were growth in the presence of testing compounds for 5 days, and the cell growth was assayed by standard MTT assay. The dose of each compound, which induces 50% growth inhibition are shown.

TABLE 2

Biological activity of Compounds and Derivatives having (1E,6E)-1,7-bis-(3,4-dimethoxyphenyl)-4,4-disubstituted-hepta-1,6-diene-3,5-dione OR (1E,10E)-1,11-bis(substituted phenyl)-6,6-disubstituted undeca-1,3,8,10-tetraene-5,7-dione structural scaffold

| | CWR22Rv1 cells (human prostate cancer) | | |
|---|---|---|---|
| | Reduction of AR expression IC$_{50}$ (μM) | | Inhibition of Tumor cells growth |
| Compound | 24 h | 48 h | IC$_{50}$ (μM) |
| ASC-J9 ® | 5.0 | 5.0 | 4.0 |
| 1 | | 2.1 | 2.4 |
| 2 | | >5 | >7.5 |
| 3 | 2.8 | | ND |
| 4 | | 3.2 | 2.6 |
| 5 | | 4.0 | 4.6 |
| 6 | 1.0 | | 1.5 |
| 7 | 3.5 | | 2.0 |
| 8 | >5 | | 2.3 |
| 9 | >7.5 | | ND |
| 10 | 3.5 | | ND |
| 11 | 2.2 | | ND |
| 12 | ND | | ND |
| 13 | | >5 | >5 |
| 14 | | 1.5 | 3.6 |
| 15 | | 2.5 | 3.2 |
| 16 | | 3.5 | 4 |
| 17 | >5 | | >7.5 |
| 18 | >5 | | >7.5 |
| 19 | >5 | | 4.7 |
| 20 | 3.0 | | 4.0 |
| 21 | 4.0 | | >7.5 |
| 22 | 1.8 | | ND |
| 23 | >5 | | |
| 24 | >5 | | |
| 25 | >5 | | |
| 26 | 3.5 | | |
| 27 | >7.5 | | |
| 32 | 2.8 | | |
| 33 | >7.6 | | |

ND = Not done.

Example 5

Improved Stability of Modified Compounds

As shown in Table 3 through Table 5, compounds JM49 and JM77, which possess one enol and one ketone group on the linker of two benzene rings, are chemically unstable at 37° C. in: (i) acidic condition (0.1 N HCl); (ii) in rat plasma and (iii) in human plasma. Under these conditions, for compounds JM49 and JM77, their relative concentration quickly reduced with a period of incubation time, i.e., as early as 1 hr in acidic condition (JM77 in Table 3). However, chemical derivatives according to the Formula VI, where JM49 was modified to Compound 6 and JM77 was modified to Compound 7, the stability of these new derivatives (Compound 6 and Compound 7) had unexpectedly and dramatically improved under all three incubation conditions. As shown in Table 3 (acid condition), where stability of JM77 was 8% at 1 hr., the stability improved to 99% in Compound 7. Also, at 24 hr where stability of JM49 was only 4%, while its derivative Compound 6 had improved to 79%. Similar improvements in stability (from 6-24 hr) were also observed in the conditions of rat plasma (Table 4) and human plasma (Table 5). These data indicate that modification of the compounds with an enol-ketone group to a di-ketone moiety on the linker through chemical modification, according to Formula VI, their chemical as well as metabolic stability has unexpectedly and dramatically improved.

TABLE 3

Relative compound concentration changes (stability) in acidic condition

| Time (h) | Concentration change (%) | | | |
|---|---|---|---|---|
| | JM49 | Compound 6 | JM77 | Compound 7 |
| 0 | 100 | 100 | 100 | 100 |
| 1 | 73 | — | 14 | — |
| 2 | 56 | 100 | 8 | 99 |
| 4 | — | 99 | — | 98 |
| 6 | 38 | — | 0 | — |
| 24 | 4 | 79 | 0 | 81 |
| 48 | — | 56 | — | 58 |

TABLE 4

Relative compound concentration changes (stability) in rat plasma

| Time (h) | Concentration change (%) | | | |
|---|---|---|---|---|
| Rat plasma | JM49 | Compound 6 | JM77 | Compound 7 |
| 0 | 100 | 100 | 100 | 100 |
| 1 | 68 | 98 | 93 | 101 |
| 2 | 54 | 96 | 88 | 100 |
| 6 | 27 | 93 | 73 | 101 |
| 24 | 2 | 77 | 27 | 99 |
| 48 | 0 | 51 | 7 | 86 |

TABLE 5

Relative compound concentration changes (stability) in human plasma

| Time (h) Human plasma | Concentration change (%) | | | |
|---|---|---|---|---|
| | JM49 | Compound 6 | JM77 | Compound 7 |
| 0 | 100 | 100 | 100 | 100 |
| 1 | 90 | 99 | 88 | 100 |
| 2 | 75 | 97 | 76 | 99 |
| 6 | 41 | 91 | 45 | 95 |
| 24 | 9 | 54 | 11 | 71 |
| 48 | 0 | 27 | 1 | 49 |

All publications, including patent documents and scientific articles, referred to in this application and any bibliography and attachments, are incorporated by reference in their entirety for all purposes to the same extent as if each individual publication were individually incorporated by reference.

All headings are for the convenience of the reader and should not be used to limit the meaning of the text that follows the heading, unless so specified.

The invention claimed is:

1. A compound of formula (VI):

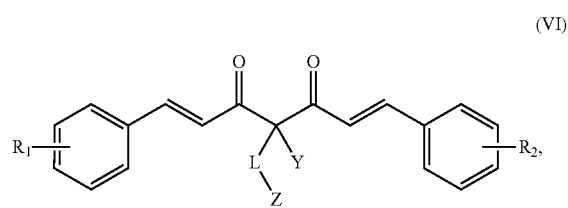

wherein $R_1$ and $R_2$ are each independently selected from a methoxy group, a hydroxyl group, and an alkyl sulfonyl group;

L is a carbonyl, alkylene, or alkenylene, or alkynl when Z is not present;

Z is —H, —OH, a substituted styrenyl, a cycloalkyl, —COR$_3$, —CONR$_3$R$_4$, or —CX$_3$, in which R$_3$ and R$_4$ are each independently —H, —CH$_3$, —C$_n$H$_{2n+1}$, n being 2-4, a heterocyclic, a heteroaryl, or a cycloalkyl, or R$_3$ and R$_4$ together form a heterocyclic, and X is a halogen; or Z is COOR, in which R is —H, —CH$_3$, or —C$_n$H$_{2n+1}$, n being 2-4; and Y is an alkyl, wherein each phenyl of the compound is mono- or di-substituted by $R_1$ or $R_2$.

2. The compound of claim 1, wherein each of $R_1$ and $R_2$ is —OCH$_3$, L is an alkylene, Z is COOR, R being —C$_n$H$_{2n+1}$, wherein n=2-4, and Y is an alkyl.

3. The compound of claim 1, wherein L and Z together form a group selected from

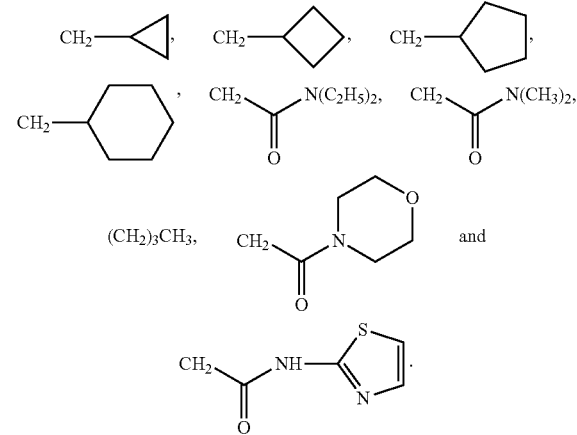

4. The compound of claim 1, wherein the compound is

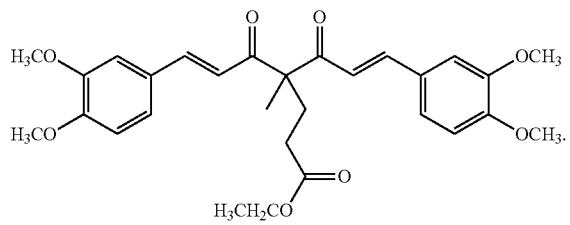

5. A compound of formula (VII):

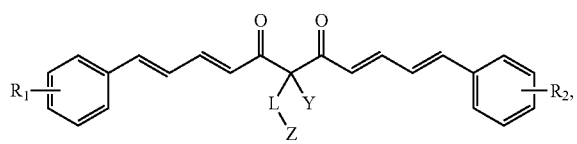

wherein
R₁ and R₂ are each independently selected from a methoxy group, a hydroxyl group, and an alkyl sulfonyl group;
L is a carbonyl, alkylene, or alkenylene, or alkynl when Z is not present;
Z is —H, —OH, a substituted styrenyl, a cycloalkyl, —COR₃, —CONR₃R₄, or —CX₃, in which R₃ and R₄ are each independently —H, —CH₃, —$C_nH_{2n+1}$, n being 2-4, a heterocyclic, a heteroaryl, or a cycloalkyl, or R₃ and R₄ together form a heterocyclic, and X is a halogen; or Z is COOR, in which R is —H, —CH₃, or —$C_nH_{2n+1}$, n being 2-4; and
Y is an alkyl,
wherein each phenyl of the compound is mono- or di-substituted by R₁ or R₂.

6. The compound of claim 5, wherein each of R₁ and R₂ is —OCH₃, L is an alkylene, Z is COOR, R being —$C_nH_{2n+1}$, wherein n=2-4, and Y is an alkyl.

7. The compound of claim 5, wherein L and Z together form a group selected from

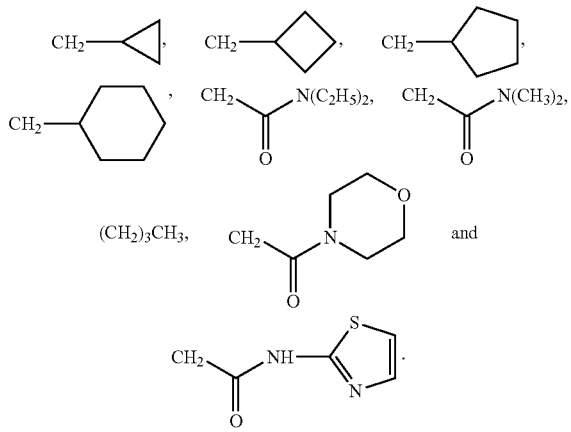

8. A pharmaceutical composition for treating a subject suffering from an androgen receptor associated medical condition, the pharmaceutical composition comprising a pharmaceutically acceptable carrier and a compound of formula (VI):

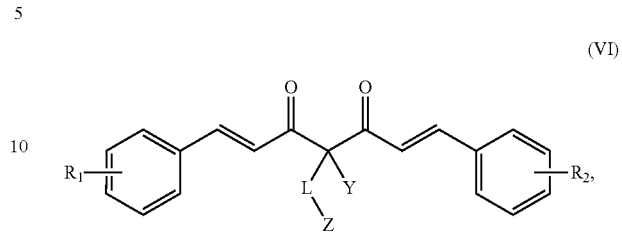

wherein
R₁ and R₂ are each independently selected from a methoxy group, a hydroxyl group, and an alkyl sulfonyl group;
L is a carbonyl, alkylene, or alkenylene, or alkynl when Z is not present;
Z is —H, —OH, a substituted styrenyl, a cycloalkyl, —COR₃, —CONR₃R₄, or —CX₃, in which R₃ and R₄ are each independently —H, —CH₃, —$C_nH_{2n+1}$, n being 2-4, a heterocyclic, a heteroaryl, or a cycloalkyl, or R₃ and R₄ together form a heterocyclic, and X is a halogen; or Z is COOR, in which R is —H, —CH₃, or —$C_nH_{2n+1}$, n being 2-4; and
Y is an alkyl,
wherein each phenyl of the compound is mono- or di-substituted by R₁ or R₂, and wherein the androgen receptor associated medical condition is selected from inflammation, acne, alopecia, hirsutism, wound, Spinal and Bulbar Muscular Atrophy (SBMA, Kennedy's Disease), unwanted immune response, immune disorder, or cancer.

9. The pharmaceutical composition of claim 8, wherein each of R₁ and R₂ is —OCH₃, L is an alkylene, Z is COOR, R being —$C_nH_{2n+1}$, wherein n=2-4, and Y is an alkyl.

10. The pharmaceutical composition of claim 8, wherein L and Z together form a group selected from

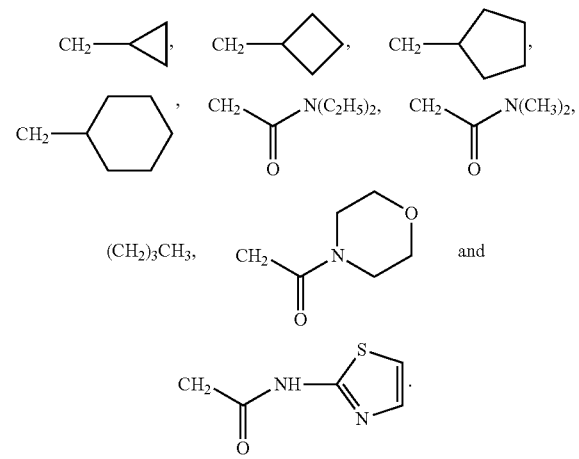

11. The pharmaceutical composition of claim 8, wherein the compound is

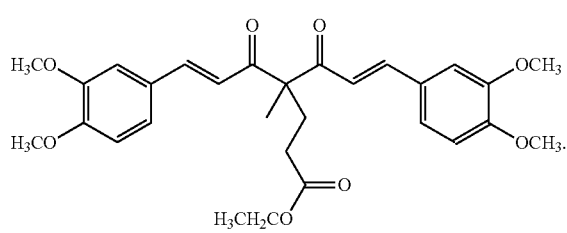

12. A method for treating a subject suffering from an androgen receptor associated medical condition, the method comprising administering to the subject an effective amount of a compound of formula (VI):

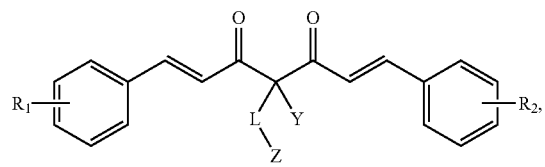

(VI)

wherein
  $R_1$ and $R_2$ are each independently selected from a methoxy group, a hydroxyl group, and an alkyl sulfonyl group;
  L is a carbonyl, alkylene, or alkenylene, or alkynl when Z is not present;
  Z is —H, —OH, a substituted styrenyl, a cycloalkyl, —$COR_3$, —$CONR_3R_4$, or —$CX_3$, in which $R_3$ and $R_4$ are each independently —H, —$CH_3$, —$C_nH_{2n+1}$, n being 2-4, a heterocyclic, a heteroaryl, or a cycloalkyl, or $R_3$ and $R_4$ together form a heterocyclic, and X is a halogen; or Z is COOR, in which R is —H, —$CH_3$, or —$C_nH_{2n+1}$, n being 2-4; and
  Y is an alkyl,
wherein each phenyl of the compound is mono- or di-substituted by $R_1$ or $R_2$, and wherein the androgen receptor associated medical condition is selected from inflammation, acne, alopecia, hirsutism, wound, Spinal and Bulbar Muscular Atrophy (SBMA, Kennedy's Disease), unwanted immune response, immune disorder, or cancer.

13. The method of claim 12, wherein each of $R_1$ and $R_2$ is —$OCH_3$, L is an alkylene, Z is COOR, R being —$C_nH_{2n+1}$, wherein n=2-4, and Y is an alkyl.

14. The method of claim 12, wherein L and Z together form a group selected from

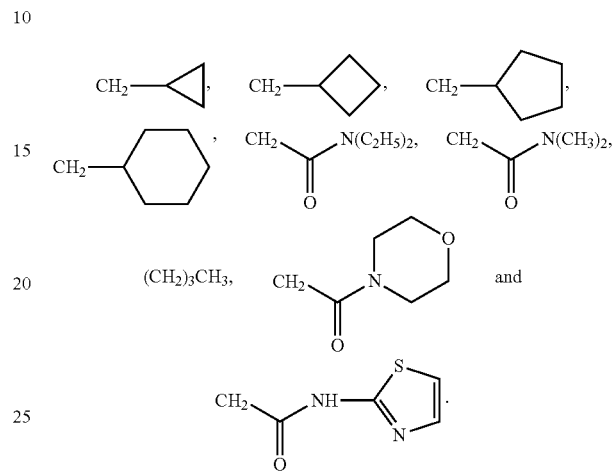

15. The method of claim 12, wherein the compound is

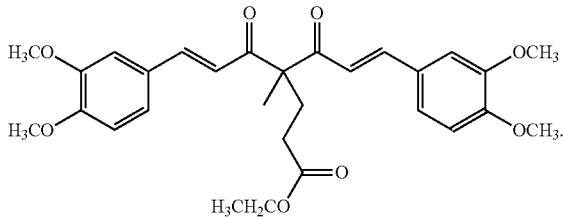

* * * * *